(12) United States Patent
Lefkofsky et al.

(10) Patent No.: US 11,699,507 B2
(45) Date of Patent: Jul. 11, 2023

(54) METHOD AND PROCESS FOR PREDICTING AND ANALYZING PATIENT COHORT RESPONSE, PROGRESSION, AND SURVIVAL

(71) Applicant: Tempus Labs, Inc., Chicago, IL (US)

(72) Inventors: Hailey Lefkofsky, Chicago, IL (US); Ashraf Hafez, Wheaton, IL (US); Julian Habib, Chicago, IL (US); Carin Fishel, Chicago, IL (US); Caroline Epstein, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/382,343

(22) Filed: Jul. 22, 2021

(65) Prior Publication Data
US 2021/0350937 A1 Nov. 11, 2021

Related U.S. Application Data

(63) Continuation of application No. 16/732,168, filed on Dec. 31, 2019.
(Continued)

(51) Int. Cl.
*G16H 50/70* (2018.01)
*G16H 50/20* (2018.01)
(Continued)

(52) U.S. Cl.
CPC ............. *G16H 10/20* (2018.01); *G06F 17/18* (2013.01); *G06F 18/214* (2023.01); *G06F 18/2115* (2023.01); *G06F 18/22* (2023.01); *G06F 18/24* (2023.01); *G06F 18/24323* (2023.01); *G06F 21/62* (2013.01); *G06N 5/01* (2023.01);
(Continued)

(58) Field of Classification Search
CPC ..................................................... G16H 50/70
See application file for complete search history.

(56) References Cited

U.S. PATENT DOCUMENTS 10,049,772 B1    8/2018   Price, Jr. et al.
10,395,772 B1    8/2019   Lucas
(Continued)

FOREIGN PATENT DOCUMENTS

DE   102007007190 A1 *   8/2007   ......... G06F 19/3481
WO   2016118771 A1    7/2016
WO   2017186048 A1    11/2017

OTHER PUBLICATIONS

Sinsel, Ensemble Learning for Ranking Interesting Attributes, 2005, West Virginia University (Year: 2005).*
(Continued)

*Primary Examiner* — Shahid Merchant
*Assistant Examiner* — Karen A Hranek
(74) *Attorney, Agent, or Firm* — Quarles & Brady LLP

(57) ABSTRACT

A system and method for analyzing a data store of de-identified patient data to generate one or more dynamic user interfaces usable to predict an expected response of a particular patient population or cohort when provided with a certain treatment. The automated analysis of patterns occurring in patient clinical, molecular, phenotypic, and response data, as facilitated by the various user interfaces, provides an efficient, intuitive way for clinicians to evaluate large data sets to aid in the potential discovery of insights of therapeutic significance.

27 Claims, 37 Drawing Sheets

Related U.S. Application Data

(60) Provisional application No. 62/786,739, filed on Dec. 31, 2018.

(51) Int. Cl.

| | | |
|---|---|---|
| *G06K 9/62* | (2022.01) | |
| *G16H 10/60* | (2018.01) | |
| *G06N 20/00* | (2019.01) | |
| *G06F 17/18* | (2006.01) | |
| *G16H 30/00* | (2018.01) | |
| *G16H 80/00* | (2018.01) | |
| *G06F 21/62* | (2013.01) | |
| *G16H 10/20* | (2018.01) | |
| *G06F 18/22* | (2023.01) | |
| *G06F 18/24* | (2023.01) | |
| *G06F 18/214* | (2023.01) | |
| *G06F 18/2115* | (2023.01) | |
| *G06F 18/243* | (2023.01) | |
| *G06N 5/01* | (2023.01) | |
| *G06N 5/00* | (2023.01) | |

(52) U.S. Cl.
CPC ............. *G06N 20/00* (2019.01); *G16H 10/60* (2018.01); *G16H 30/00* (2018.01); *G16H 50/20* (2018.01); *G16H 50/70* (2018.01); *G16H 80/00* (2018.01)

(56) References Cited

U.S. PATENT DOCUMENTS

| | | | |
|---|---|---|---|
| 2002/0049740 A1 | 4/2002 | Arning et al. | |
| 2003/0061228 A1 | 3/2003 | Kamath et al. | |
| 2005/0074795 A1 | 4/2005 | Hoffman et al. | |
| 2005/0108753 A1 | 5/2005 | Saidi et al. | |
| 2007/0178501 A1 | 8/2007 | Rabinowitz et al. | |
| 2009/0043172 A1 | 2/2009 | Zagorchev et al. | |
| 2009/0061422 A1* | 3/2009 | Linke | G16B 40/00 703/11 |
| 2009/0076845 A1 | 3/2009 | Bellin et al. | |
| 2009/0319244 A1 | 12/2009 | West | |
| 2010/0114900 A1 | 5/2010 | Anderson | |
| 2012/0021935 A1 | 1/2012 | Cazaux | |
| 2012/0131484 A1 | 5/2012 | Neumann et al. | |
| 2013/0085980 A1* | 4/2013 | Alemi | G06Q 10/00 706/50 |
| 2013/0185096 A1 | 7/2013 | Giusti et al. | |
| 2013/0226612 A1* | 8/2013 | Carmeli | G06Q 10/04 705/2 |
| 2013/0232103 A1* | 9/2013 | Saeed | G16H 50/20 706/46 |
| 2014/0066328 A1 | 3/2014 | Modlin | |
| 2014/0108379 A1 | 4/2014 | Gotz et al. | |
| 2014/0162887 A1 | 6/2014 | Martin | |
| 2014/0236618 A1 | 8/2014 | Rawlings et al. | |
| 2014/0244625 A1 | 8/2014 | Seghezzi | |
| 2014/0249761 A1 | 9/2014 | Carroll | |
| 2014/0279775 A1* | 9/2014 | Chu | G06N 5/022 706/20 |
| 2015/0221110 A1 | 8/2015 | Holmen | |
| 2015/0331909 A1 | 11/2015 | Sundquist | |
| 2016/0019666 A1 | 1/2016 | Amarasingham | |
| 2016/0063212 A1* | 3/2016 | Monier | G16H 10/60 705/3 |
| 2016/0196398 A1 | 7/2016 | Vivero et al. | |
| 2016/0253469 A1 | 9/2016 | Donovan | |
| 2016/0317077 A1 | 11/2016 | Sillay | |
| 2017/0091394 A1 | 3/2017 | Gurupur et al. | |
| 2017/0177597 A1 | 6/2017 | Asimenos | |
| 2017/0177822 A1* | 6/2017 | Fogel | G16H 50/20 |
| 2017/0199965 A1 | 7/2017 | Dekel | |
| 2017/0237805 A1 | 8/2017 | Worley | |
| 2017/0322217 A1 | 11/2017 | Batagov et al. | |
| 2018/0144003 A1 | 5/2018 | Formoso | |
| 2018/0165604 A1 | 6/2018 | Minkin et al. | |
| 2018/0226153 A1* | 8/2018 | Rubenstein | G16H 50/50 |
| 2018/0268937 A1 | 9/2018 | Spetzler et al. | |
| 2018/0300454 A1* | 10/2018 | Chan | G16H 50/20 |
| 2018/0300456 A1 | 10/2018 | Eltoukhy et al. | |
| 2018/0336487 A1* | 11/2018 | Moore | G06N 5/003 |
| 2019/0034591 A1 | 1/2019 | Mossin et al. | |
| 2019/0108912 A1* | 4/2019 | Spurlock, III | G16H 50/20 |
| 2019/0250975 A1 | 8/2019 | Bertiger et al. | |
| 2019/0371443 A1* | 12/2019 | Petricoin, III | G16H 20/10 |
| 2019/0371450 A1* | 12/2019 | Lou | G16H 10/60 |
| 2020/0098451 A1* | 3/2020 | Krishnan | G06N 20/20 |
| 2020/0105413 A1 | 4/2020 | Vladimirova | |
| 2020/0126675 A1 | 4/2020 | Park et al. | |
| 2020/0211716 A1 | 7/2020 | Lefkofsky et al. | |
| 2020/0219619 A1* | 7/2020 | Feczko | G06N 20/20 |
| 2020/0258601 A1 | 8/2020 | Lau | |
| 2020/0334228 A1 | 10/2020 | Matyska et al. | |
| 2021/0142910 A1 | 5/2021 | Hafez et al. | |
| 2021/0249132 A1* | 8/2021 | Colborn | G16H 20/00 |

OTHER PUBLICATIONS

Jeffares, Decision Trees: A Complete Introduction, Jul. 25, 2018, Towards Data Science (Year: 2018).*

Austin, PC "An Introduction to Propensity Score Methods for Reducing the Effects of Confounding in Observational Studies." Multivariate Behavioral Research 46.3 (2011): 399.

Austin, The use of propensity score methods with survival or time-to-event outcomes: reporting measures of effect similar to those used in randomized experiments, Statistics in Medicine (2013), 33:1242-1258.

International Searching Authority, International Search Report & Written Opinion for application PCT/US2019/069149, dated Apr. 29, 2020.

Rosenbaum & Rubin. The central role of the propensity score in observational studies for causal effects, Biometrika (1983), 70(1):41-55.

Stuart, E. Matching methods for causal inference: a review and a look forward, Statistical Science (2010) 25(1):1-21.

DNAnexus. Working with UK Biobank: A Research Guide. Accessed online on Dec. 31, 2020. Available at https://web.archive.org/save/https://dna-nexus-prod-s3-assets-51tcpaqcp0pd.s3.amazonaws.com/images/files/DNAnexus_WhitePaper_Working-with-UKB-Data_2.pdf.

Caris Life Sciences. CODE: Comprehensive Oncology Data Explorer. Slideshow May 2017. Accessed on Dec. 16, 2020 at https://www.karmanos.org/Uploads/Public/Documents/Karmanos/CODE%20slides_5.2017.pptx%20.

Rokach L., et al., "Decision Trees" (2005) Data Mining and Knowledge Discovery Handbook, pp. 165-192.

Al-Nachawati et al., Tree-Structured Analysis of Survival Data and Its Application Using SAS Software, Journal of King Saud University (Science), 2010, 22:251-255.

Carrasquinha et al., Consensus Outlier Detection in Survival Analysis Using the Rank Product Test, bioRxiv preprint doi: https://doi.org/10.1101/421917, Sep. 20, 2018, pp. 1-27.

Dean, A Method for Detecting Optimal Splits Over Time in Survival Analysis Using Tree-Structured Models, Submitted to Graduate School of Public Health of the University of Pittsburgh, 2007, 24 pages.

Jin et al., Alternative Tree-Structured Survival Analysis Based on Variance of Survival Time, Medical Decision Making, Nov.-Dec. 2004, pp. 670-680.

Kopcke et al., Evaluation of Data Completeness in the Electronic Health Record for the Purpose of Patient Recruitment Into Clinical Trials: A Retrospective Analysis of Element Presence, BMC Medical Informatics and Decision Making, 2013, 13:37, pp. 1-8.

Kourou et al., Machine Learning Applications in Cancer Prognosis and Prediction, Computational and Structural Biotechnology Journal, 2015, 13:8-17.

(56) References Cited

OTHER PUBLICATIONS

Lee et al., Third-Generation Sequencing and the Future of Genomics, bioRxiv preprint doi: https://doi.org/10.1101/048603, Apr. 13, 2016, 20 pages.

Mostafa et al., Overviews of "Next-Generation Sequencing", Research and Reports in Forensic Medical Science, 2015, 5:1-5.

Nasir et al., A New Paradigm to Analyze Data Completeness of Patient Data, Applied Clinical Informatics, 2016, 7:745-764.

Negassa et al., Tree-Structured Subgroup Analysis for Censored Survival Data: Validation of Computationally Inexpensive Model Selection Criteria, Statistics and Computing, 2005, 15:231-239.

Ture et al., Using Kaplan-Meier Analysis Together with Decision Tree Methods (C&RT, Chaid, Quest, C4.5 and ID3) in Determining Recurrence-Free Survival of Breast Cancer Patients, Expert Systems with Applications, 2009, 36:2017-2026.

Zhang et al., Recursive Partitioning for Tumor Classification with Gene Expression Microarray Data, PNAS, 2001, 98 (12):6730-6735.

European Patent Office, Extended Search Report, Application No. 19907146.5, dated Aug. 5, 2022, 18 pages.

* cited by examiner

24 ⟶

| TEMPUS | COHORT FUNNEL  SURVIVAL CURVES  SURVIVAL TREE  PATIENT TIMELINE  EXPLORATORY DATA VISUALIZER  ASK GENE |

— 200

236 —

META
PROJECT NAME
[SELECT... ▼] — 204
GENDER
[SELECT... ▼] — 206
RACE
[SELECT... ▼] — 208
CANCER
CANCER SITE NAME
[SELECT... ▼] — 210
CANCER NAME
[SELECT... ▼] — 212
METASTASIS
CANCER NAME
[SELECT... ▼] — 214
TUMOR FINDING
TUMOR FINDING
[SELECT... ▼] — 216
STAGE
[SELECT... ▼] — 218
M_STAGE
[SELECT... ▼] — 220
MEDICATION
MEDICATION NAME
[SELECT... ▼] — 222
INGREDIENT NAME
[SELECT... ▼] — 224
SEQUENCING
GENE NAME+VARIANT
[SELECT... ▼] — 226
IMMUNO MSI STATUS
[SELECT... ▼] — 228
PROCEDURE
PROCEDURE NAME
[SELECT... ▼] — 230
DEATH
EVENT
[SELECT... ▼] — 232
CAUSE OF DEATH
[SELECT... ▼] — 234

| feature | value |
|---|---|
| last stage | 0.14485 |
| cancer: breast_cancer | 0.06266 |
| historical-took_medication: gemcitabine | 0.04721 |
| historical-took_medication: paclitaxel | 0.04686 |
| cancer: lung_cancer | 0.03740 |
| sequencing: pgr:positive | 0.03522 |
| historical-took_medication: carboplatin | 0.03478 |
| historical-took_medication: bevacizumab | 0.03350 |
| cancer: pancreatic_cancer | 0.03221 |
| historical-got_radiotherapy: radiotherapy,_not_otherwise_specified | 0.03046 |

FIG. 27A

| feature | value |
|---|---|
| historical-took_medication: irinotecan | 0.06544 |
| historical-took_medication: bevacizumab | 0.05002 |
| historical-took_medication: oxaliplatin | 0.03810 |
| historical-took_medication: capecitabine | 0.03777 |
| took_medication: oxaliplatin | 0.03711 |
| historical-took_medication: leucovorin | 0.03680 |
| historical-took_medication: fluorouracil | 0.03317 |
| historical-took_medication: cetuximab | 0.03271 |
| took_medication: fluorouracil | 0.02646 |
| sequencing: kras:mutation | 0.02238 |

FIG. 27B

| feature | value |
| --- | --- |
| duplicate_column_1 | 0.06544 |
| historical-took_medication: irinotecan | 0.06544 |
| historical-took_medication: bevacizumab | 0.05002 |
| historical-took_medication: oxaliplatin | 0.03810 |
| duplicate_column_2 | 0.03777 |
| historical-took_medication: capecitabine | 0.03777 |
| took_medication: oxaliplatin | 0.03711 |
| historical-took_medication: leucovorin | 0.03680 |
| historical-took_medication: fluorouracil | 0.03317 |
| historical-took_medication: cetuximab | 0.03271 |

FIG. 27C

METHOD AND PROCESS FOR PREDICTING AND ANALYZING PATIENT COHORT RESPONSE, PROGRESSION, AND SURVIVAL

BACKGROUND

In certain medical fields, for example the areas of cancer research and treatment, voluminous amounts of data may be generated and collected for each patient. This data may include demographic information, such as the patient's age, gender, height, weight, smoking history, geographic location, and other, non-medical information. The data also may include clinical components, such as tumor type, location, size, and stage, as well as treatment data including medications, dosages, treatment therapies, mortality rates, and other outcome/response data. Moreover, more advanced analysis also may include genomic information about the patient and/or tumor, including genetic markers, mutations, as well as other information from fields including proteome, transcriptome, epigenome, metabolome, microbiome, and other multi-omic fields.

Despite this wealth of data, there is a dearth of meaningful ways to compile and analyze the data quickly, efficiently, and comprehensively.

Thus what are needed are a user interface, system, and method that overcome one or more of these challenges.

SUMMARY OF THE INVENTION

In one aspect, a system and user interface are provided to predict an expected response of a particular patient population or cohort when provided with a certain treatment. In order to accomplish those predictions, the system uses a pre-existing dataset to define a sample patient population, or "cohort," and identifies one or more key inflection points in the distribution of patients exhibiting each attribute of interest in the cohort, relative to a general patient population distribution, thereby targeting the prediction of expected survival and/or response for a particular patient population.

The system described herein facilitates the discovery of insights of therapeutic significance, through the automated analysis of patterns occurring in patient clinical, molecular, phenotypic, and response data, and enabling further exploration via a fully integrated, reactive user interface.

In one embodiment the invention provides a method for identifying an outlier group of patients, including: 1) selecting a cohort of patients including a plurality of patients; 2) calculating an average survival rate for the cohort of patients; 3) selecting a plurality of clinical or molecular characteristics associated with the cohort of patients; 4) for each characteristic of the plurality of characteristics: a) identifying a plurality of data values associated with the characteristic, b) for each data value of the plurality of data values associated with the characteristic: i) dividing the cohort of patients into a first subgroup and a second subgroup of the plurality of patients based on whether each patient of the plurality of patients survived during an outlier time period, ii) determining a difference between a number of patients in the first subgroup and the second subgroup, and iii) selecting a data value that results in the difference that is a largest difference between a number of patients in the first subgroup and the second subgroup; 5) creating a new node of a tree structure based on the data value that results in the largest difference between the number of patients in the first subgroup and the second subgroup; 6) creating a first branch from the new node based on the first subgroup; 7) creating a second branch from the new node based on the second subgroup; 8) for each of the first branch and the second branch, repeating steps of 4) b) i-iii) and 5) based on patients in the first subgroup and the second subgroup, respectively, until either: a maximum number of nodes or branches has been created, or a node contains fewer than a minimum number of patients; and 9) identifying at least one node containing an outlier group of patients.

In yet another embodiment the invention provides a method for implementing a prediction model, including: receiving a plurality of data for a plurality of patients for a period of time; identifying, for each of the plurality of patients, a plurality of patient timepoints within the period of time; for each patient of the plurality of patients and for each patient timepoint of the plurality of patient timepoints and based on the plurality of data for the plurality of patients: calculating an outcome target for an outcome event within a horizon time window, identifying a plurality of prior features, and determining a state of each of the plurality of prior features at the patient timepoint; identifying, for each patient timepoint of the plurality of timepoints having a valid outcome target and for each combination of horizon time window and outcome event, a plurality of forward features; and generating a plurality of sets of predictions for the plurality of patients based on the plurality of prior features and the plurality of forward features.

In still another embodiment the invention provides a method, including: receiving patient information for one or more patients; identifying one or more interactions for each of the one or more patients based at least in part on the received patient information; generating, for one or more targets at each of the one or more interactions, one or more timeline metrics identifying whether each of the one or more targets occurs within a time period of an occurrence of the interaction; identifying, for each timeline metric of the one or more timeline metrics, whether a patient may incur one or more status characteristics within the time period; training a target prediction model for each of the one or more targets based at least in part on the one or more status characteristics; and associating predictions for each patient from the target prediction model for each of the one or more targets with a respective one or more timeline metrics of the one or more timeline metrics.

In some embodiments the method may further include: 1) selecting a cohort of patients including a group of patients of the plurality of patients; 2) identifying a common anchor point in time from a set of anchor points associated with each of the group of patients, the common anchor point being shared by each of the group of patients in the cohort; 3) aligning, for each patient of the group of patients, a timeline associated with each patient of the group of patients to the common anchor point; 4) identifying an outcome target; 5) retrieving, for each patient of the group of patients and for each of the plurality of forward features and the plurality of prior features, the generated plurality of sets of predictions each including a predicted target value; 6) generating a plurality of decision trees, including, for decision each tree of the plurality of decision trees: a) for each feature of the plurality of forward features and the plurality of prior features: i) dividing the group of patients into a first subgroup and a second subgroup based on a difference between the predicted target value and an actual target value, ii) determining a difference between a number of patients in the first subgroup and the second subgroup, and iii) selecting a feature that results in the difference that is a largest difference between a number of patients in the first subgroup and the second subgroup; 7) creating a new node of a tree structure based on the feature that results in the largest difference between the number of patients in the first subgroup and the second subgroup; 8) creating a first branch from the new node based on the first subgroup; 9) creating a second branch from the new node based on the second subgroup; and 10) for each of the first branch and the second branch, repeat steps of 6) a) i-iii) and 7) based on patients in the first subgroup and the second subgroup, respectively, until either: a maximum number of nodes or branches has been created, or a node contains fewer than a minimum number of patients.

In other embodiments the method may further include: receiving the plurality of predictions, an outcome target, a subset of the plurality of forward features corresponding to the outcome target, and a cohort of patients including a subset of the plurality of patients; receiving an anchor point; for each patient in the cohort having the anchor point, providing the prediction model with the selected subset of the plurality of forward features and a difference between each of the plurality of predictions and the outcome target; and for each feature of the selected subset of the plurality of forward features, generating a decision tree based on determining a greatest difference between each of the plurality of predictions and the outcome target, wherein the decision tree includes a plurality of leaf nodes and one or more branch nodes, wherein each of the one or more branch nodes includes a pair of branches each of which includes a leaf node or a branch node, and wherein each of the plurality of leaf nodes of the decision tree includes a number of patients from the cohort of patients.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 2 is one example of a patient cohort selection filtering interface;

FIGS. 27A and 27B show an example of adaptive feature ranking in accordance with embodiments of the SAFE algorithm;

FIG. 27C shows an example of handling of correlated features in accordance with embodiments of the SAFE algorithm;

DETAILED DESCRIPTION

Figure 1:
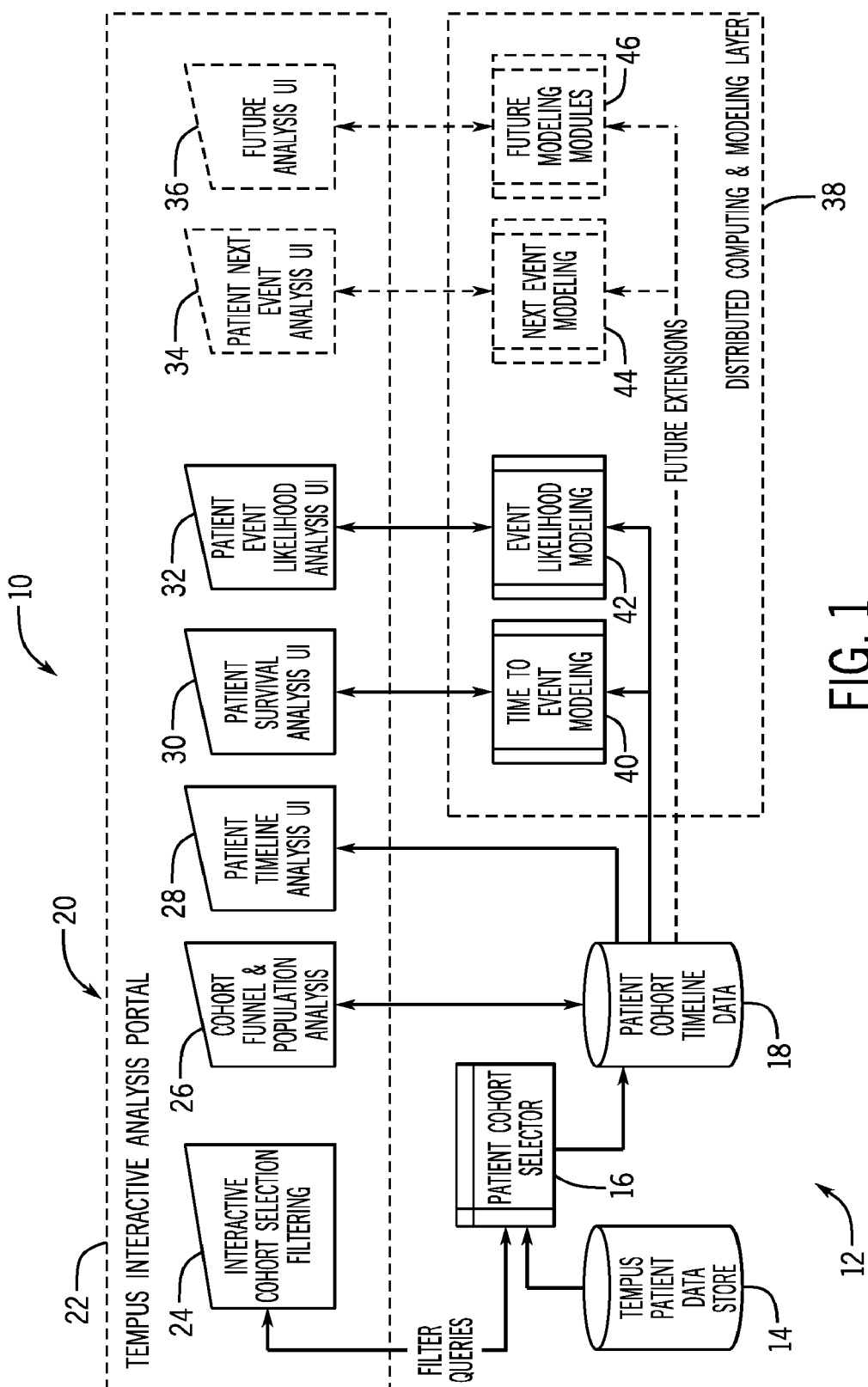
FIG. 1 is an exemplary system diagram of back end and front end components for predicting and analyzing patient cohort response, progression, and survival.
Figure 3:
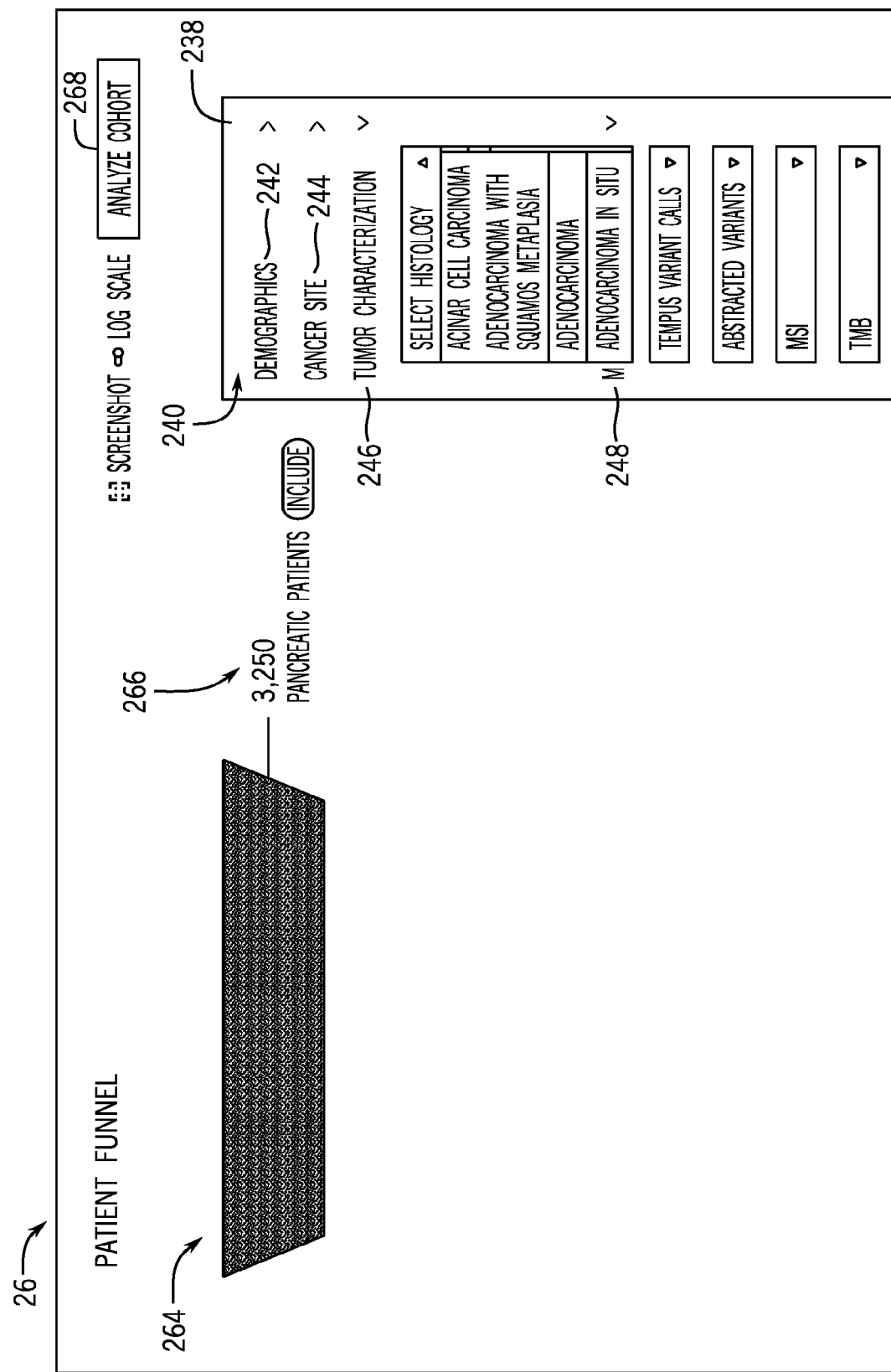
FIG. 3 is one example of a cohort funnel & population analysis user interface.
Figure 4:
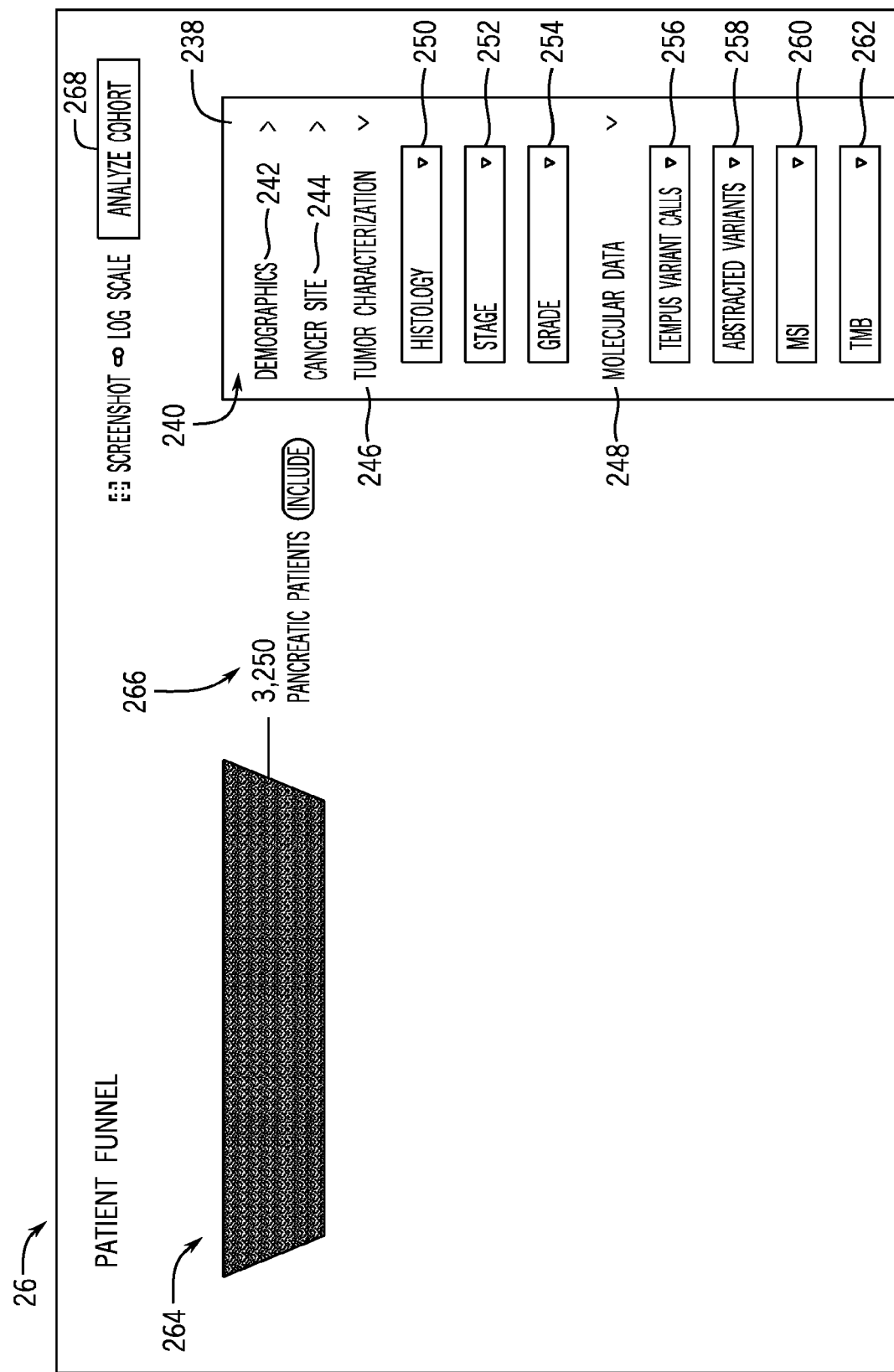
FIG. 4 is another example of a cohort funnel & population analysis user interface.
Figure 5:
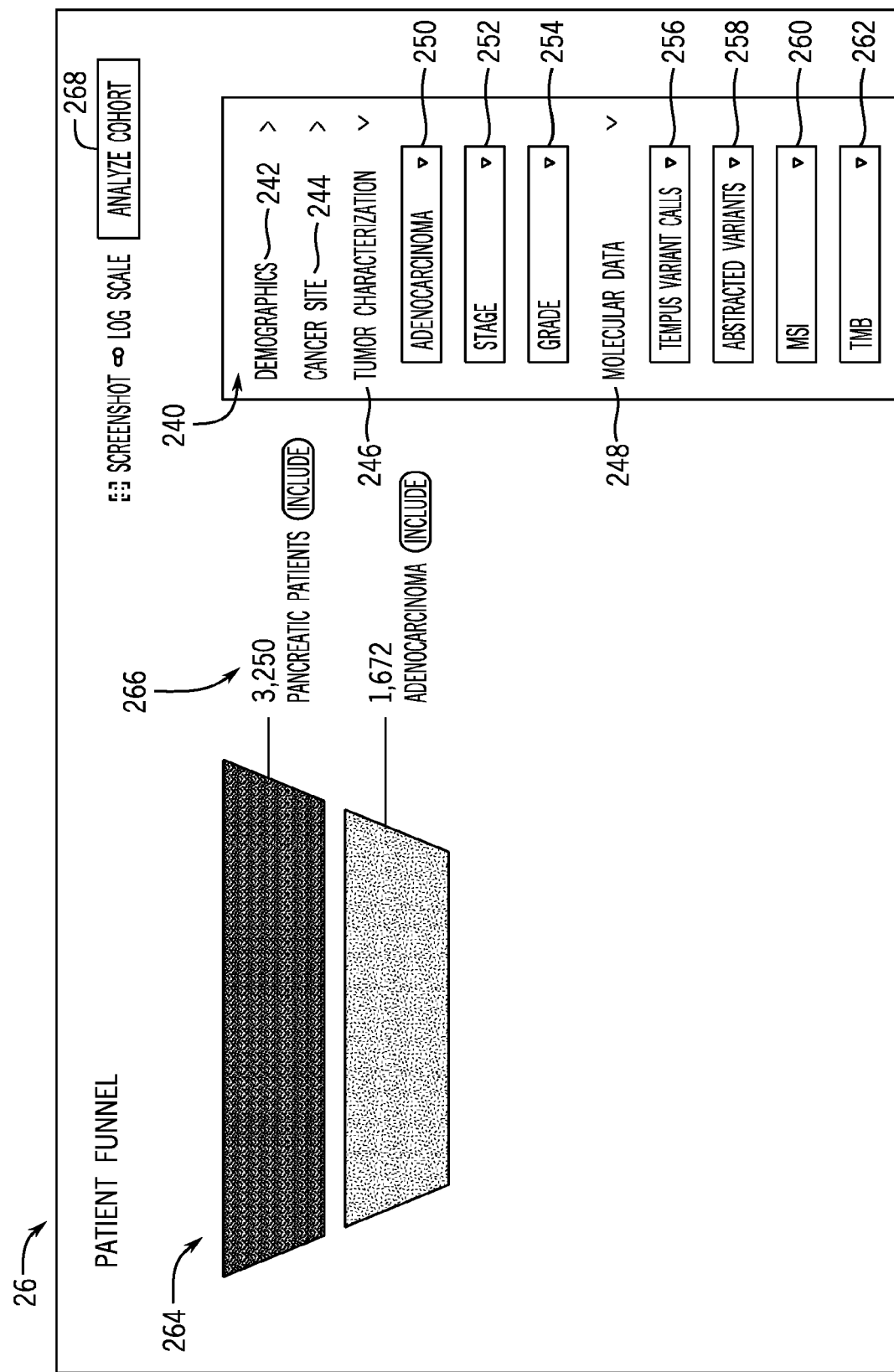
FIG. 5 is another example of a cohort funnel & population analysis user interface.
Figure 6:
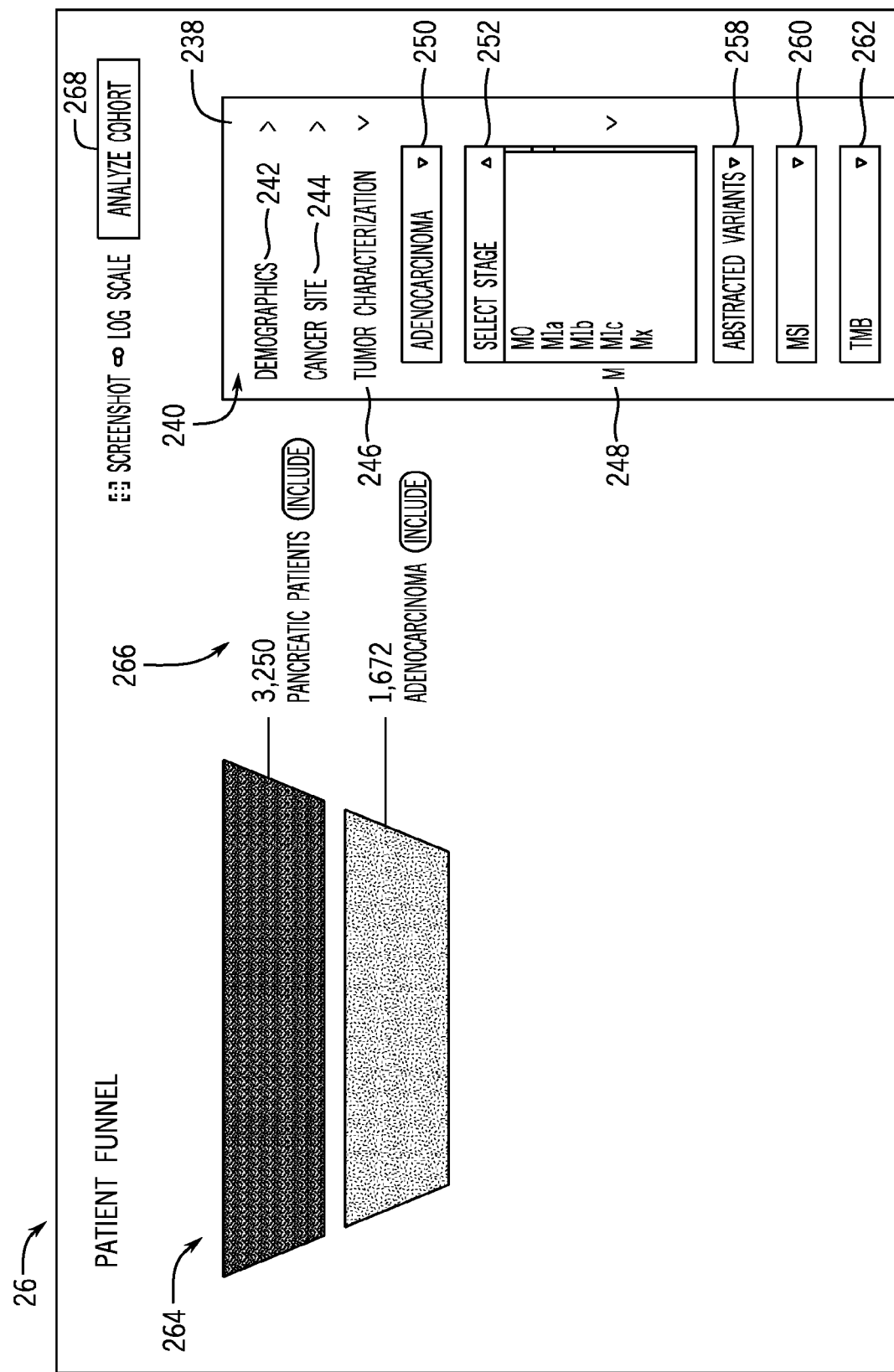
FIG. 6 is another example of a cohort funnel & population analysis user interface.
Figure 7:
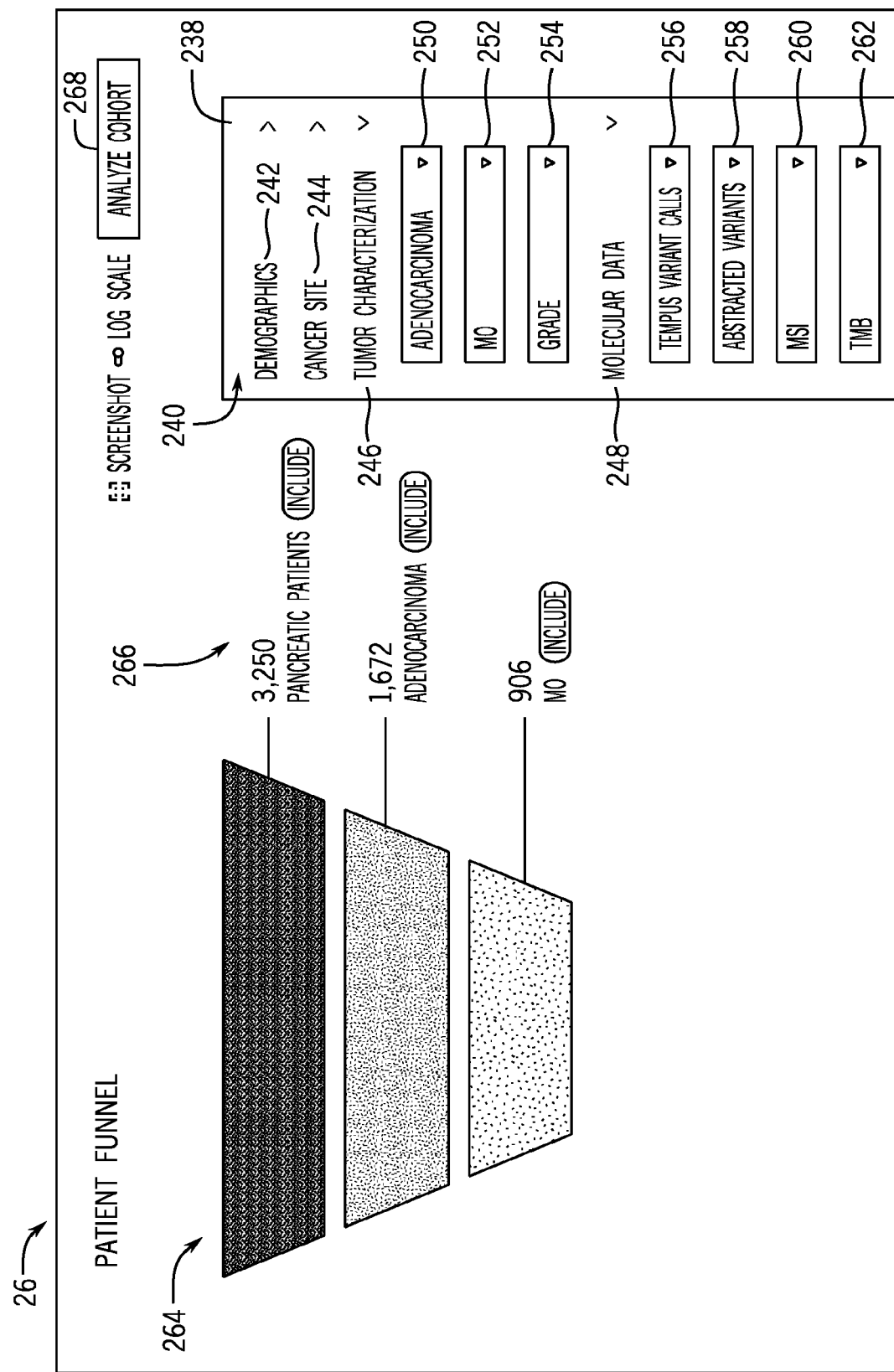
FIG. 7 is another example of a cohort funnel & population analysis user interface.
Figure 8:
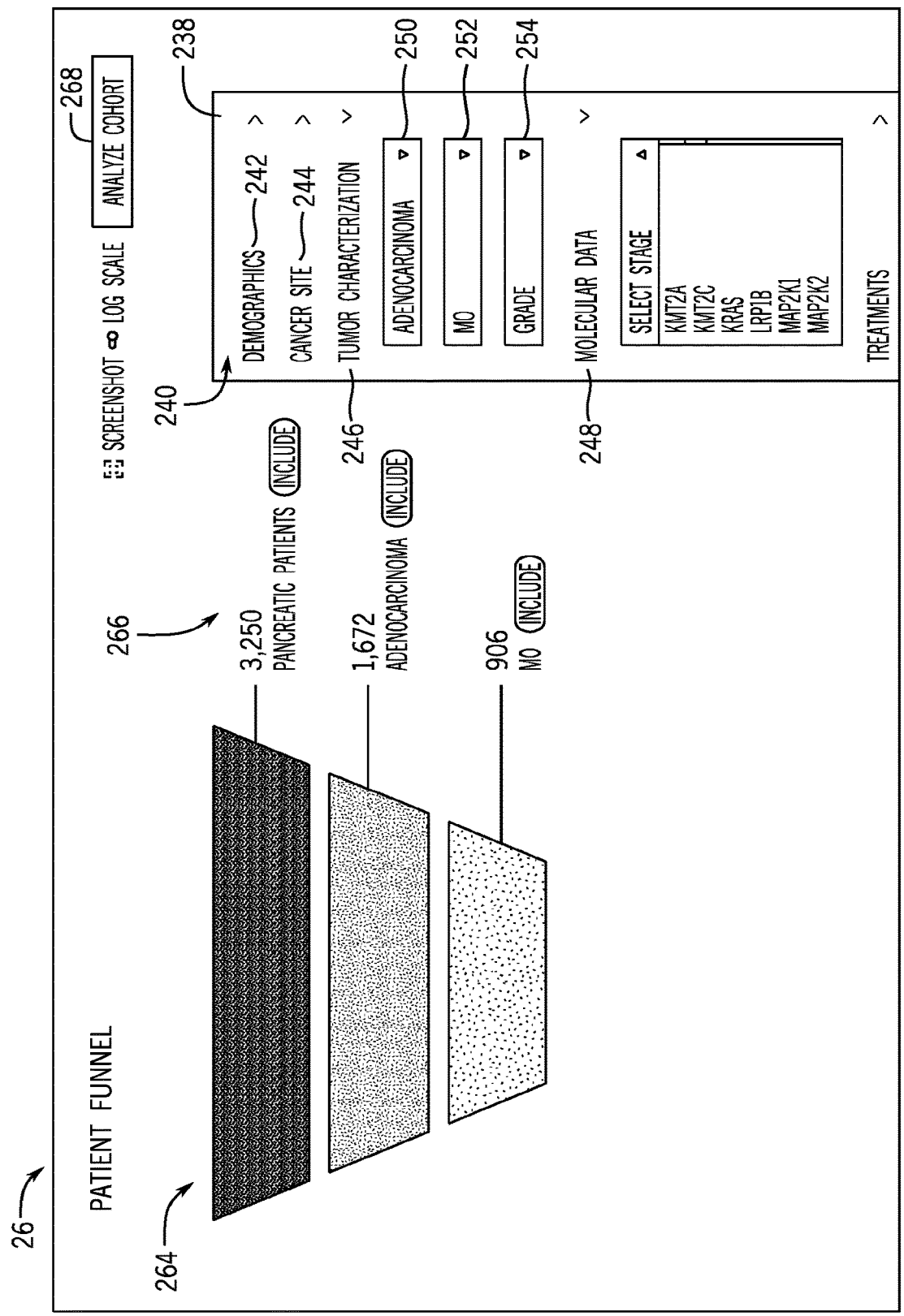
FIG. 8 is another example of a cohort funnel & population analysis user interface.
Figure 9:
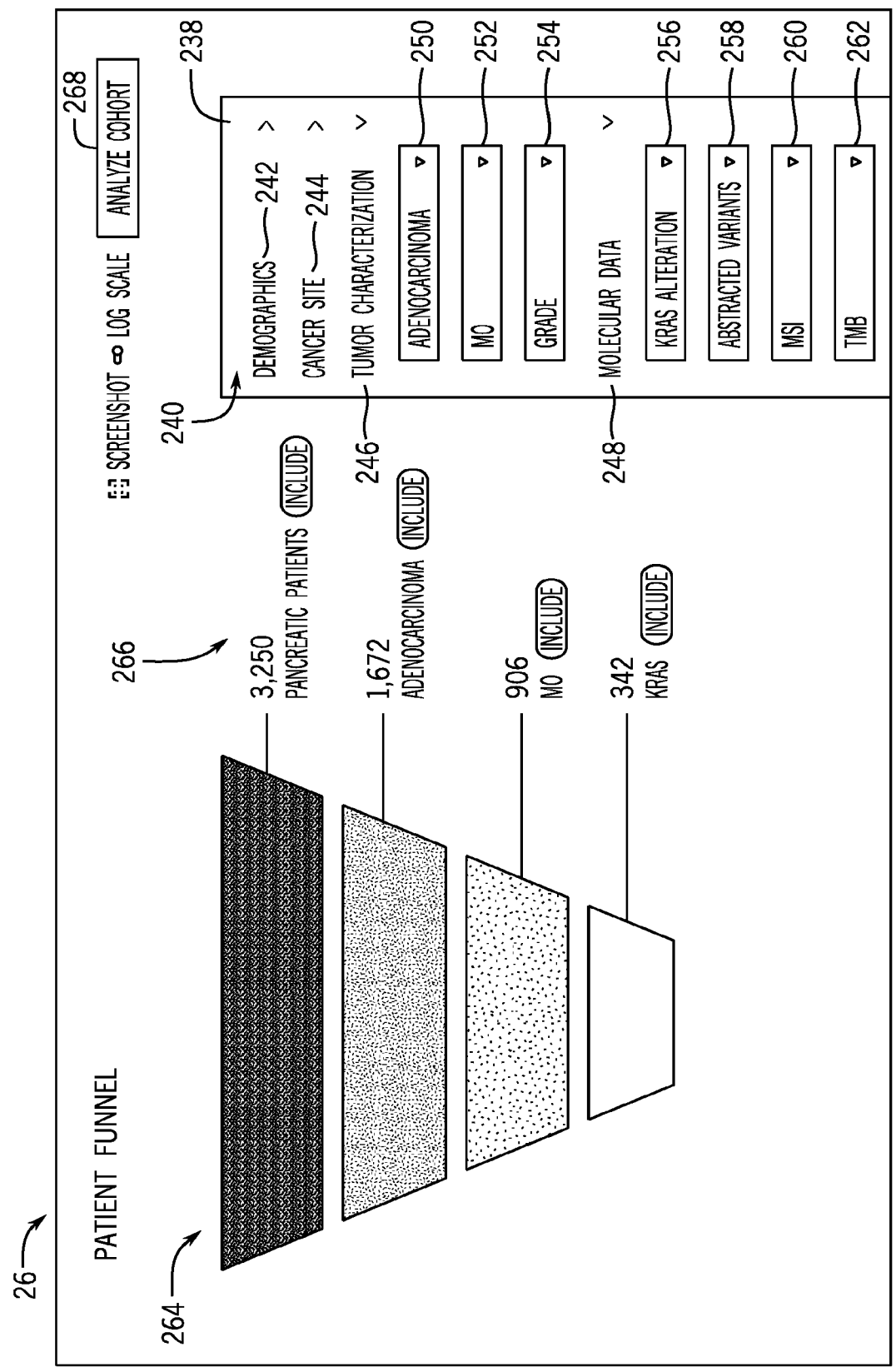
FIG. 9 is another example of a cohort funnel & population analysis user interface.

With reference to the accompanying figures, and particularly with reference to FIG. 1, a system 10 for predicting and analyzing patient cohort response, progression, and survival may include a back end layer 12 that includes a patient data store 14 accessible by a patient cohort selector module 16 in communication with a patient cohort timeline data storage 18. The patient cohort selector module 16 interacts with a front end layer 20 that includes an interactive analysis portal 22 that may be implemented, in one instance, via a web browser to allow for on-demand filtering and analysis of the data store 14.

The interactive analysis portal 22 may include a plurality of user interfaces including an interactive cohort selection filtering interface 24 that, as discussed in greater detail below, permits a user to query and filter elements of the data store 14. As discussed in greater detail below, the portal 22 also may include a cohort funnel and population analysis interface 26, a patient timeline analysis user interface 28, a patient survival analysis user interface 30, and a patient event likelihood analysis user interface 32. The portal 22 further may include a patient next analysis user interface 34 and one or more patient future analysis user interfaces 36.

Returning to FIG. 1, the back end layer 12 also may include a distributed computing and modeling layer 38 that receives data from the patient cohort timeline data storage 18 to provide inputs to a plurality of modules, including, a time to event modeling module 40 that powers the patient survival analysis user interface 30, an event likelihood module 42 that calculates the likelihood of one or more events received at the patient event likelihood analysis user interface 32 for subsequent display in that user interface, a next event modeling module 44 that generates models of one or more next events for subsequent display at the patient next event analysis user interface 34, and one or more future modeling modules 46 that generate one or more future models for subsequent display at the one or more patient future analysis user interfaces 36.

The patient data store 14 may be a pre-existing dataset that includes patient clinical history, such as demographics, comorbidities, diagnoses and recurrences, medications, surgeries, and other treatments along with their response and adverse effects details. The Patient Data Store may also include patient genetic/molecular sequencing and genetic mutation details relating to the patient, as well as organoid modeling results. In one aspect, these datasets may be generated from one or more sources. For example, institutions implementing the system may be able to draw from all of their records; for example, all records from all doctors and/or patients connected with the institution may be available to the institutions agents, physicians, research, or other authorized members. Similarly, doctors may be able to draw from all of their records; for example, records for all of their patients. Alternatively, certain system users may be able to buy or license aspect to the datasets, such as when those users do not have immediate access to a sufficiently robust dataset, when those users are looking for even more records, and/or when those users are looking for specific data types, such as data reflecting patients having certain primary cancers, metastases by origin site and/or diagnosis site, recurrences by origin, metastases, or diagnosis sites, etc.

Features and Feature Modules

A patient data store may include one or more feature modules which may comprise a collection of features available for every patient in the system 10. These features may be used to generate and model the artificial intelligence classifiers in the system 10. While feature scope across all patients is informationally dense, a patient's feature set may be sparsely populated across the entirety of the collective feature scope of all features across all patients. For example, the feature scope across all patients may expand into the tens of thousands of features while a patient's unique feature set may only include a subset of hundreds or thousands of the collective feature scope based upon the records available for that patient.

Feature collections may include a diverse set of fields available within patient health records. Clinical information may be based upon fields which have been entered into an electronic medical record (EMR) or an electronic health record (EHR) by a physician, nurse, or other medical professional or representative. Other clinical information may be curated from other sources, such as molecular fields from genetic sequencing reports. Sequencing may include next-generation sequencing (NGS) and may be long-read, short-read, or other forms of sequencing a patient's somatic and/or normal genome. A comprehensive collection of features in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from an RNA feature module or a DNA feature module sequencing.

Another subset of features, imaging features from imaging feature module, may comprise features identified through review of a specimen through pathologist review, such as a review of stained H&E or IHC slides. As another example, a subset of features may comprise derivative features obtained from the analysis of the individual and combined results of such feature sets. Features derived from DNA and RNA sequencing may include genetic variants from variant science module which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology features.

Features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates to any of the above.

Features may be derived from information from additional medical or research based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features derived from imaging data may further include reports associated with a stained slide, size of tumor, tumor size differentials over time including treatments during the period of change, as well as machine learning approaches for classifying PDL1 status, HLA status, or other characteristics from imaging data. Other features may include the additional derivative features sets from other machine learning approaches based at least in part on combinations of any new features and/or those listed above. For example, imaging results may need to be combined with MSI calculations derived from RNA expressions to determine additional further imaging features. In another example a machine learning model may generate a likelihood that a patient's cancer will metastasize to a particular organ or a patient's future probability of metastasis to yet another organ in the body. Other features that may be extracted from medical information may also be used. There are many thousands of features, and the above listing of types of features are merely representative and should not be construed as a complete listing of features.

An alteration module may be one or more microservices, servers, scripts, or other executable algorithms which generate alteration features associated with de-identified patient features from the feature collection. Alterations modules may retrieve inputs from the feature collection and may provide alterations for storage. Exemplary alterations modules may include one or more of the following alterations as a collection of alteration modules. A SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in our susceptibility to a wide range of diseases (e.g. -sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10 000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides. CNV are the phenomenon in which structural variations may occur in sections of nucleotides, or base pairs, that include repetitions, deletions, or inversions. A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer.

BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer. An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualising an antibody-antigen interaction can be accomplished in a number of ways. In the most common instance, an antibody is conjugated to an enzyme, such as peroxidase, that can catalyse a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. A Therapies module may identify differences in cancer cells (or other cells near them) that help them grow and thrive and drugs that "target" these differences. Treatment with these drugs is called targeted therapy. For example, many targeted drugs go after the cancer cells' inner 'programming' that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause. Matching targeted therapies may include identifying the therapy targets in the patients and satisfying any other inclusion or exclusion criteria. A VUS (variant of unknown significance) module may identify variants which are called but cannot be classify as pathogenic or benign at the time of calling. VUS may be catalogued from publications regarding a VUS to identify if they may be classified as benign or pathogenic. A Trial module may identify and test hypotheses for treating cancers having specific characteristics by matching features of a patient to clinical trials. These trials have inclusion and exclusion criteria that must be matched to enroll which may be ingested and structured from publications, trial reports, or other documentation. An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another. An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms. A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification may include evaluating features from the feature collection, alterations from the alteration module, and other classifications from within itself from one or more classification modules. Structural variant classification may provide classifications to a stored classifications storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules. A classifier for clinical trials may include evaluation of variants identified from the alteration module which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules.

Each of the feature collection, alteration module(s), structural variant and feature store may be communicatively coupled to a data bus to transfer data between each module for processing and/or storage. In another embodiment, each of the feature collection, alteration module(s), structural variant and feature store may be communicatively coupled to each other for independent communication without sharing the data bus.

In addition to the above features and enumerated modules, feature modules may further include one or more of the following modules within their respective modules as a sub-module or as a standalone module.

Germline/somatic DNA feature module may comprise a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module may comprise a feature collection associated with the RNA-derived information of a patient, such as transcriptome information. These features may include raw sequencing results, transcriptome expressions, genes, mutations, variant calls, and variant characterizations.

A metadata module may comprise a feature collection associated with the human genome, protein structures and their effects, such as changes in energy stability based on a protein structure.

A clinical module may comprise a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module may comprise a feature collection associated with information derived from imaging records of a patient. Imaging records may include H&E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as epigenome module from Omics, may comprise a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as microbiome module from Omics, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as proteome module from Omics, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) may also be included in Omics, such as a feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

A feature set for DNA related (molecular) features may include a proprietary calculation of the maximum effect a gene may have from sequencing results for the following genes: ABCB1-somatic, ACTA2-germline, ACTC1-germline, ALK-fluorescence_in_situ_hybridization_(fish), ALK-immunohistochemistry_(ihc), ALK-md_dictated, ALK-somatic, AMER1-somatic, APC-gene_mutation_analysis, APC-germline, APC-somatic, APOB-germline, APOB-somatic, AR-somatic, ARHGAP35-somatic, ARID1A-somatic, ARID1B-somatic, ARID2-somatic, ASXL1-somatic, ATM-gene_mutation_analysis, ATM-germline, ATM-somatic, ATP7B-germline, ATR-somatic, ATRX-somatic, AXIN2-germline, BACH1-germline, BCL11B-somatic, BCLAF1-somatic, BCOR-somatic, BCORL1-somatic, BCR-somatic, BMPR1A-germline, BRAF-gene_mutation_analysis, BRAF-md_dictated, BRAF-somatic, BRCA1-germline, BRCA1-somatic, BRCA2-germline, BRCA2-somatic, BRD4-somatic, BRIP1-germline, CACNA1S-germline, CARD11-somatic, CASR-somatic, CD274-immunohistochemistry_(ihc), CD274-md_dictated, CDH1-germline, CDH1-somatic, CDK12-germline, CDKN2A-immunohistochemistry_(ihc), CDKN2A-germline, CDKN2A-somatic, CEBPA-germline, CEBPA-somatic, CFTR-somatic, CHD2-somatic, CHD4-somatic, CHEK2-germline, CIC-somatic, COL3A1-germline, CREBBP-somatic, CTNNB1-somatic, CUX1-somatic, DICER1-somatic, DOT1L-somatic, DPYD-somatic, DSC2-germline, DSG2-germline, DSP-germline, DYNC2H1-somatic, EGFR-gene_mutation_analysis, EGFR-immunohistochemistry_(ihc), EGFR-md_dictated, EGFR-germline, EGFR-somatic, EP300-somatic, EPCAM-germline, EPHA2-somatic, EPHA7-somatic, EPHB1-somatic, ERBB2-fluorescence_in_situ_hybridization_(fish), ERBB2-immunohistochemistry_(ihc), ERBB2-md_dictated, ERBB2-somatic, ERBB3-somatic, ERBB4-somatic, ESR1-immunohistochemistry_(ihc), ESR1-somatic, ETV6-germline, FANCA-germline, FANCA-somatic, FANCD2-germline, FANCI-germline, FANCL-germline, FANCM-somatic, FAT1-somatic, FBN1-germline, FBXW7-somatic, FGFR3-somatic, FH-germline, FLCN-germline, FLG-somatic, FLT1-somatic, FLT4-somatic, GATA2-germline, GATA3-somatic, GATA4-somatic, GATA6-somatic, GLA-germline, GNAS-somatic, GRIN2A-somatic, GRM3-somatic, HDAC4-somatic, HGF-somatic, IDH1-somatic, IKZF1-somatic, IRS2-somatic, JAK3-somatic, KCNH2-germline, KCNQ1-germline, KDM5A-somatic, KDM5C-somatic, KDM6A-somatic, KDR-somatic, KEAP1-somatic, KEL-somatic, KIF1B-somatic, KMT2A-fluorescence_in_situ_hybridization_(fish), KMT2A-somatic, KMT2B-somatic, KMT2C-somatic, KMT2D-somatic, KRAS-gene_mutation_analysis, KRAS-md_dictated, KRAS-somatic, LDLR-germline, LMNA-germline, LRP1B-somatic, MAP3K1-somatic, MED12-somatic, MEN1-germline, MET-fluorescence_in_situ_hybridization_(fish), MET-somatic, MKI67-immunohistochemistry_(ihc), MKI67-somatic, MLH1-germline, MSH2-germline, MSH3-germline, MSH6-germline, MSH6-somatic, MTOR-somatic, MUTYH-germline, MYBPC3-germline, MYCN-somatic, MYH11-germline, MYH11-somatic, MYH7-germline, MYL2-germline, MYL3-germline, NBN-germline, NCOR1-somatic, NCOR2-somatic, NF1-somatic, NF2-germline, NOTCH1-somatic, NOTCH2-somatic, NOTCH3-somatic, NRG1-somatic, NSD1-somatic, NTRK1-somatic, NTRK3-somatic, NUP98-somatic, OTC-germline, PALB2-germline, PALLD-somatic, PBRM1-somatic, PCSK9-germline, PDGFRA-somatic, PDGFRB-somatic, PGR-immunohistochemistry_(ihc), PIK3C2B-somatic, PIK3CA-somatic, PIK3CG-somatic, PIK3R1-somatic, PIK3R2-somatic, PKP2-germline, PLCG2-somatic, PML-somatic, PMS2-germline, POLD1-germline, POLD1-somatic, POLE-germline, POLE-somatic, PREX2-somatic, PRKAG2-germline, PTCH1-somatic, PTEN-fluorescence_in_situ_hybridization_(fish), PTEN-gene_mutation_analysis, PTEN-germline, PTEN-somatic, PTPN13-somatic, PTPRD-somatic, RAD51B-germline, RAD51C-germline, RAD51D-germline, RAD52-germline, RAD54L-germline, RANBP2-somatic, RB1-germline, RB1-somatic, RBM10-somatic, RECQL4-somatic, RET-fluorescence_in_situ_hybridization_(fish), RET-germline, RET-somatic, RICTOR-somatic, RNF43-somatic, ROS1-fluorescence_in_situ_hybridization_(fish), ROS1-md_dictated, ROS1-somatic, RPTOR-somatic, RUNX1-germline, RUNX1T1-somatic, RYR1-germline, RYR2-germline, SCN5A-germline, SDHAF2-germline, SDHB-germline, SDHC-germline, SDHD-germline, SETBP1-somatic, SETD2-somatic, SH2B3-somatic, SLIT2-somatic, SLX4-somatic, SMAD3-germline, SMAD4-germline, SMAD4-somatic, SMARCA4-somatic, SOX9-somatic, SPEN-somatic, STAG2-somatic, STK11-gene_mutation_analysis, STK11-germline, STK11-somatic, TAF1-somatic, TBX3-somatic, TCF7L2-somatic, TERT-somatic, TET2-somatic, TGFBR1-germline, TGFBR2-germline, TGFBR2-somatic, TMEM43-germline, TNNI3-germline, TNNT2-germline, TP53-gene_mutation_analysis, TP53-immunohistochemistry_(ihc), TP53-md_dictated, TP53-germline, TP53-somatic, TPM1-germline, TSC1-germline, TSC1-somatic, TSC2-germline, TSC2-somatic, VHL-germline, WT1-germline, WT1-somatic, XRCC3-germline, and ZFHX3-somatic.

A sufficiently robust collection of features may include all of the features disclosed above; however, models and predictions based from the available features may include models which are optimized and trained from a selection of features that are much more limiting than the exhaustive feature set. Such a constrained feature set may include as few as tens to hundreds of features. For example, a model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

A feature store may enhance a patient's feature set through the application of machine learning and analytics by selecting from any features, alterations, or calculated output derived from the patient's features or alterations to those features. Such a feature store may generate new features from the original features found in feature module or may identify and store important insights or analysis based upon the features. The selections of features may be based upon an alteration or calculation to be generated, and may include the calculation of single or multiple nucleotide polymorphisms insertion or deletions of the genome, a tumor mutational burden, a microsatellite instability, a copy number variation, a fusion, or other such calculations. An exemplary output of an alteration or calculation generated which may inform future alterations or calculations includes a finding of hypertrophic cardiomyopathy (HCM) and variants in MYH7. Wherein previous classified variants may be identified in the patient's genome which may inform the classification of novel variants or indicate a further risk of disease. An exemplary approach may include the enrichment of variants and their respective classifications to identify a region in MYH7 that is associated with HCM. Any novel variants detected from a patient's sequencing localized to this region would increase the patient's risk for HCM. Features which may be utilized in such an alteration detection include the structure of MYH7 and classification of variants therein. A model which focuses on enrichment may isolate such variants.

Artificial Intelligence Models

Artificial intelligence models referenced herein may be gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

A set of transformation steps may be performed to convert the data from the Patient Data Store into a format suitable for analysis. Various modern machine learning algorithms may be utilized to train models targeting the prediction of expected survival and/or response for a particular patient population. An exemplary data store 14 is described in further detail in U.S. Provisional Patent Application No. 62/746,997, titled "Data Based Cancer Research and Treatment Systems and Methods," filed Oct. 17, 2018; U.S. patent application Ser. No. 16/289,027, titled "Mobile Supplementation, Extraction, and Analysis of Health Records" and filed Feb. 28, 2019, and issued Aug. 27, 2019, as U.S. Pat. No. 10,395,772; and PCT International Application No. PCT/US19/56713 filed Oct. 17, 2019 and titled "Data Based Cancer Research and Treatment Systems and Methods," each of which is incorporated herein by reference in its entirety.

The system may include a data delivery pipeline to transmit clinical and molecular de-identified records in bulk. The system also may include separate storage for de-identified and identified data to maintain data privacy and compliance with applicable laws or guidelines, such as the Health Insurance Portability and Accountability Act.

The raw input data and/or any transformed, normalized, and/or predictive data may be stored in one or more relational databases for further access by the system in order to carry out one or more comparative or analytical functions, as described in greater detail herein. The data model used to construct the relational database(s) may be used to store, organize, display, and/or interpret a significant amount and variety of data, e.g., dozens of tables that comprise hundreds of different columns. Unlike standard data models such as OMOP or QDM, the data model may generate unique linkages within a table or across tables to directly relate various clinical attributes, thereby making complex clinical attributes easier to ingest, interpret and analyze.

Once the relevant data has been received, transformed, and manipulated, as discussed above, the system may include a plurality of modules in order to generate the desired dynamic user interfaces, as discussed above with regard to the system diagram of FIG. 1.

Patient Cohort Filtering User Interface

Turning to FIG. 2, a first embodiment of a patient cohort selection filtering interface 24 may be provided as a side pane 200 provided along a height (or, alternatively, a length) of a display screen, through which attribute criteria 202 (such as clinical, molecular, demographic etc.) can be specified by the user, defining a patient population of interest for further analysis. The side pane 200 may be hidden or expanded by selecting it, dragging it, double-clicking it, etc.

Additionally, or alternatively, the system may recognize one or more attributes defined for tumor data stored by the system, where those attributes may be, for example, genotypic, phenotypic, genealogical, or demographic. The various selectable attribute criteria may reflect patient-related metadata stored in the patient data store 14, where exemplary metadata may include, for instance: Project Name (which may reflect a database storing a list of patients) 204, Gender 206, Race 208; Cancer, Cancer Site 210, Cancer Name 212; Metastasis, Cancer Name 214; Tumor Site 216 (which may reflect where the tumor was located), Stage 218 (such as I, II, III, IV, and unknown), M Stage 220 (such as m0, m1, m2, m3, and unknown); Medication (such as by Name 222 or Ingredient 224); Sequencing 226 (such as gene name or variant), MSI (Microsatellite Instability) status 228, TMB (Tumor Mutational Burden) status (not shown); Procedure 230 (such as, by Name); or Death (such as, by Event Name 232 or Cause of Death 234).

The system also may permit a user to filter patient data according to any of the criteria listed herein including those listed under the heading "Features and Feature Modules," and include one or more of the following additional criteria: institution, demographics, molecular data, assessments, diagnosis site, tumor characterization, treatment, or one or more internal criteria. The institution option may permit a user to filter according to a specific facility. The demographics option may permit a user to sort, for example, by one or more of gender, death status, age at initial diagnosis, or race. The molecular data option may permit a user to filter according to variant calls (for example, when there is molecular data available for the patient, what the particular gene name, mutation, mutation effect, and/or sample type is), abstracted variants (including, for example, gene name and/or sequencing method), MSI status (for example, stable, low, or high), or TMB status (for example, selectable within or outside of a user-defined ranges). Assessments may permit a user to filter according to various system-defined criteria such as smoking status and/or menopausal status. Diagnosis site may permit a user to filter according to primary and/or metastatic sites. Tumor characterization may permit the user to filter according to one or more tumor-related criteria, for example, grade, histology, stage, TNM Classification of Malignant Tumours (TNM) and/or each respective T value, N value, and/or M value. Treatment may permit the user to select from among various treatment-related options, including, for instance, an ingredient, a regimen, a treatment type, etc.

Certain criteria may permit the user to select from a plurality of sub-criteria that may be indicated once the initial criteria is selected. Other criteria may present the user with a binary option, for example, deceased or not. Still other criteria may present the user with slider or range-type options, for example, age at initial diagnosis may be presented as a slider with user-selectable lower and upper bounds. Still further, for any of these options, the system may present the user with a radio button or slider to alternate between whether the system should include or exclude patients based on the selected criterion. It should be understood that the examples described herein do not limit the scope of the types of information that may be used as criteria. Any type of medical information capable of being stored in a structured format may be used as a criteria.

In another embodiment, the user interface may include a natural language search style bar to facilitate filter criteria definition for the cohort, for example, in the "Ask Gene" tab 236 of the user interface or via a text input of the filtering interface. In one aspect, an ability to specify a query, either via keyboard-type input or via machine-interpreted dictation, may define one or more of the subsequent layers of a cohort funnel (described in greater detail in the next section). Thus, for example, when employing traditional natural language processing software or techniques, an input of "breast cancer patients" would cause the system to recognize a filter of "cancer_site==breast cancer" and add that as the next layer of filtering. Similarly, the system would recognize an input of "pancreatic patients with adverse reactions to gemcitabine" and translate it into multiple successive layers of filtering, for example, "cancer_site==pancreatic cancer" AND "medication==gemcitabine" AND "adverse reaction==not null."

In a second aspect, the natural language processing may permit a user to use the system to query for general insights directly, thereby both narrowing down a cohort of patients via one or more funnel levels and also causing the system to display an appropriate summary panel in the user interface. Thus, in the situation that the system receives the query "What is the 5 years progression-free survival rate for stage III colorectal cancer patients, after radiotherapy?," it would translate it into a series of filters such as "cancer site==colorectal" AND "stage==III" AND "treatment==radiotherapy" and then display five-year progression-free survival rates using, for example, the patient survival analysis user interface 30. Similarly, the query "What percentage of female lung cancer patients are post-menopausal at a time of diagnosis?" would translate it into a series of patients such as "gender==female," "cancer_site lung," and "temporal==at diagnosis," determine how many of the resulting patients had data reflecting a post-menopause situation, and then determine the relevant percentage, for example, displaying the results through one or more statistical summary charts.

Cohort Funnel and Population Analysis User Interface

Turning now to FIGS. 3-9, the cohort funnel and population analysis user interface 26 may be configured to permit a user to conduct analysis of a cohort, for the purpose of identifying key inflection points in the distribution of patients exhibiting each attribute of interest, relative to the distributions in the general patient population or a patient population whose data is stored in the patient data store 14. In one aspect, the filtering and selection of additional patient-related criteria discussed above with regard to FIG. 2 may be used in connection with the cohort funnel and population analysis user interface 26.

In another embodiment, the system may include a selectable button or icon that opens a dialogue box 238 which shows a plurality of selectable tabs, each tab representing the same or similar filtering criteria discussed above (Demographics, Molecular Data, Assessments, Diagnosis Site, Tumor Characterization, and Treatment). Selection of each tab may present the user with the same or similar options for each respective filter as discussed above (for example, selecting "Demographics" may present the user with further options relating to: Gender, Death Status, Age at Initial Diagnosis, or Race). The user then may select one or more options, select "next," and then select whether it is an inclusion or exclusion filter, and the corresponding selection is added to the funnel (discussed in greater detail below), with an icon moving to be below a next successively narrower portion of the funnel.

Additionally, or alternatively, looking at the cohort, or set of patients in a database, the system permits filtering by a plurality of clinical and molecular factors via a menu 240. For example, and with regard to clinical factors, the system may include filters based on patient demographics 242, cancer site 244, tumor characterization 246, or molecular data 248 which further may include their own subsets of filterable options 242, such as histology 250, stage 252, and/or grade-based options 254 (see FIG. 4) for tumor characterization. With regard to molecular factors, the system may permit filtering according to variant calls 256, abstracted variants 258, MSI 260, and/or TMB 262.

Although the examples discussed herein provide analysis with regard to various cancer types, in other embodiments, it will be appreciated that the system may be used to indicate filtered display of other disease conditions, and it should be understood that the selection items will differ in those situations to focus particularly on the relevant conditions for the other disease.

The cohort funnel and population analysis user interface 26 visually may depict the number of patients in the data set, either all at once or progressively upon receiving a user's selection of multiple filtering criteria. In one aspect, the display of patient frequencies by filter attribute may be provided using an interactive funnel chart 264. As seen in FIGS. 3-9, with each selection, the user interface 26 updates to illustrate the reduction in results matching the filter criteria; for example, as more filter criteria are added, fewer patients matching all of the selected criteria exist, upon receiving each of a user's filtering factors.

The above filtering can be performed upon receiving each user selection of a filter criterion, the funnel 264 updating to show the narrowing span of the dataset upon each filter selection. In that situation a filtering menu 240 such as the one discussed above may remain visible in each tab as they are toggled, or may be collapsed to the side, or may be represented as a summary 266 of the selected filtered options to keep the user apprised of the reduced data set/size.

With regard to each filtering method discussed above, the combination of factors may be based on Boolean-style combinations. Exemplary Boolean-style combinations may include, for filtering factors A and B, permitting the user to select whether to search for patients with "A AND B," "A OR B," "A AND NOT B," "B AND NOT A," etc.

The final filtered cohort of interest may form the basis for further detailed analysis in the modules or other user interfaces described below. The population of interest is called a "cohort". The user interface can provide fixed functional attribute selectors pre-populated appropriately based on the available data attributes in a Patient Data Store.

The display may further indicate a geographic location clustering plot of patients and/or demographic distribution comparisons with publicly reported statistics and/or privately curated statistics.

Patient Timeline Analysis Module

Additionally, the system may include a patient timeline analysis module 28 that permits a user to review the sequence of events in the clinical life of each patient. It will be appreciated that this data may be anonymized, as discussed above, in order to protect confidentiality of the patient data.

Once a user has provided all of his or her desired filter criteria, e.g., via the cohort funnel & population analysis user interface 26, the system permits the user to analyze the filtered subset of patients. With respect to the user interface depicted in the figures, this procedure may be accomplished by selecting the "Analyze Cohort" option 268 presented in the upper right-hand corner of the interface 26.

Figure 10:
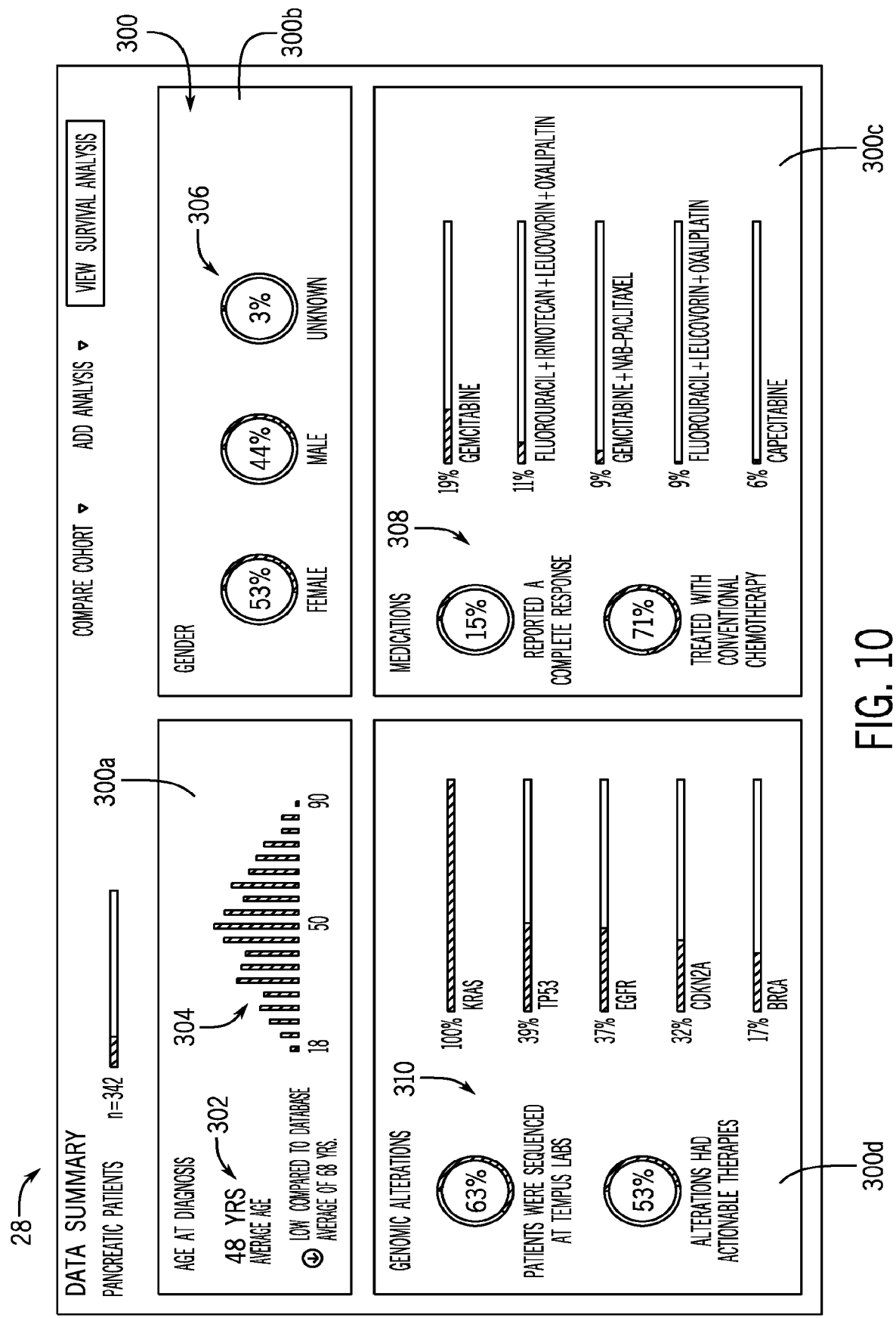
FIG. 10 is one example of a data summary window in a patient timeline analysis user interface.

Turning now to FIG. 10, after requesting analysis of the filtered subset of patients, the user interface may generate a data summary window in the patient timeline analysis user interface 28, with one or more regions 300 providing information about the selected patient subset, for example, a number of other distributions across clinical and molecular features. In one aspect, a first region 300*a* may include demographic information such as an average patient age 302 and/or a plot of patient ages 304. A second region 300*b* may include additional demographic information, such as gender information 306, for the subset of patients. A third region 300*c* may include a summary of certain clinical data, including, for example, an analysis of the medications 308 taken by each of the patients in the subset. Similarly, a fourth region 300*d* may include molecular data about each of the patients, for example, a breakdown of each genomic variant or alteration 310 possessed by the patients in the subset.

Figure 11:
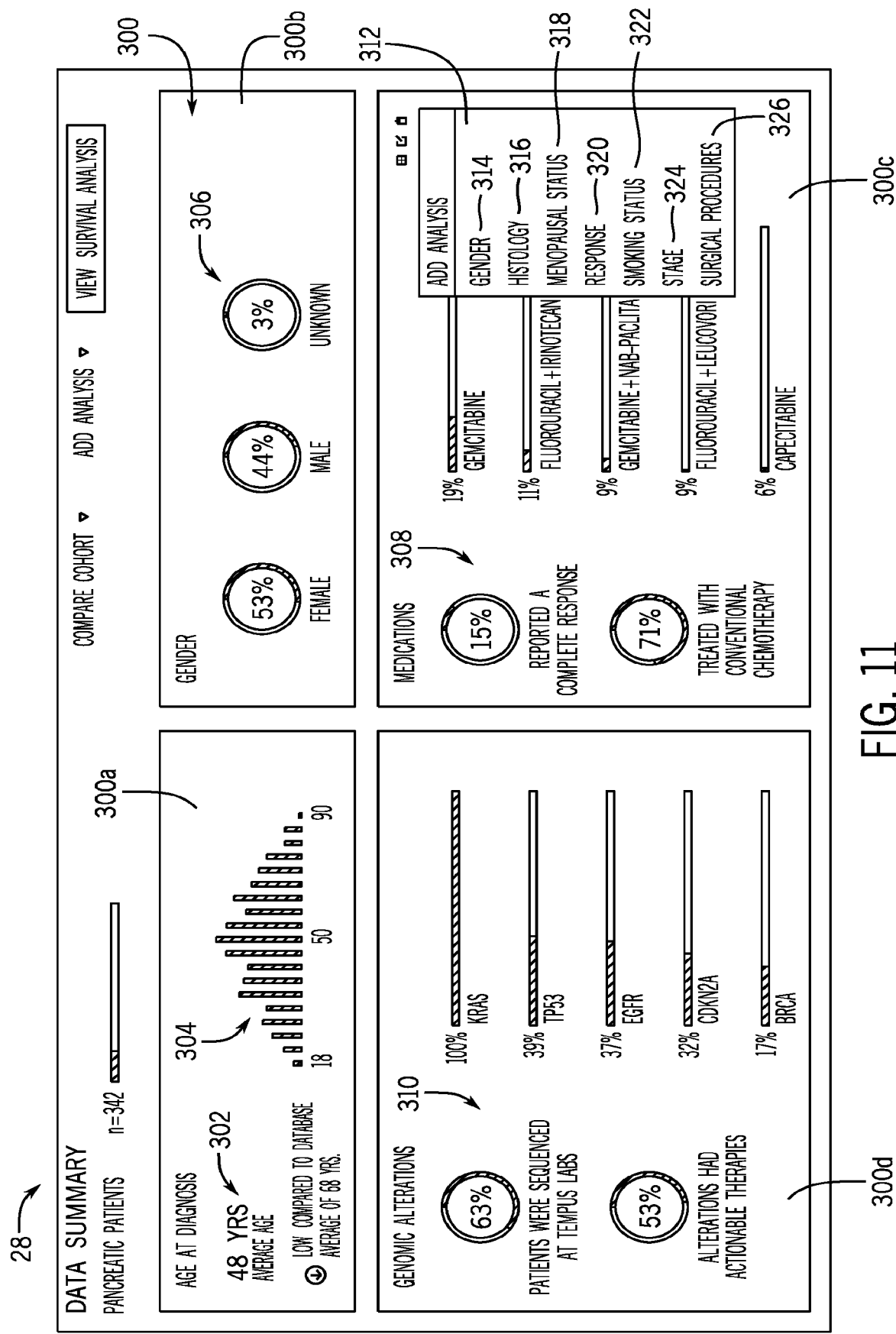
FIG. 11 is another example of a data summary window in a patient timeline analysis user interface.
Figure 12:
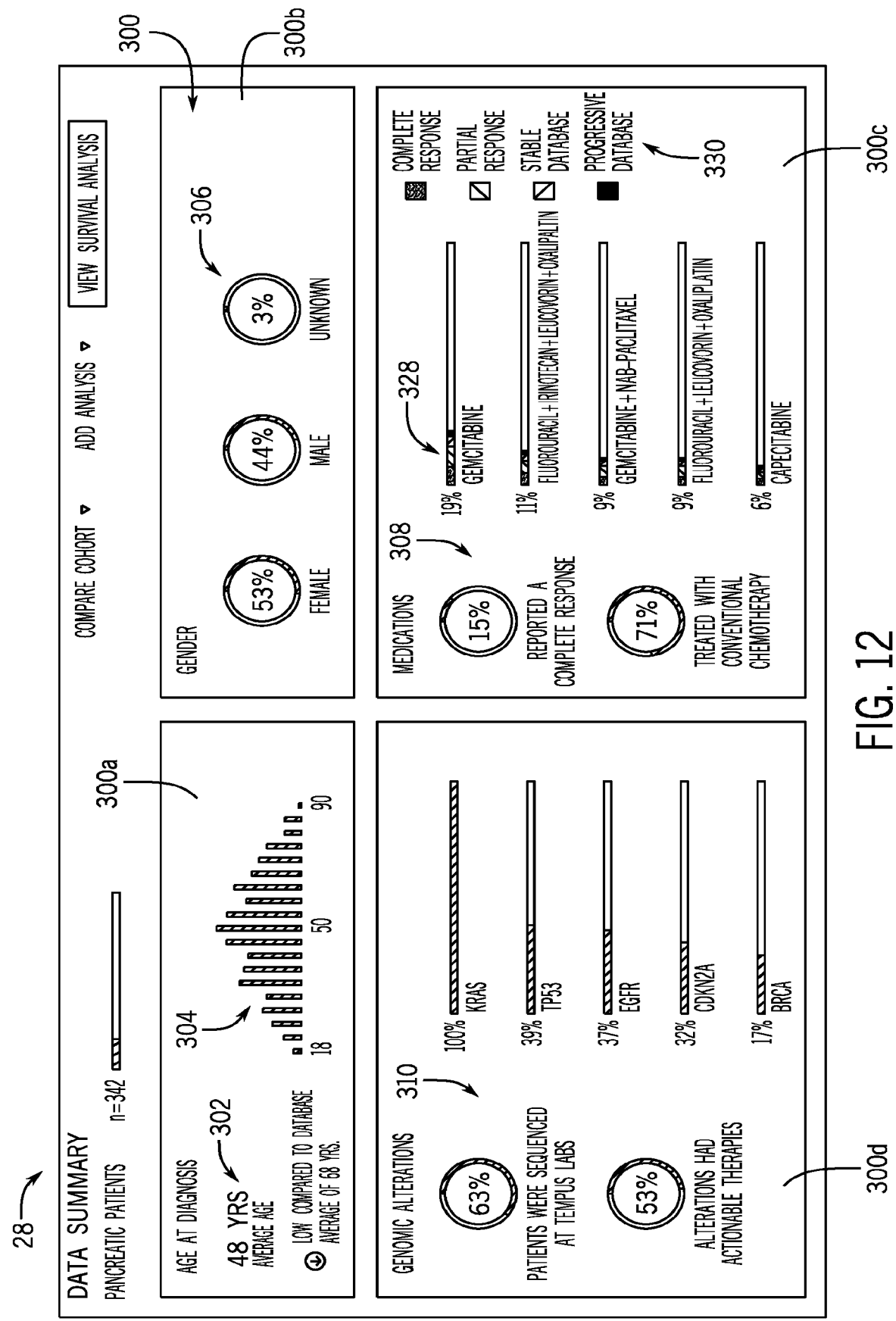
FIG. 12 is another example of a data summary window in a patient timeline analysis user interface.

The user interface 28 also permits a user to query the data summary information presented in the data summary window or region 300 in order to sort that data further, e.g., using a control panel 312. For example, as seen in FIGS. 11-14, the system may be configured to sort the patient data based on one or more factors including, for example, gender 314, histology 316, menopausal status 318, response 320, smoking status 322, stage 324, and surgical procedures 326. Selecting one or more of these options may not reduce the sample size of patients, as was the case above when discussing filtering being summarized in the data summary window. Instead, the sort functions may subdivide the summarized information into one or more subcategories. For example, FIGS. 11 and 12 depict medication information 308 being sorted by having additional response data 328 layered over it within the data summary window 300*c*, along with a legend 330 explaining the layered response data.

Figure 13:
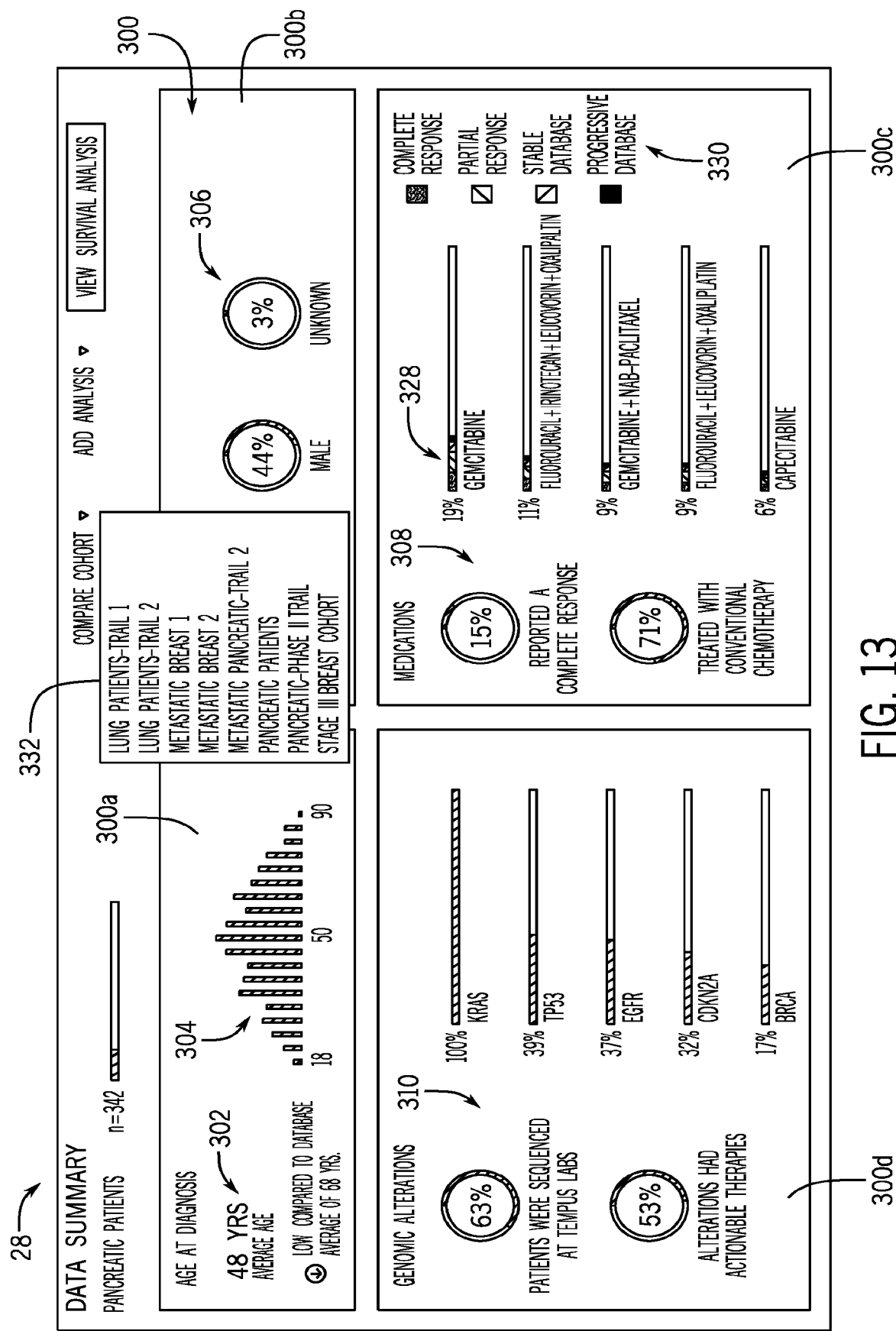
FIG. 13 is another example of a data summary window in a patient timeline analysis user interface.
Figure 14:
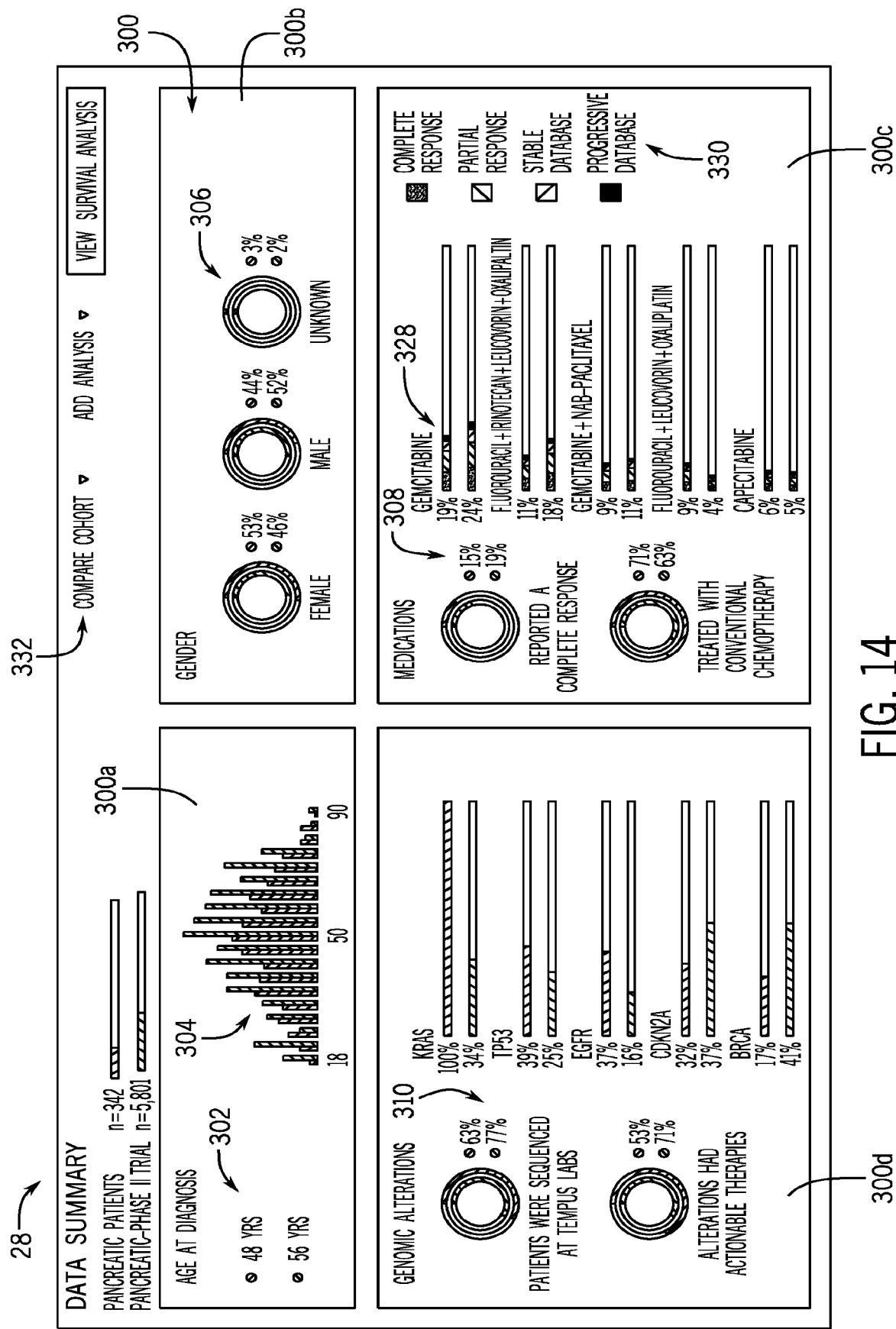
FIG. 14 is another example of a data summary window in a patient timeline analysis user interface.

Turning now to FIGS. 13-14, the subset of patients selected by the user also may be compared against a second subset (or "cohort") of patients, e.g., via a drop-down menu 332, thereby facilitating a side-by-side analysis of the groups. Doing so may permit the user to quickly and easily see any similarities, as well as any noticeable differences, between the subsets.

In one embodiment, an event timeline Gantt style chart is provided for a high-level overview, coupled with a tabular detail panel. The display may also enable the visualization and comparison of multiple patients concurrently on a normalized timeline, for the purposes of identifying both areas of overlap, and potential discontinuity across a patient subset.

Patient "Survival" Analysis Module

The system further may provide survival analysis for the subset of patients through use of the patient survival analysis user interface 30, as seen in FIGS. 15-20. This modeling and visualization component may enable the user to interactively explore time until event (and probability at time) curves and their confidence intervals, for sub-groups of the filtered cohort of interest. The time series inception and target events can be selected and dynamically modified by the user, along with attributes on which to cluster patient groups within the chosen population, all while the curve visualizer reactively adapts to the provided parameters.

In order to provide the user with flexibility to define the metes and bounds of that analysis, the system may permit the user to select one or both of the starting and ending events upon which that analysis is based. Exemplary starting events include an initial primary disease diagnosis, progression, metastasis, regression, identification of a first primary cancer, an initial prescription of medication, etc. Conversely, exemplary ending events may include progression, metastasis, recurrence, death, a period of time, and treatment start/end dates. Selecting a starting event sets an anchor point for all patients from which the curve begins, and selecting an end event sets a horizon for which the curve is predicting.

Figure 15:
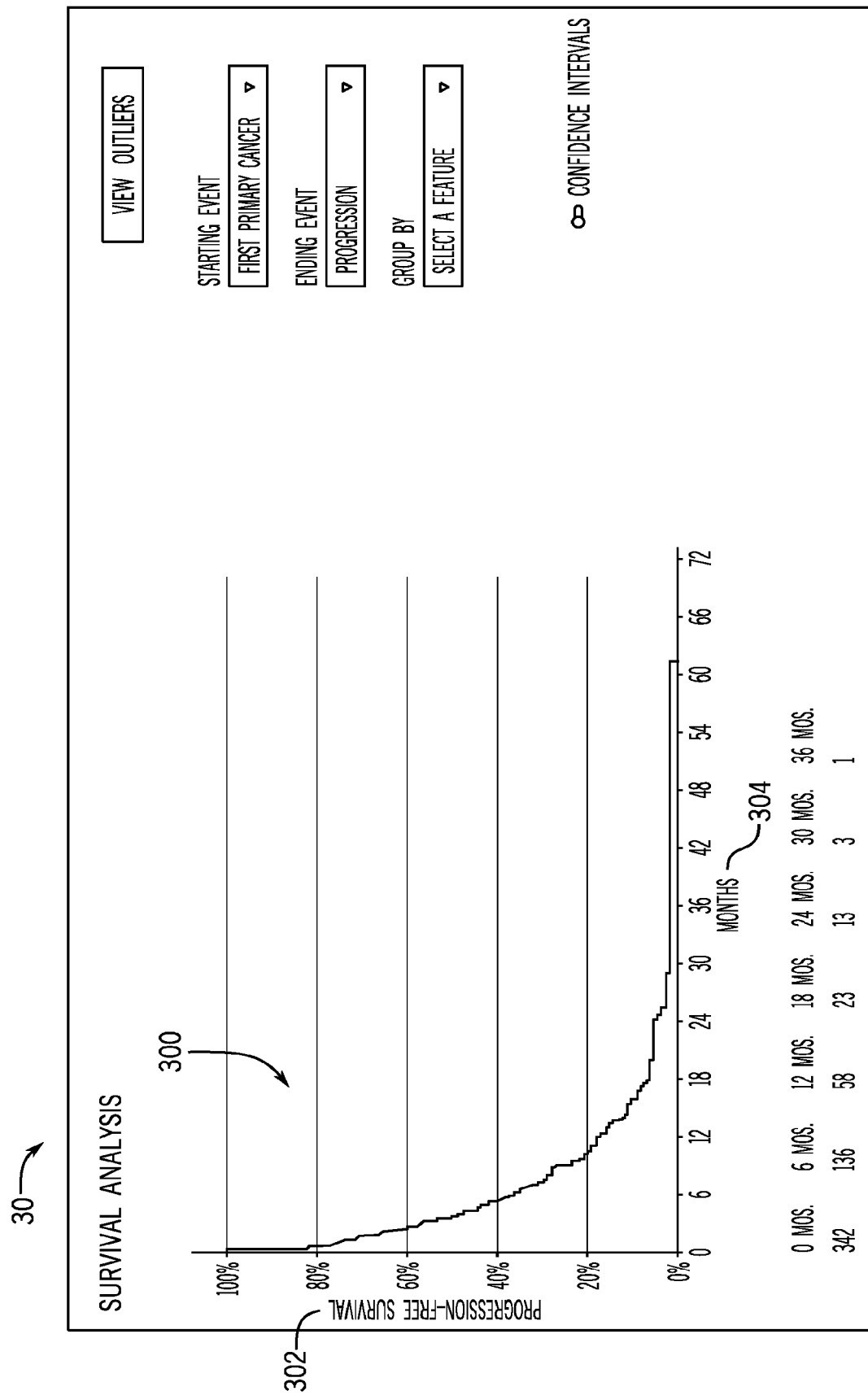
FIG. 15 is one example of a patient survival analysis user interface.

As seen in FIG. 15, the analysis may be presented to the user in the form of a plot 300 of ending event 302, for example, progression free survival or overall survival, versus time 304. Progression for these purposes may reflect the occurrence of one or more progression events, for example, a metastases event, a recurrence, a specific measure of progression for a drug or independent of a drug, a certain tumor size or change in tumor size, or an enriched measurement (such as measurements which are indirectly extracted from the underlying clinical data set). Exemplary enriched measurements may include detecting a stage change (such as by detecting a stage 2 categorization changed to stage 3), a regression, or via an inference (such as both stage 3 and metastases are inferred from detection of stages 2 and 4, but no detection of stage 3).

Figure 16:
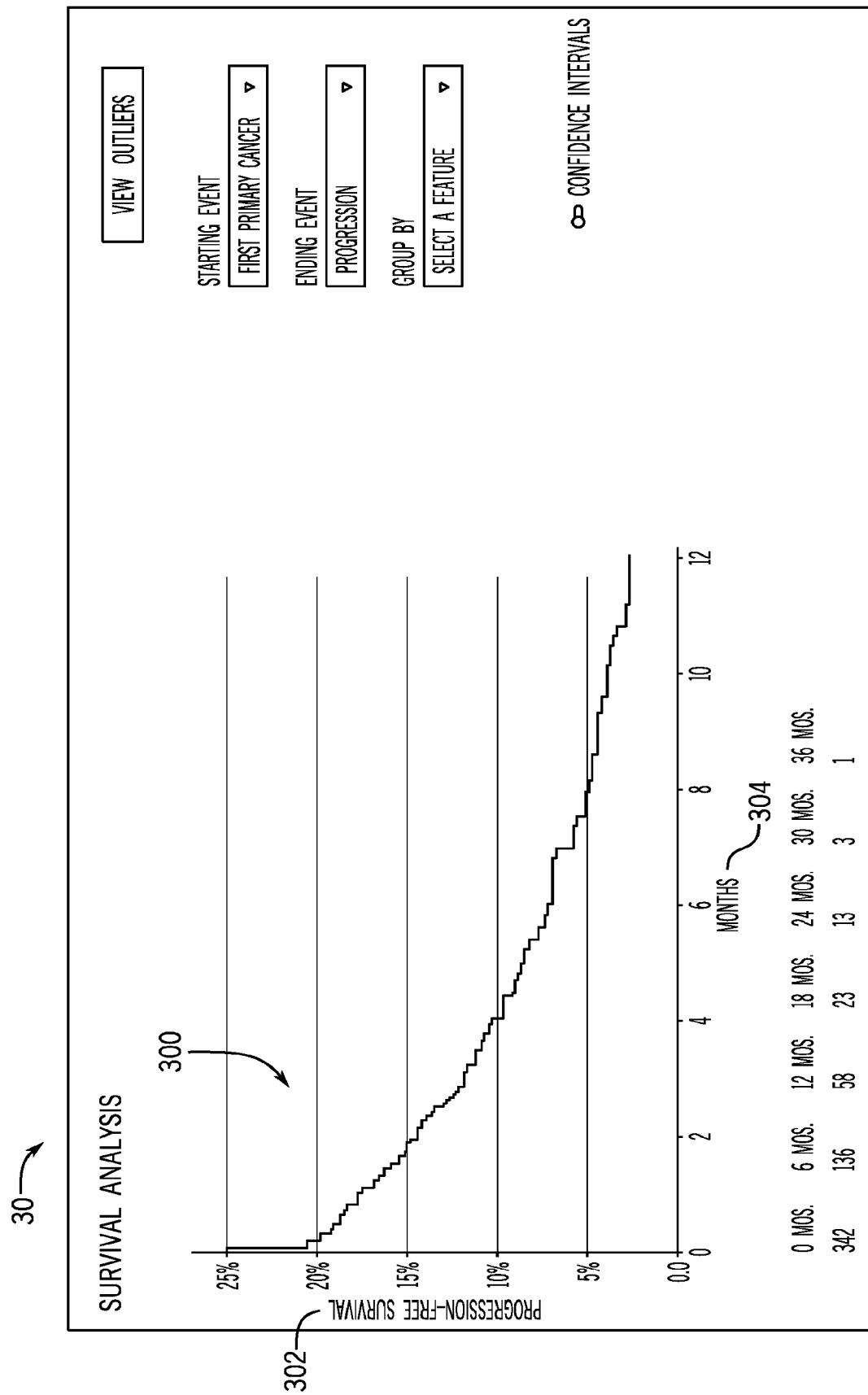
FIG. 16 is another example of a patient survival analysis user interface.
Figure 17:
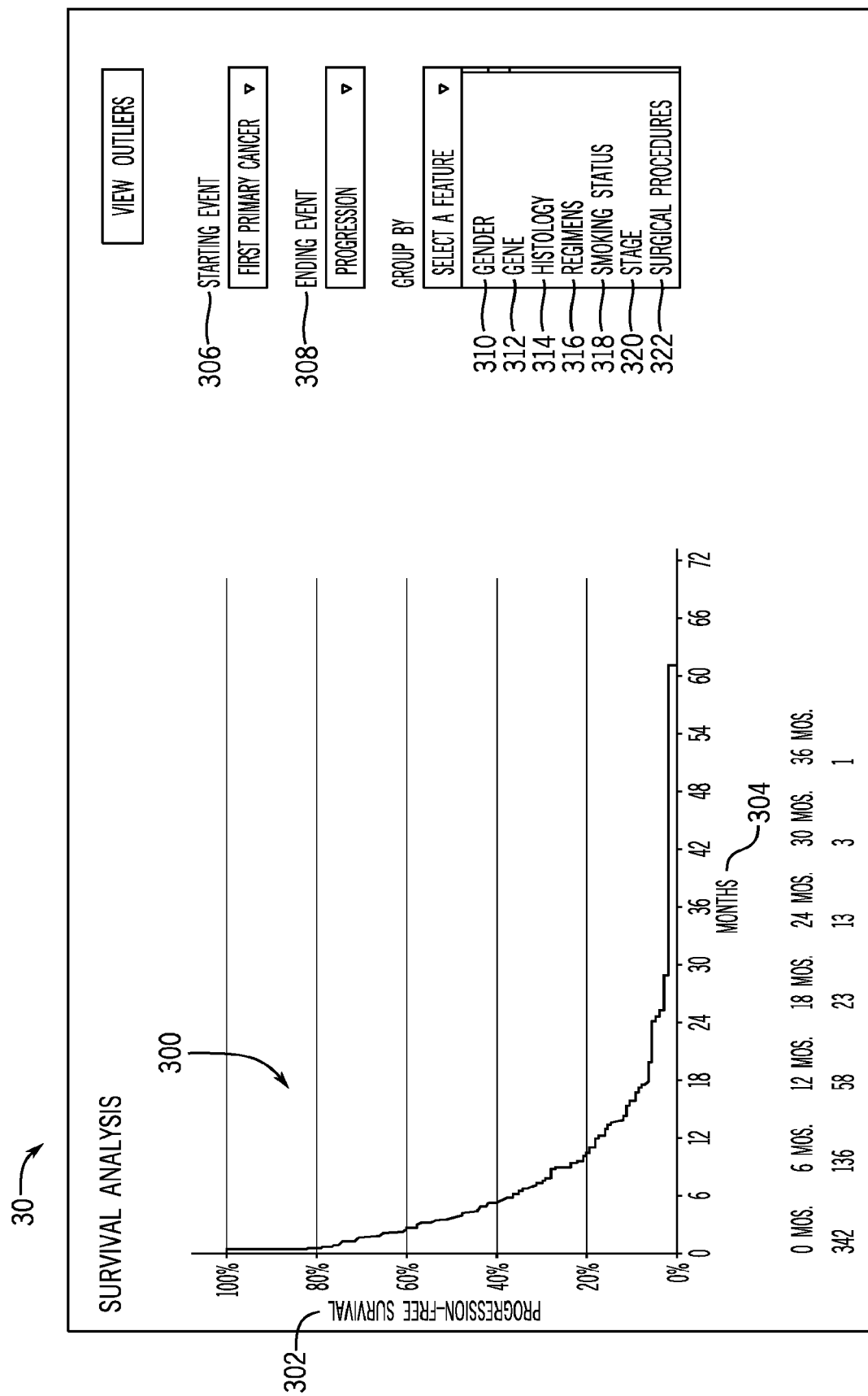
FIG. 17 is another example of a patient survival analysis user interface.

Additionally, the system may be configured to permit the user to focus or zoom in on a particular time span within the plot, as seen in FIG. 16. In particular, the user may be able to zoom in the x-axis only, the y-axis only, or both the x- and y-axes at the same time. This functionality may be particularly useful depending on the type of disease being analyzed, as certain, aggressive diseases may benefit from analyzing a smaller window of time than other diseases. For example, survival rates for patients with pancreatic cancer tend to be significantly lower than for other types of cancer; thus, when analyzing pancreatic cancer, it may be useful to the user to zoom in to a shorter time period, for example, going from about a 5-year window to about a 1-year window.

Turning now to FIGS. 17-20, the user interface 30 also may be configured to modify its display and present survival information of smaller groups within the subset by receiving user inputs corresponding to additional grouping or sorting criteria. Those criteria may be clinical or molecular factors, and the user interface 30 may include a selector such as one or more drop-down menus permitting the user to select, e.g., any of the beginning event 306 or ending event 308, as well as gender 310, gene 312, histology 314, regimens 316, smoking status 318, stage 320, surgical procedures 322, etc.

Figure 18:
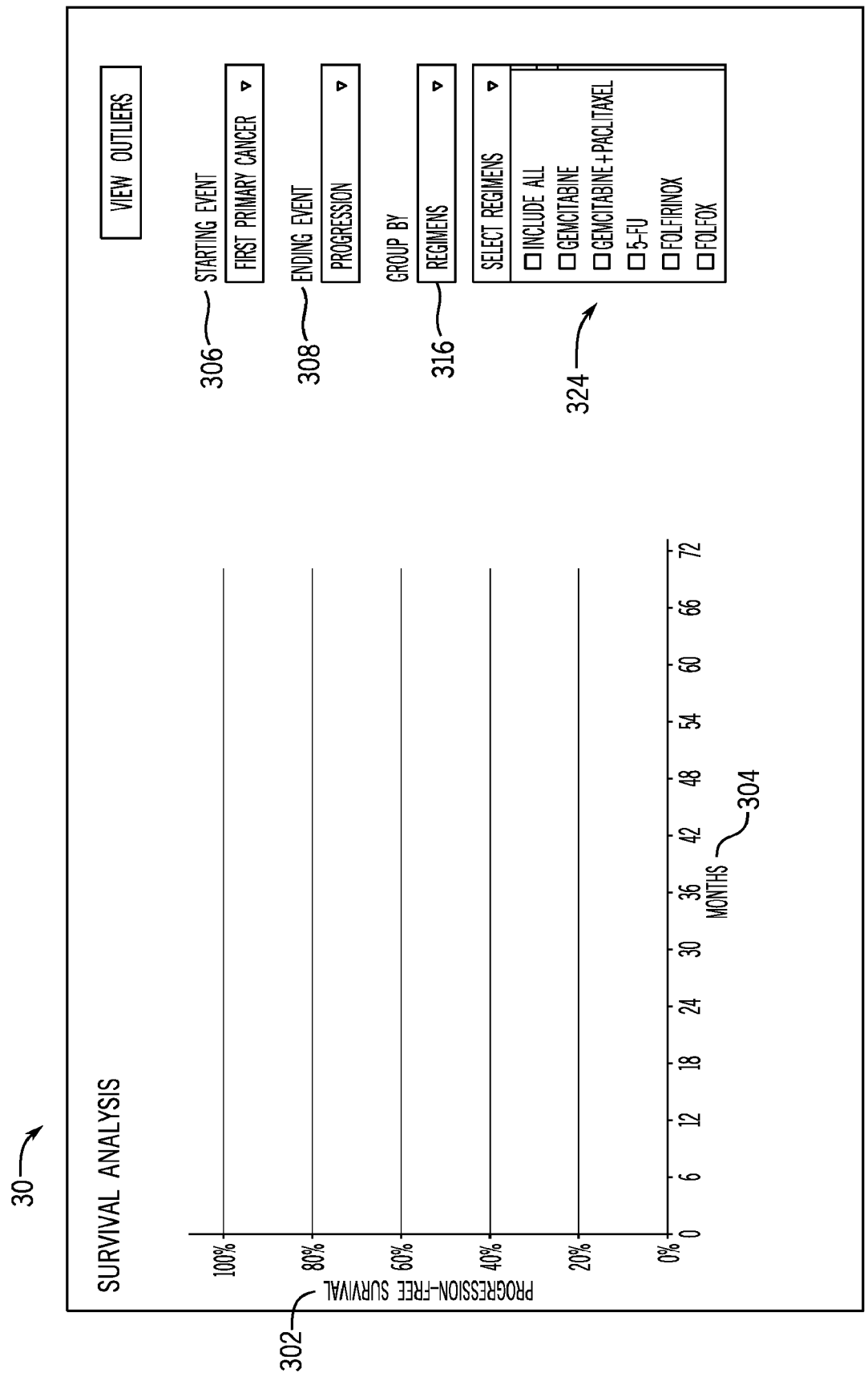
FIG. 18 is another example of a patient survival analysis user interface.
Figure 19:
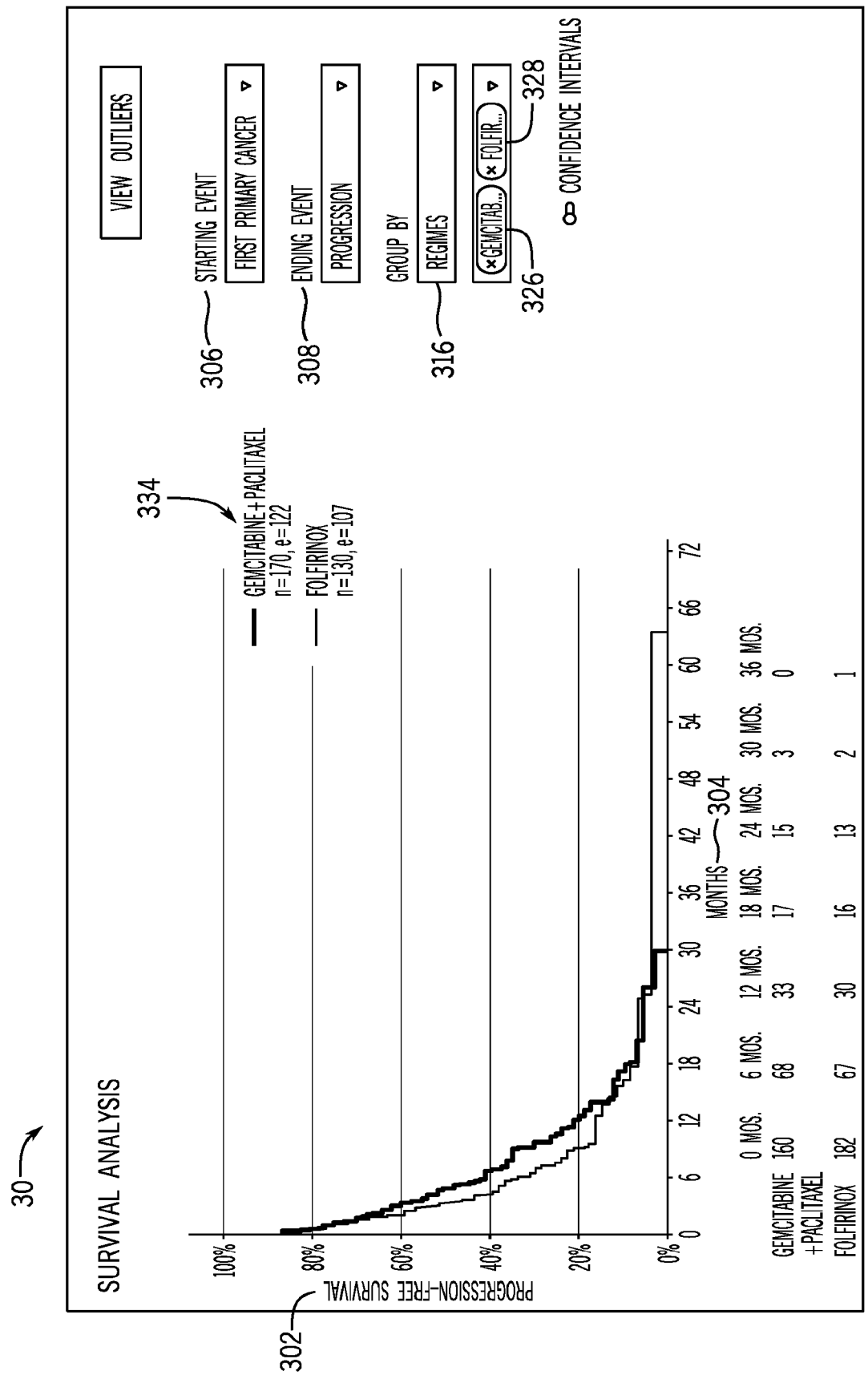
FIG. 19 is another example of a patient survival analysis user interface.

As shown in FIG. 18, selecting one of the criteria then may present the user with a plurality of options relevant to that criterion. For example, selecting "regimens" may cause the system to use one or more value sets to populate a selectable field generated within the user interface to prompt the user to select one or more of the specific medication regimens 324 undertaken by one or more of the patients within the subset. Thus, as FIG. 19 depicts, selecting the "Gemcitabine+Paclitaxel" option 326, followed by the "FOLFIRINOX" option 328, results in the system analyzing the patient subset data, determining which patients' records include data corresponding to either of the selected regimens, recalculating the survival statistics for those separate groups of patients, and updating the user interface to include separate survival plots 330, 332 for each regimen. Adding a group/adding two or more selections may result in the system plotting them on the same chart to view them side by side, and the user interface may generate a legend 334 with name, color, and sample size to distinguish each group.

Figure 20:
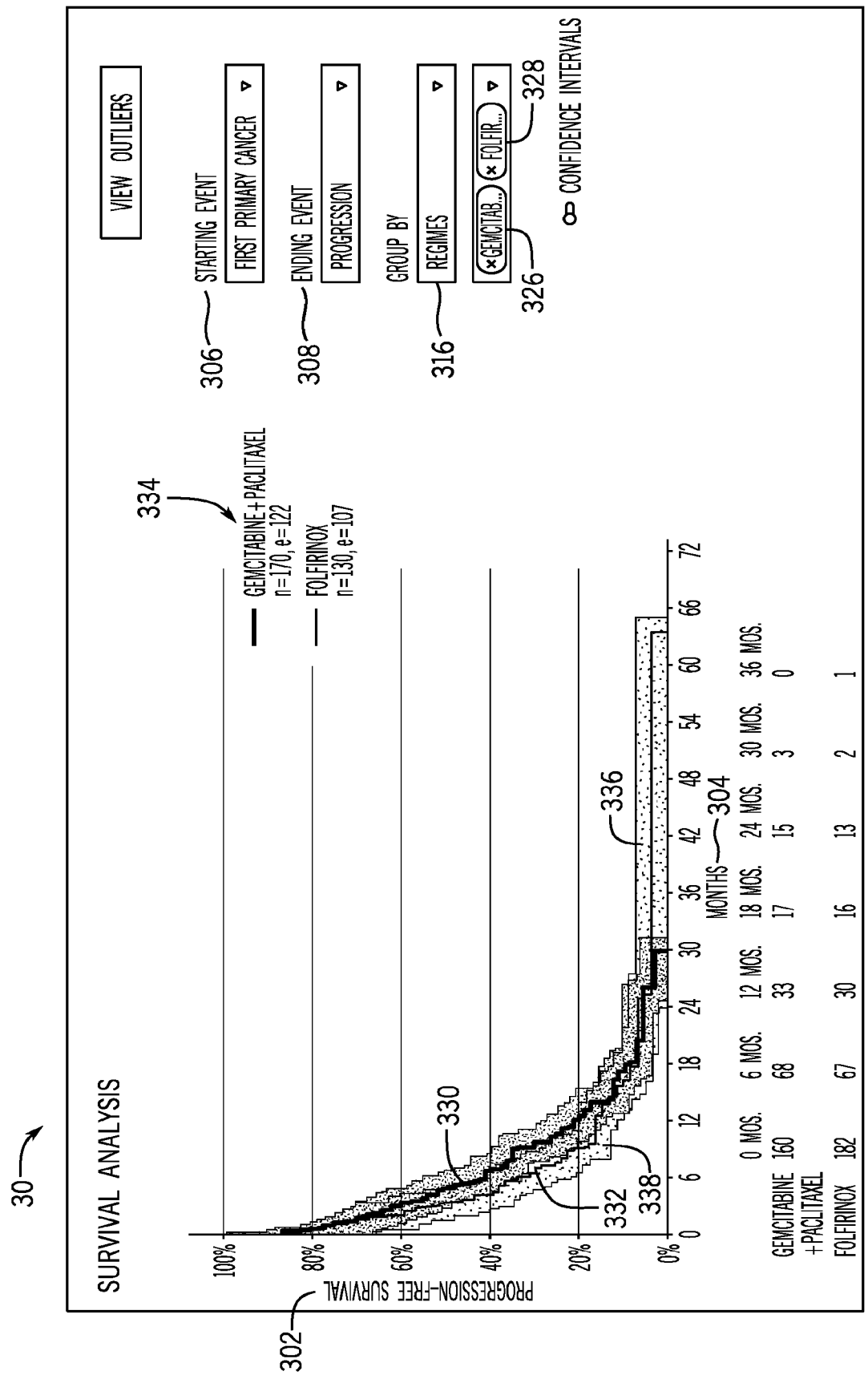
FIG. 20 is another example of a patient survival analysis user interface.

As seen in FIG. 20, the system may permit a greater level of analysis by calculating and overlaying statistical ranges with respect to the survival analysis. In particular, the system may calculate confidence intervals with regard to each dataset requested by the user and display those confidence intervals 336, 338 relative to the survival plots 330, 332. In one instance, the desired confidence interval may be user-established. In another instance, the confidence interval may be pre-established by the system and may be, for example, a 68% (one standard deviation) interval, a 95% (two standard deviations) interval, or a 99.7% (three standard deviations) interval. Confidence intervals may be calculated as Kaplan Meier confidence intervals or using another type of statistical analysis, as would be appreciated by one of ordinary skill in the relevant art.

As will be appreciated from the previous discussion, underpinning the utility of the system is the ability to highlight features and interaction pathways of high importance driving these predictions, and the ability to further pinpoint cohorts of patients exhibiting levels of response that significantly deviate from expected norms. In this context, high importance may be understood to be based upon feature importance to an outcome of a prediction. In particular, features that provide the greatest weight to the prediction may be designated as those of high importance. The present system and user interface provide an intuitive, efficient method for patient selection and cohort definition given specific inclusion and/or exclusion criteria. The system also provides a robust user interface to facilitate internal research and analysis, including research and analysis into the impact of specific clinical and/or molecular attributes, as well as drug dosages, combinations, and/or other treatment protocols on therapeutic outcomes and patient survival for potentially large, otherwise unwieldy patient sample sizes.

The modeling and visualization framework set forth herein may enable users to interactively explore auto-detected patterns in the clinical and genomic data of their filtered patient cohort, and to analyze the relationship of those patterns to therapeutic response and/or survival likelihood. That analysis may lead a user to more informed treatment decisions for patients, earlier in the cycle than may be the case without the present system and user interface. The analysis also may be useful in the context of clinical trials, providing robust, data-backed clinical trial inclusion and/or exclusion analysis. Backed by an extensive library of clinical and molecular data, the present system unifies and applies various algorithms and concepts relating to clinical analysis and machine learning to generate a fully integrated, interactive user interface.

Outlier Analysis Module

Turning now to FIGS. 21-24, in another aspect, the system may include an additional user interface such as patient event likelihood analysis user interface 32 to quickly and effectively determine the existence of one or more outliers within the group of patients being analyzed. For example, the interface in FIG. 21 permits a user to visually determine how one or more groups of patients separate naturally in the data based on progression-free survival. This user interface includes a first region 400 including a plurality of indicators 402 representing a plurality of patient groups, where each patient in a given group has commonality with other patients in that group; for example, commonality may be based on one or more of the above mentioned attributes, additional, system-defined, and tumor-related criteria used for filtering, and other medical information capable of being stored in a structured format that may be identified by the system. Additionally, groups may be formed from the absence of any attribute. For example, a commonality may be found by a group that never took a medication, never received a treatment, or otherwise share an absence of one or more attributes. This region may resemble a radar plot 406, in that the indicators are plotted radially away from a central indicator 408, as well as circumferentially about that indicator, where the radial distance from the central indicator 408 is reflective of a similarity between the patients represented by the central and radially-spaced indicators, and where circumferential distances between radially-spaced indicators is reflective of a similarity between the patients represented by those indicators. In this instance, similarity with regard to radial distances may be based primarily or solely on the criterion/criteria governing the outlier analysis. For example, when analyzing patient groups with regard to progression-free survival ("PFS"), the central point or indicator 408 may be based on a particular fraction or percentage of the PFS (e.g. 10%, 25%, 50%, 75%, or other percentage) of the entire cohort over the time period evaluated, the radial distance from the central point or indicator 408 may be indicative of the progression-free survival rate of the groups of patients reflected by the respective indicators 402 such that groups of patients with better than the particular percentage PFS are plotted above the central point or indicator 408 and that groups of patients with worse than the particular percentage PFS are plotted below the central point or indicator 408, and the distance from the central point on the X axis may be derived based upon the size of the population, a difference between an observed and expected PFS, or similar metric.

Figure 21:
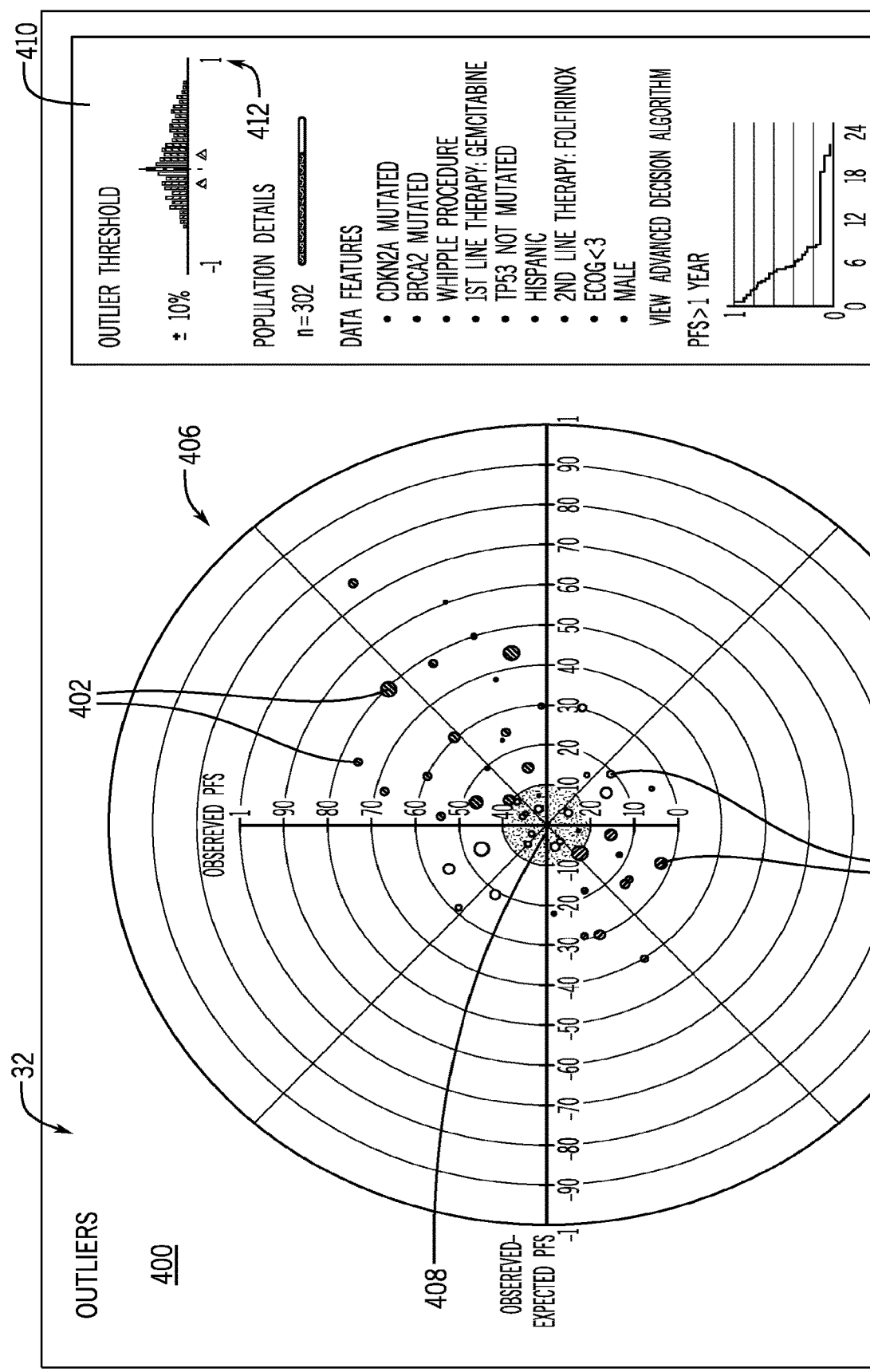
FIG. 21 is an example of a patient event likelihood analysis user interface.
Figure 22:
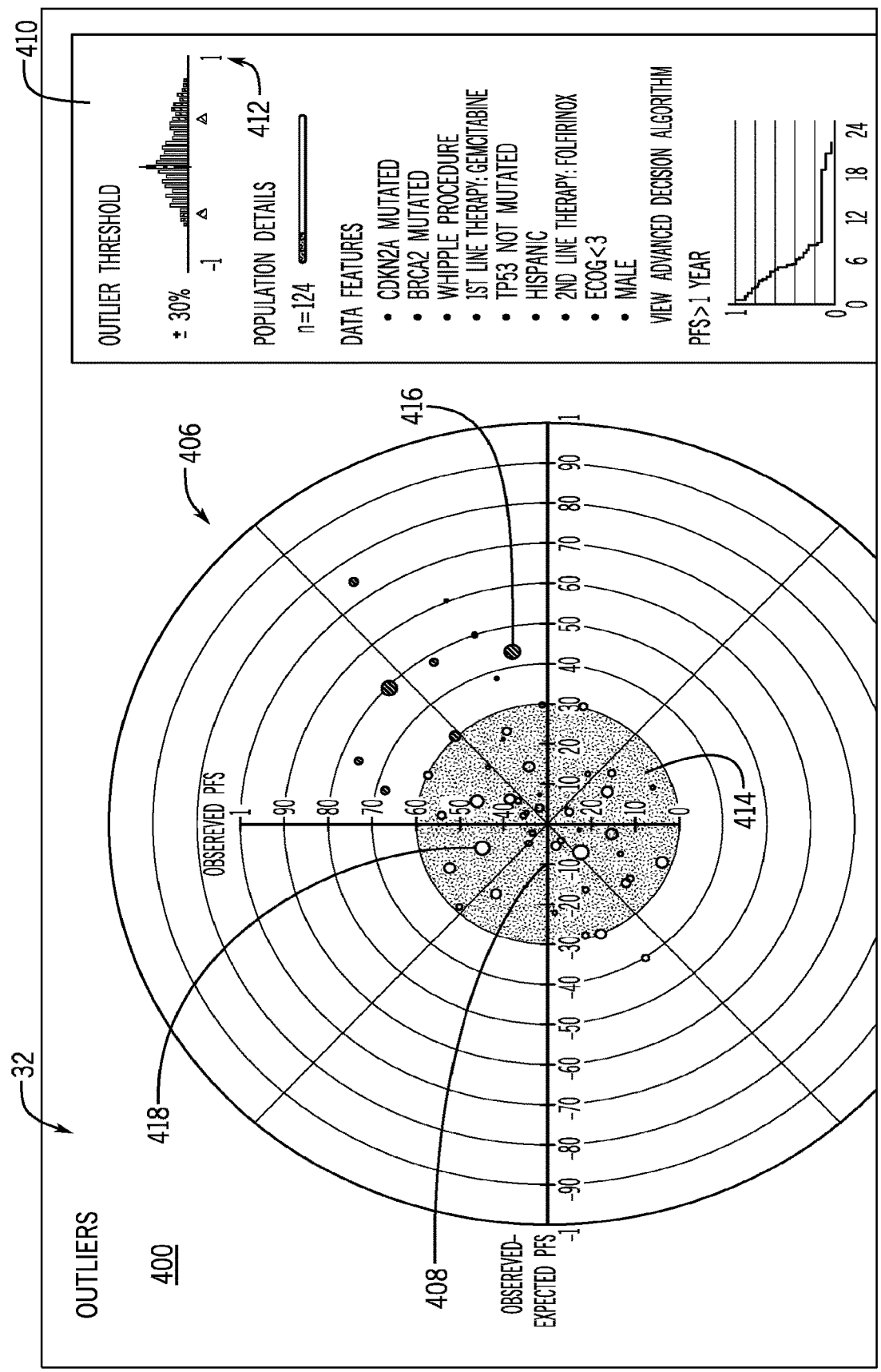
FIG. 22 is another example of a patient event likelihood analysis user interface.

Additionally, the user interface may include a second region 410 including a control panel 412 for filtering, selecting, or otherwise highlighting in the first region a subset of the patients as outliers. Setting a value or range in the control panel may generate an overlay 414 on the radar plot (see FIG. 22), where the overlay may be in the form of a circle centered on the central indicator 408 and the radius of the circle may be related to the value or range received from the user in the second region 410. In this aspect, the user may select a value that is applied equally in both directions relative to the reference patient. For example, the user may select "25%," which may be reflected as a range from −25% to +25% such that the overlay may be a uniform circle surrounding the central point or indicator 408. Alternatively, the system may receive multiple values from the user, for example, one representing a positive range and a second representing a negative range, such as "−20% to +25%." The values may be received via a text input, drop down, or may be selected by clicking a respective position on a graph. In that case, the overlay may take the form of two separate hemispheres having different radii, the radii reflective of the values received from the user. As seen in FIGS. 21 and 22, the values may indicate the percent deviation from whatever value is related to the central point or indicator 408. For example, FIGS. 21 and 22 are displaying progression-free survival (PFS) percentages for various clusters of patients centered around a patient with a 0% PFS value. FIG. 21 includes an overlay 414 at the +/−10% range, while FIG. 22 shows how the overlay is adjusted when the range is modified to +/−30%. It will be appreciated that the central point or indicator 408 could be associated with a patient at a non-zero value, e.g., 20% PFS. In that case, the +/−10% range would encapsulate clusters of patients in a 10-30% PFS range, while the +/−30% range would encapsulate clusters of patients in the −10-50% range. In either case, once the system has received a user input, the indicators covered by the overlay may change in visual appearance, for example, to a grayed-out or otherwise less conspicuous form, as is shown in FIG. 22 in which values 416 that are outside the outlier threshold 414 (shown in a histogram format in the upper right corner of FIG. 22) are a darker color (e.g. blue or shaded) and the values 418 within the outlier threshold 414 are displayed in a lighter color (e.g. pale gray or unshaded). That is, indicators outside of the overlay may remain highlighted or otherwise more readily visually distinguishable, thereby identifying those indicators as representing outliers.

Figure 23:
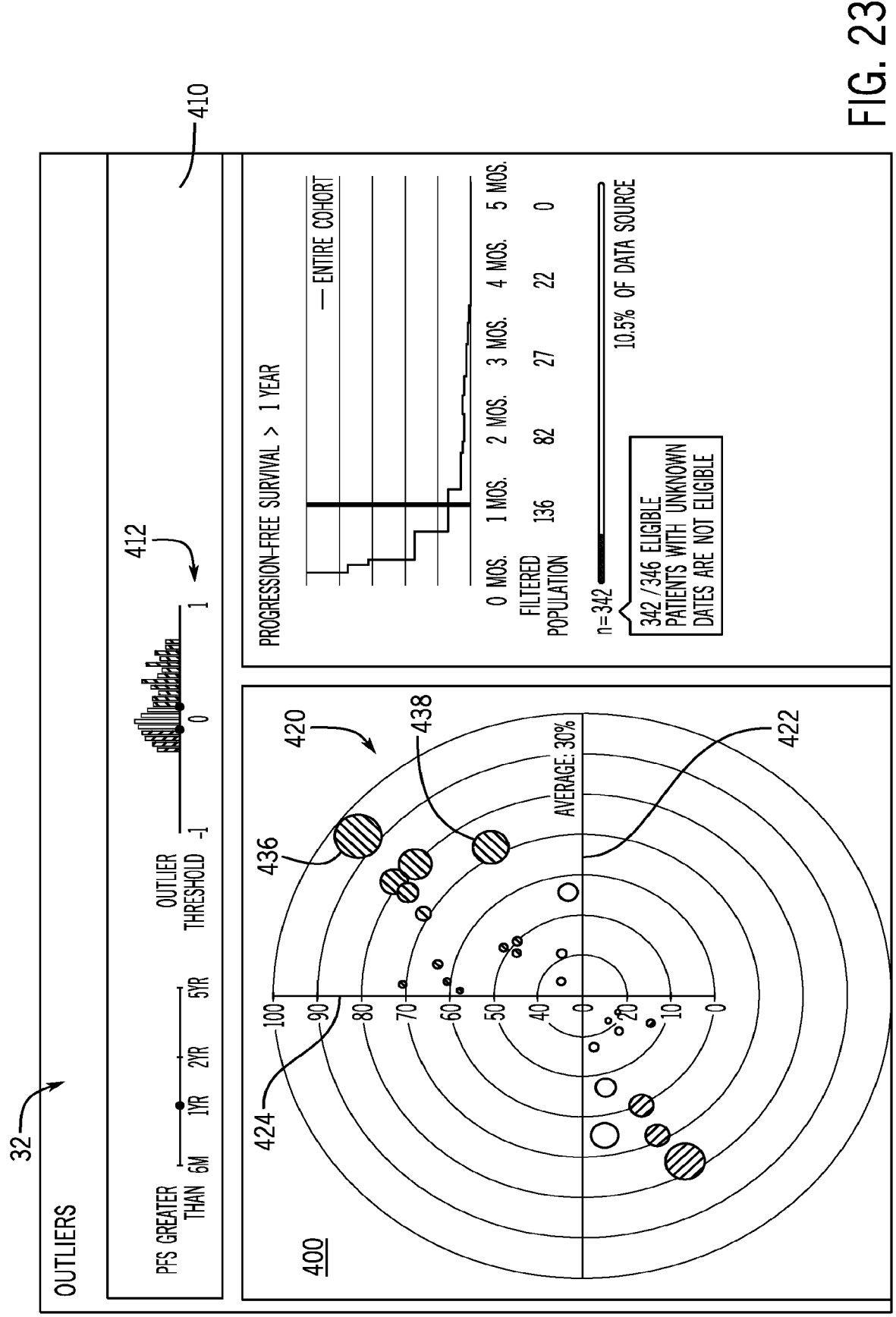
FIG. 23 is another example of a patient event likelihood analysis user interface.
Figure 24:
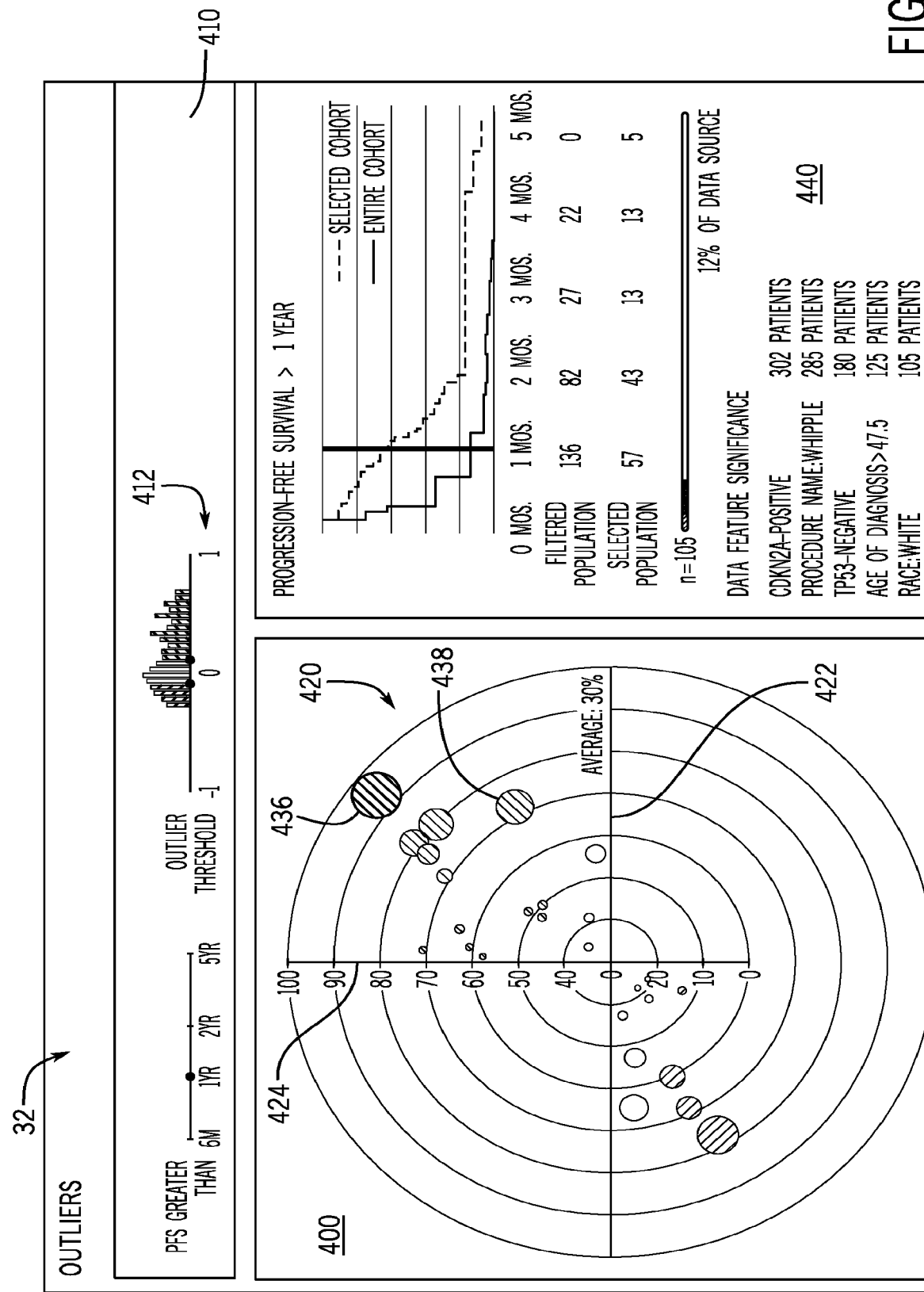
FIG. 24 is another example of a patient event likelihood analysis user interface.

In another aspect, as seen in FIGS. 23-24, the first region 400 of the user interface may include a different type of plot 420 of the plurality of patient groups than the radar-type plot just discussed. In this aspect, an x-axis 422 may represent the number of patients in a given group represented by an indicator and a y-axis 434 may represent a degree of deviation from the criterion/criteria being considered. As a result of these display parameters, this user interface 32 will present the largest patient groups 436 farthest away from the y-axis and the largest outlier groups 438 farthest away from the x-axis 422. (For both this user interface and the one previously described, it should be appreciated that the origin may not reflect a value of 0 for either the y-axis or the radial dimension, respectively. Instead, the origin may reflect a base level of the criterion/criteria being analyzed. For example, in the case of progression-free survival, the base group may have a 2-year rate of 15%. In that case, deviations may be determined with regard to that 15% value to assess the existence of outliers. Such deviations may be additive, +/−20% may be 0% to 35% (0% instead of −5% because negative survival rates are not possible), or multiplicative, +/−20% may be 12% to 18%).

As with the previously described user interface, the interface of FIGS. 23-24 may include a second region 410 including a control panel 412 for modifying the presentation of identifiers in the first panel 400. Again, as with that interface, the control panel may permit the user to make uniform or independent selections to the positive and negative sides of a scale. In particular, as seen in FIG. 24, the control panel 412 in this instance permits the user to independently select the positive and negative ranges in the search for outliers. Upon making each selection, the user interface 32 may adjust dynamically to cover, obscure, un-highlight, remove, or otherwise distinguish the indicators falling within the zone(s) selected by the user from the outlying indicators falling outside of that zone. Due to the configuration of the x- and y-axes, as discussed above, this user interface 32 may be configured to make it possible for the user to quickly identify which outlier group is the farthest removed from the representative patient/group, since that outlier group will be the farthest spaced from the x-axis, in the positive direction, the negative direction, or in both directions. Similarly, the user interface 32 may be configured to make it easy for the user to quickly, visually determine which patient group has the largest number of patients, since that group will be the farthest spaced from the y-axis, in the positive direction, the negative direction, or in both directions. Still further, the combination of axes may permit the user to make a quick visual determination as to which indicator(s) warrant(s) further inspection, for example, by permitting the user to visually determine which indicator(s) strike an ideal balance between degree of deviation/outlier and patient size.

With regard to either outlier user interface described above, the interface further may include a third region 440 providing information specific to a selected node when the system receives a user input corresponding to a given indicator, for example, by clicking on that indicator 436 in the first region of the interface, as seen in FIG. 24. In one aspect, that additional information may include a comparison of the criterion/criteria being evaluated as compared to the values of the overall population used to generate the interface of the first region. Information in this region also may include an identification of a total number of patients in a record set, a number of patients that record set was filtered down to based on one or more different criteria, and then the population size of the selected node as part of an in-line plot, which size comparisons may help inform the user as to the potential significance of the outlier group.

Figure 25A:
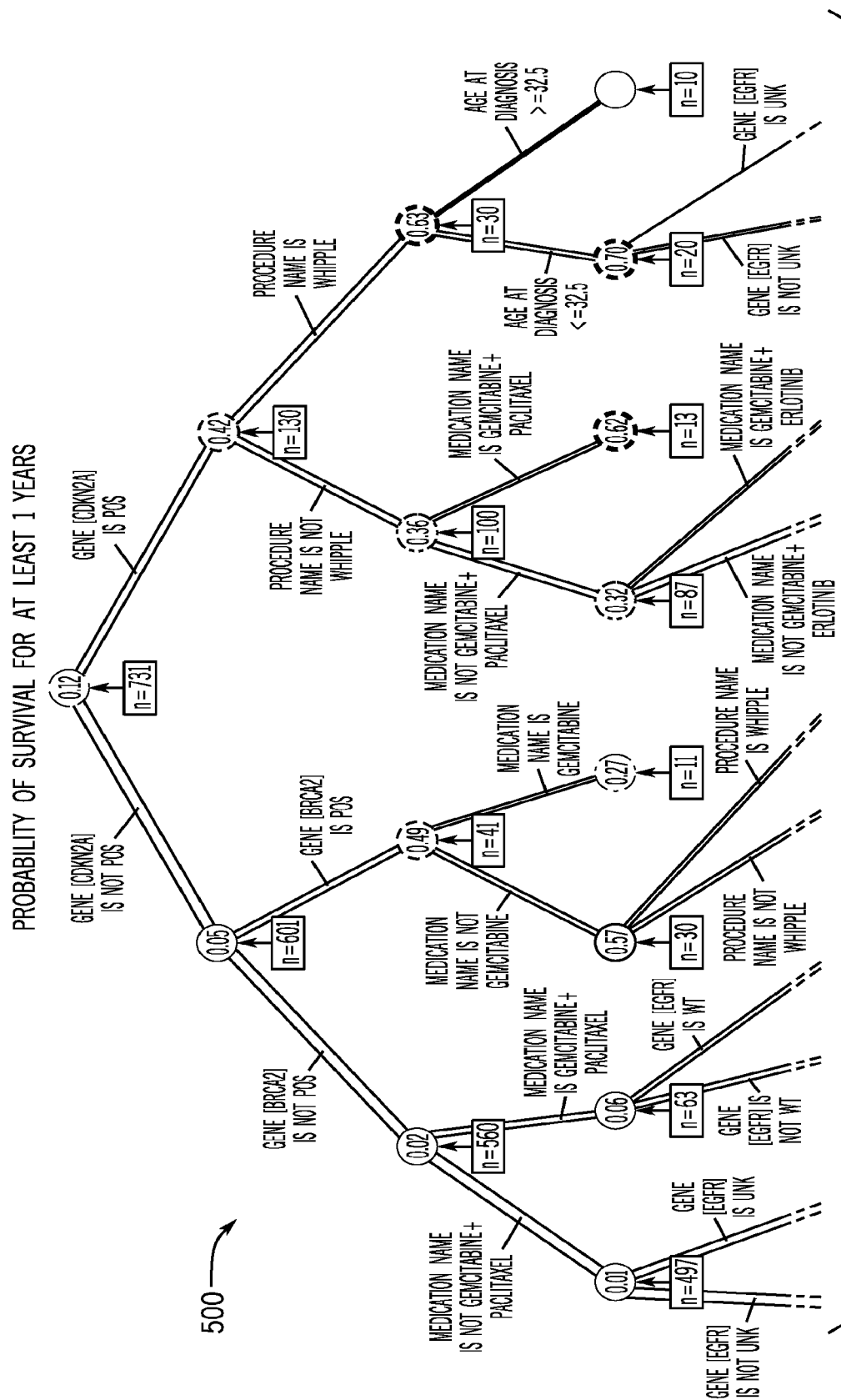
FIGS. 25A and 25B show an example of a binary decision tree for determining outliers usable with respect to the patient event likelihood analysis user interface.
Figure 25B:
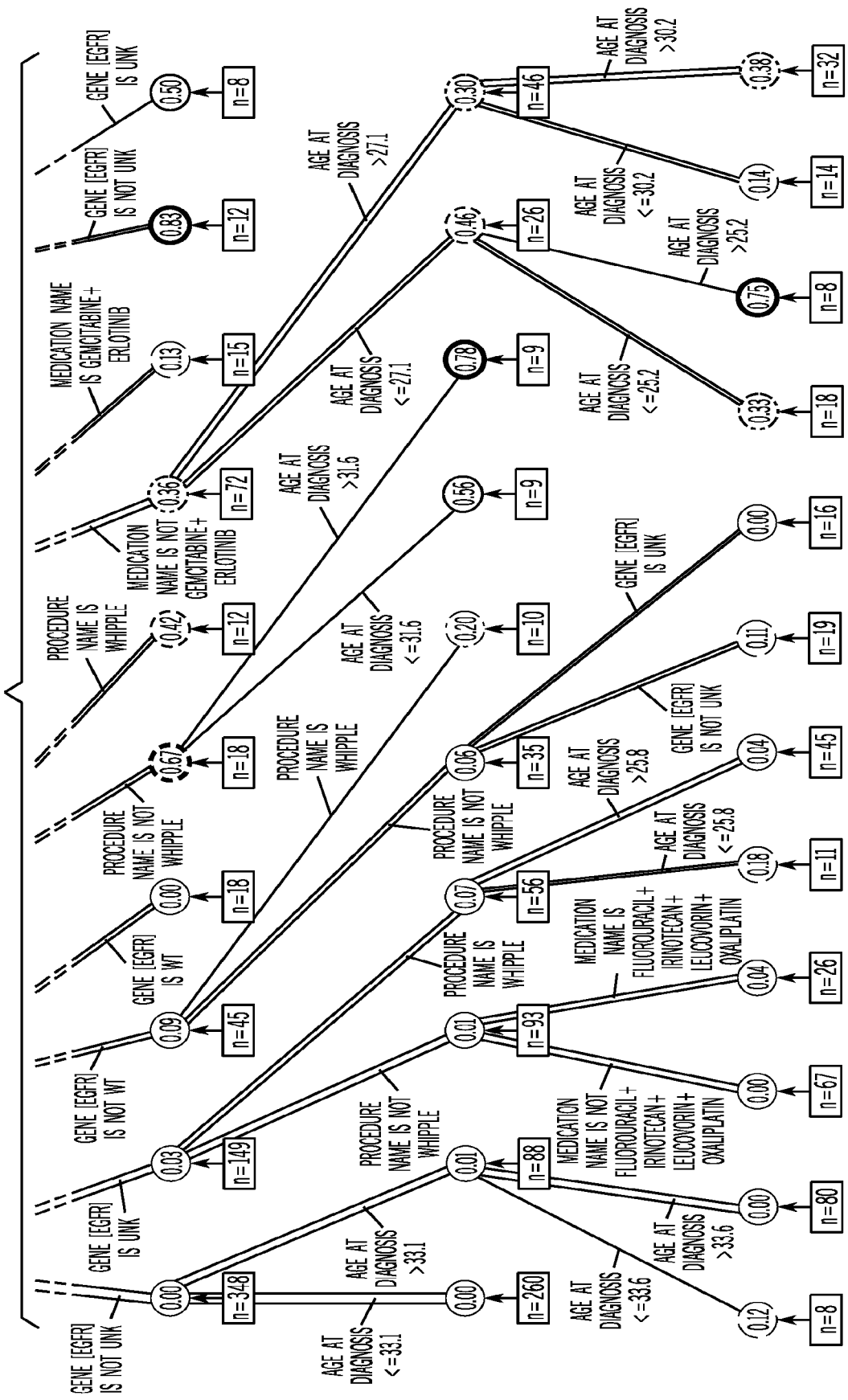

Additionally, with regard to either outlier user interface described above, the algorithm to determine the existence of an outlier may be based on a binary tree 500 such as the one seen in FIGS. 25A and 25B. In order to generate such a tree, the system may separate each feature into its own category. For each category, the system then may determine which subset of the cohort have a largest spread of progression free survival vs. non-survival and treat the feature split which generated the largest spread as an edge between nodes and the features themselves as nodes. The system may continue with this analysis until it encounters a leaf. For example a mutation column may be separated into either "mutated" or "not mutated," and an age option may be set by the user to be "over 50" vs. "under 50." The system then may determine what the biggest cutoff age for survival is, and use that as the binary decision point. Within all of these categories, each having a binary selection that split it into two groups, the system may determine which has the better survival and which has the worse survival, and compare those determinations across all columns to find the group having the biggest difference. A category with the biggest difference is the first node split in a tree that continues to split at additional nodes, forming a plurality of branches where the category criterion for the group is the edge between each node. Each of the branches terminates in a leaf, which is just a split of all the features that came before to identify a group of people with the highest PFS within the cohort according to the divisions above it. In one aspect, the system may treat each leaf as an outlier. Alternatively, outliers may be certain, particularly divergent features. For example, outlier leafs may be those that deviate from a user-input or an expected value by some threshold, e.g., one standard deviation or more away from the expected threshold.

In some instances, data in a branch may be lost when the system fully extrapolates out to a leaf. In such instances, the system may scan features that a current patient has in common with outlier patients, and suggest changes to clinical process that may place them in a new bucket (leaf/node) of patients that have a higher outlier. For example, if a branch has a high PFS in a node, but loses the distinction by the time the branch resolves in a leaf, the system may identify the node with the highest PFS as a leaf.

In order to generate an expected survival rate for a population, the system may rely upon a predictive algorithm built on the survival rates of the patients in the data set 14.

Alternatively, the system may use an external source for a PFS prediction, such as an FDA published PFS for certain cancers or treatments. The system then may compare the expected survival rate with an observed PFS rate for a population in order to determine outliers.

In one particular embodiment, a method for identifying one or more outlier groups of patients are provided. The method includes steps of selecting a cohort of patients, where the cohort includes a plurality of patients. Selection of the cohort may be based on identifying a group of patients having a particular condition such as a particular disease. In one particular embodiment, the cohort may include a group of patients (e.g. several tens, hundreds, thousands, or more) who have non-small cell lung cancer or breast cancer. Other groupings based on other criteria are also possible.

In various embodiments, a next step of the method may include calculating an average survival rate for the cohort of patients. For example, based on available data it may be determined that these patients on average survive for a particular time (e.g. a number of months such as 63 months).

In certain embodiments, another step of the method may include selecting a plurality of clinical or molecular characteristics associated with the cohort of patients. The clinical or molecular characteristics associated with the cohort of patients may include one or more of a genetic marker, a procedure performed on a patient, a pharmaceutical treatment given to a patient, an age at which a patient receives a diagnosis, an age at which a patient receives a treatment, or a lifestyle indicator. In particular embodiments, the clinical or molecular characteristics for a patient may include a smoking status of the patient (e.g. yes, no, unknown), a DNA mutation associated with the patient (e.g. KRAS, BRAF, EGFR, etc.), an age of the patient at a time of diagnosis or treatment (e.g. one or more integers in a particular age range such as 18-115 years old), or one or more treatment procedures or pharmaceuticals received by the patient.

In some embodiments, information regarding the cohort of patients may be used to generate a tree structure, where a node of the tree structure may contain one or more patients who are outliers, that is, patients who have shown a significantly different survival (shorter or longer) for a given set of conditions. Thus to generate the tree structure, for each characteristic of the plurality of characteristics the method may include identifying a plurality of data values associated with the characteristic. For each data value of the plurality of data values associated with the characteristic, the method may include: dividing the cohort of patients into a first subgroup and a second subgroup of the plurality of patients based on a criterion such as whether each patient of the plurality of patients survived during an outlier time period; determining a difference between a number of patients in the first subgroup and the second subgroup; and selecting a data value that results in the difference that is a largest difference between a number of patients in the first subgroup and the second subgroup.

This procedure may be repeated for each data value of each characteristic. For example, for embodiments in which the characteristic relates to an age then the data values include a range of ages, beginning with a lower age range such as age 18, 19, 20, 21, . . . to an upper limit such as age 115 (or another suitable value). In one particular example, if age=20 and the time period is x years (e.g. 5 years), then a first cohort of patients may be those who died x years after an age 20 diagnosis and a second cohort of patients may be those who did not die within x years of an age 20 diagnosis.

To determine the difference, the number of patients who did not survive within the particular time is considered a first subgroup of patients and the number of patients who did survive during the particular time is considered a second subgroup of patients. A difference is then determined between the number of patients in the first and second subgroups for each data value associated with each characteristic. The difference may be divided by the total number of patients in the first and second subgroups and expressed as a decimal value between 0 and 1 (e.g. if 400 patients died x years after age 20 diagnosis and 100 patients did not die x years after age 20 diagnosis, then the difference 400–100=300, which is divided by the total number in the two groups, 500, to get a difference of 0.6). The particular data value having the largest such difference may be retained while the procedure is being performed in order to determine a node for the tree structure (e.g. the largest difference may be a difference of 0.7 at age=44).

The method may further include creating a new node of the tree structure based on the data value that results in the largest difference between the number of patients in the first subgroup and the second subgroup (e.g. a node may be created for age=44). Once the particular data value has been identified as having the largest difference, the method may then include creating branches from the node, including creating a first branch from the new node based on the first subgroup, and creating a second branch from the new node based on the second subgroup. Several examples of potential nodes may include the following: Smoking=Yes, Difference=0.8; DNA mutation=KRAS, Difference=0.78; Age=82, Difference=0.9; Gender=Male, Difference=0.6. Based on this information, the "Age" characteristic has the greatest difference and is selected, where branches may be created that are based on Age greater than or equal to 82 and Age less than 82.

The tree structure may continue to be built by repeating steps above, including steps of dividing the cohort into subgroups for each characteristic and each data value of each characteristic. The starting cohort in each subsequent repeated step is the group of patients in the particular node that is the starting point. This procedure is repeated at each node based on the patients in the first subgroup and the second subgroup, respectively. The procedure continues until one or both of the following conditions are met: (1) a maximum number of nodes or branches has been created, or (2) a node contains fewer than a minimum number of patients. When the procedure is complete, the method may include identifying at least one node from the tree structure which contains an outlier group of patients.

Smart Cohorts

In various embodiments, a prediction model may be developed which facilitates identification of one or more cohorts of patients whose disease progression and/or likelihood of survival is substantially different from expectation, for example significantly longer or shorter than would be expected. Information from these cohorts may then be examined to identify one or more primary factors that could potentially contribute to the survival profile of the cohorts. Identification of smart cohorts may be used to provide precision medicine results for a particular patient, aid in the identification of potential areas of interest to target medication research, and/or identification of unexpected potential to expand medication patient targeting.

Given a set of patient timelines, in various embodiments the objective of the smart cohorts module will be three-fold, attempting to answer one or more of the following questions:

1. What is the likelihood of each patient surviving longer than Y years (or living progression-free for at least Y years) (i.e. "Survival"), measured at each event point in the patient's timeline;

2. What are the primary factors that most influence the expected survival outcome;

3. Which subsets of patients exhibit combinations of these factors such that they stand out as an outlier cohort in terms of their survival profile, relative to expectation, at a user specified anchor timeline event (e.g. at stage IV diagnosis), and what are these patients' characteristics;

This problem may be approached from a time series modeling perspective, with point in time snapshots of feature states, and a binary classification objective. In certain embodiments a tree-based supervised-clustering approach may be used to help identify patient groups of interest, although in other embodiments other analysis and visualization methods are also included.

The inherent temporal nature of the problem is complicated by the fact that target survival at anchor point T may be just as dependent on what happens to the patient after point T as it is on what happened prior to point T. As such, expected future survival cannot simply be modeled using event history alone and future events cannot be included in the model without invalidating the model as a recommender or accidentally introducing information leakage into the features, which could result in overfitting.

In certain embodiments a hybrid two-model approach may be taken. In one part of the approach, a historic only model is trained to derive "expectation" at each time point, and in another part of the approach a forward-looking clustering model is developed to isolate divergences between expected and observed survival, along with associated features.

Thus, in certain embodiments, the hybrid approach may include:

1. Building a dataset that only utilizes backward-looking features, derived at each event point on the timeline;

2. Training a model on such a dataset, to derive predictions for expected future survival at each time point;

3. Tagging these expected survival predictions at each time point to act as best-guess priors using all historic information content;

4. Building a "forward looking" feature set at each time point, ensuring not to permit implicit survival duration information be incorporated into the features (in some cases the historic priors may be included as features in this set as well); and 5. Training a "Summarization/Clustering" model using the forward looking feature set.

At this point, following the "training" step, a determination may be made regarding whether to limit how forward-looking the features for this part may be. For example it may not make sense to include a feature that is observed 2 years in the future if you are trying to predict 1 year survival likelihood. In addition one could also consider giving less importance to features that happen further away from the anchor event. Finally, one may consider excluding event points that are observed after the outcome event of interest, even if such events occur within the X-year boundary. For example, if the first progression event observed is within 6 months, and we are predicting 2 year PFS, then for that patient should exclude all events between 6 months and 2 years.

6. Comparing the expected survival predictions to the actual survival based on the forward looking model, for each of the forward-looking clusters, and identify clusters of high divergence from the expected survival predictions, along with their constituent forward-looking feature set.

Thus the model is directed to determining how future events may impact an expected survival that is predicted by prior events, agnostic to whether the expected survival prediction for a particular sub-cluster is higher than the expected survival prediction for a different cluster (although the root cause of a divergence in expected survival predictions would also be of interest). That is, it is of interest to know whether the next actions have an impact on the patient's survival, or whether patient survival is mainly determined by their already-experienced events.

Figure 26:
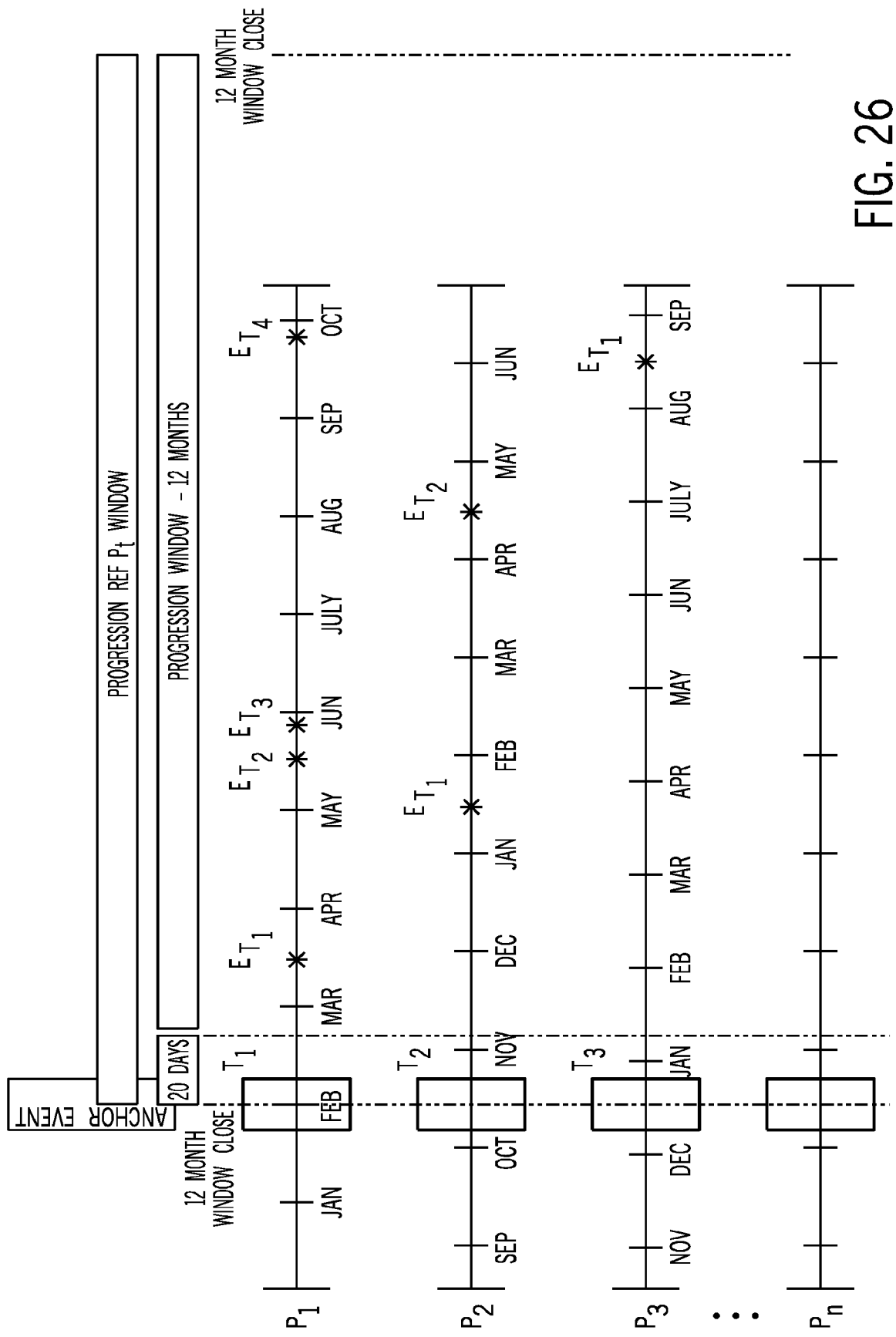
FIG. 26 shows a sample timeline of an anchor event with an associated progression window.

The prediction model may be implemented based on data from a large number of patients, using information about the patients' medical history and treatments along with information about their survival. In order to chronologically align the data from numerous patients, one or more anchor points (also referred to as "patient timepoints") may be identified within the data (FIG. 26). The anchor points identify points in time that may be common to all or at least many of the patients and which may help to standardize the time course of the data relative to events such as disease progression. The anchor points may include events such as time of first diagnosis, time of first metastasis, or time of first treatment, although other anchor point events are also possible. FIG. 26 shows an alignment of timelines for patients $P_1$, $P_2$, $P_3$, ..., $P_n$ based on a common anchor event.

There may be some imprecision with regard to the time of certain anchor point events, for example a date of first diagnosis may occur several weeks earlier or later for a given patient (e.g. relative to when the disease began) due to the time that the patient first notices symptoms or sees a clinician to receive the diagnosis to account for the lack of precision. Therefore, in certain embodiments the anchor points may include a tolerance window before and/or after the date of the anchor point which can provide flexibility in the modeling procedure. In various embodiments, the tolerance window may be +/−1 day, 3 days, 1 week, 2 weeks, 1 month, 2 months, 3 months, or other suitable time period. FIG. 26 shows a diagram of an anchor event (set to January 1) followed by a progression window of 12 months. The anchor event may have a tolerance window of +/−15 days associated with it. In addition, the progression window may have a 3 month tolerance window and thus a progression reference point window may extend backward in time 3 months prior to January 1, to October 1.

With regard to the predictive model, in various embodiments a plurality of data is obtained or received for a plurality of patients, covering a period of time (e.g. a time span covering each of the patients' medical history from the time of their diagnosis until the current time or a time of death, medical history may also begin before diagnosis).

The data may be processed to identify a plurality of patient timepoints (anchor points) that occur within the period of time covered by each patient's data. As discussed above, the anchor points or patient timepoints may include timepoints associated with any patient interaction with the medical system, including any interaction with an individual or facility that provides medical care or obtains medical information such as a care provider, a genetic sequencing organization, a hospital outpatient or inpatient facility, etc. The patient timepoints may be identified by a date attached to or associated with each piece of data in the received set of patient data.

In general both temporal and static features may be derived from the patient data but the analysis at this stage is purely backward-looking to avoid leaking future information. Different categories or classes of features include: "time since last/first XXX"; "number of XXX"; or "demographics." Extracting features may include multiple lookback horizons, for example features may be bounded to the trailing 12 months or may be based on continuous historic analysis.

In one particular example, four timepoints may be identified for a hypothetical patient A: date of biopsy collection, Jul. 1, 2018 (KRAS PL1S147GLU mutation with high SNP effect identified); start anastrozal and lotinib administration, Aug. 1, 2018; radiation therapy performed, Nov. 1, 2018; therapy outcome reported: progression of disease from stage 1 to stage 2, Jan. 1, 2019; imaging performed, Jul. 1, 2018 and Nov. 1, 2018. Other patients B, C, D . . . will each have their own sets of timepoints which may correspond to some of the same events (e.g. diagnosis, start medication, imaging, etc.) or to different events, or to a combination of some of the same events and some different events.

Based on the data for each of the patients and for each patient timepoint, an outcome target for an outcome event may be calculated within a horizon time window; a plurality of prior features may be identified; and a state of each of the plurality of prior features at the patient timepoint may be determined. An outcome event may include a state of the patient and/or the disease, such as progression or death, and the outcome target may be described with a target label such as a yes or no indication of whether the outcome will occur within a particular horizon time window from the patient timepoint/anchor point, along with a date of the endpoint. The horizon time window may include any suitable periods of time such as 3 months, 6 months, 9 months, 12 months, 24 months, 36 months, 48 months, or 60 months, or other periods of time.

In the case of hypothetical patient A, the analysis of a progression event occurring within 6 months of a timepoint is as follows:

Patient A: Jul. 1, 2018—Progression within 12 mo.—Yes, Jan. 1, 2019

Patient A: Aug. 1, 2018—Progression within 12 mo.—Yes, Jan. 1, 2019

Patient A: Nov. 1, 2018—Progression within 12 mo.—Yes, Jan. 1, 2019

Patient A: Jan. 1, 2019—Progression within 12 mo.—null

Since the data for patient A included information of a report of progression from stage 1 to stage 2 on Jan. 1, 2019, there is a valid outcome target for "progression within 12 months" for each of the first three time points: "yes." However, the analysis for the final time point is indicated as "null" because no patient information is available after this date from which to inform the model. Although progression was reported on this date, no further information is available for patient A after this date.

The prior features may include various features related to a patient's medical condition and/or treatment. In various embodiments the prior features may include temporal/time-based events or features, structural or biological features, or molecular/genetic features, among other categories. In particular embodiments the prior features may include one or more of: time since starting a particular medication; time since taking a particular medication; time since last progressive therapy outcome (e.g. patient response to drug); time since metastasis; largest tumor size to date/last recorded tumor size; most severe effect of identified SNP (e.g. low effect, high effect); or RNA features (e.g. expression level per gene/transcript). In some embodiments the data may require additional processing, such as using an autoencoder, to reduce dimensionality of the feature space.

A state of each prior feature may be determined at each of the patient timepoints. For hypothetical patient A, the state of three features (time since starting medication A, time since last imaging, and highest SNP effect as identified by lab A) for each of the four patient timepoints is shown below (note that the value for "time since taking medication A" at the first patient timepoint is "null" since patient A did not take medication A until the next timepoint):

Patient A: Jul. 1, 2018
Time since starting medication A: null
Time since last imaging: 0 days
Highest SNP effect as identified by lab A: Germline: KRAS: High (5)
Patient A: Aug. 1, 2018
Time since starting medication A: 0 days
Time since last imaging: 1 month
Highest SNP effect as identified by lab A: Germline: KRAS: High (5)
Patient A: Nov. 1, 2018
Time since starting medication A: 3 months
Time since last imaging: 0 days
Highest SNP effect as identified by lab A: Germline: KRAS: High (5)
Patient A: Jan. 1, 2019
Time since starting medication A: 5 months
Time since last imaging: 2 months
Highest SNP effect as identified by lab A: Germline: KRAS: High (5)

Next a plurality of forward features may be identified for each patient timepoint of the plurality of timepoints which has a valid outcome target and for each combination of horizon time window and outcome event. The combinations of horizon time windows and outcome events may include "progression within 6 months," "progression within 12 months," "progression within 24 months," progression within 60 months," "death within 6 months," "death within 12 months," "death within 24 months," death within 60 months," etc.

For patient A, using a horizon time window/outcome event combination of "progression within 12 months," the forward features may include:

Patient A: Jul. 1, 2018—
Will patient take medication A after timepoint and before date of endpoint (YES)
Did patient take medication A before timepoint (NO)
Highest SNP Effect As Identified by Lab A: Germline: KRAS: High (5)
Patient A: Aug. 1, 2018—
Will patient take medication A after timepoint and before date of endpoint (NO)
Highest SNP Effect As Identified by Lab A: Germline: KRAS: High (5)
Did patient take medication A before timepoint (YES)
Patient A: Nov. 1, 2018—
Will patient take medication A after timepoint and before date of endpoint (NO)
Highest SNP Effect As Identified by Lab A: Germline: KRAS: High (5)
Did patient take medication A before timepoint (YES)

At this point a plurality of sets of predictions for the plurality of patients may be generated based on the plurality of prior features and the plurality of forward features, and a prediction model may be generated based on the sets of predictions using machine learning. In some embodiments the prediction model may be generated using gradient boosting.

Figure 28:
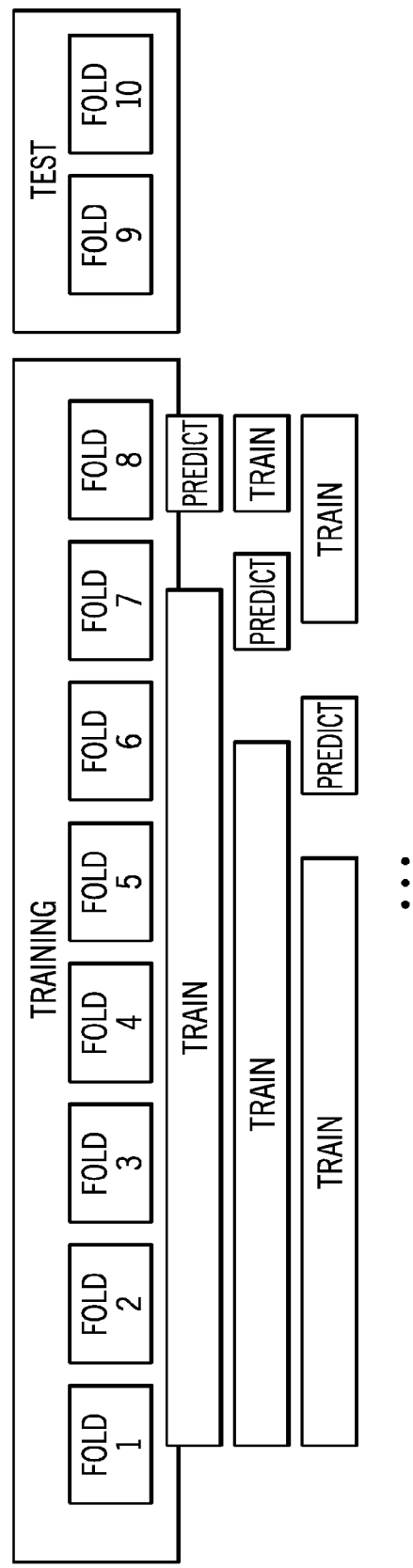
FIG. 28 shows an example of using patient folds for cross-validation.

The plurality of sets of predictions may be divided into several folds, where each fold includes data corresponding to a subset or subgroup of the plurality of patients such that the data for each patient is kept within the same fold (FIG. 28). Thus the machine learning procedure such as gradient boosting may be trained using a subset of the folds. For example, if there are 8 folds, the gradient boosting algorithm may be performed on 7 of the 8 folds. The remaining fold(s) that are not used for training are then run through the model for predictive purposes and the difference between the predicted and actual results may be used to adjust the model before a subsequent round of training is performed. This may be repeated with different folds being omitted from the training step and used for prediction and/or adjustment of the model. More generally, if there are N folds training may be performed on X<N folds and predictions may be performed using N-X folds. In generating the prediction model, various parameters may be adjusted or tuned (depending on the type of model), including learning rate, maximum depth of tree, minimum leaf size, etc. The goal is a model which learns the relationships between the prior features across all patients that lead to the target results. Predictions are received from each patient timepoint from the model and are tied or associated with a corresponding outcome target. In some embodiments, 8 folds may be cross-validated while an additional 2 folds may be complete holdouts for separate testing purposes. Folds may be stratified by a combination of multiple features such as target, gender, cancer, patient event count, etc.

Having generated the plurality of predictions, this information may be used to identify one or more "smart cohorts," that is, one or more cohorts of patients whose disease progression and/or likelihood of survival is substantially different from expectation, for example significantly longer or shorter than would be expected. In general, a decision tree may be constructed using the prediction information to identify various potential smart cohorts, which end up being grouped in various leaf nodes of the decision tree. Disclosed herein are two approaches for constructing decision trees which are referred to as Offline Smart Cohorts and Online Smart Cohorts.

Offline Smart Cohorts

In certain embodiments, a method for identifying a cohort of patients may be developed. The method may include selecting a cohort of patients including a plurality of patients, for example a cohort of 500 breast cancer patients. In general, the cohort may be selected based on the patients having a particular condition in common, e.g. a particular disease.

The method may also include identifying a common anchor point in time from a set of anchor points associated with each of the group of patients, where the common anchor point is shared by each of the group of patients in the cohort. Selecting a common point between all patients facilitates visualization of the data and also makes it possible to prevent the same patient from appearing in the model multiple times at each of the patient's available anchors. The possible anchor points include time of diagnosis, times of treatments, time of metastasis, and others. In one particular embodiment, the time of diagnosis may be selected as the anchor point.

For each patient in the group of patients, a timeline associated with each of the group of patients may be aligned to the common anchor point. Next an outcome target may be identified, such as disease progression within 12 months. Subsequently, the plurality of sets of predictions that were previously generated, each of which includes a predicted target value, may be retrieved for each patient of the group of patients and for each of the plurality of forward features and the plurality of prior features. The predictions may include information such as that shown in Table 1:

TABLE 1

| Patient | Target Prediction | Target Actual | Feature Sets |
| --- | --- | --- | --- |
| A | 0.95 | 1 | A B C D |
| B | 0.93 | 1 | A C D F G |
| C | 0.25 | 0 | B D F |
| D | 0.1 | 0 | A C D G |

More generally, the "target prediction" may take the form of: "Probability for Survival (PFS) in X months," "Death in X months," "Likelihood of taking medication in X months," "Likelihood of other targets in X months," etc. and may be in the form of a decimal value between 0 and 1. The "target actual" value is essentially a binary, yes/no value that is shown as a 1 or a 0 and represents the occurrence or non-occurrence of the event within X months. In various embodiments the feature sets may include prior features and/or forward features, for example any of the features disclosed herein including those listed under the heading of "Features and Feature Models." The prior features may include one or more of Age, Gender, Treatments (e.g. medications, procedures, therapies, etc.), Sequencing/Lab/Imaging results. The forward features, which are discussed further below, may include events, treatments, etc. that happen in the future between the anchor point and the observed target.

In various embodiments, hundreds or thousands (or other, greater numbers) of decision trees may be generated using this information, for example using a procedure similar to that described above for the Outliers procedure. For each of the decision trees that is constructed, for each feature of the plurality of forward features and the plurality of prior features, the following steps may be carried out.

The group of patients may be divided into a first subgroup and a second subgroup based on a difference between the predicted target value and an actual target value;

A difference between a number of patients in the first subgroup and a number in the second subgroup may be determined, and A feature which results in the difference that is a largest difference between a number of patients in the first subgroup and the second subgroup may be selected.

A new node of the tree structure may be created based on the feature that results in the largest difference between the number of patients in the first subgroup and the second subgroup. A first branch may be created from the new node based on the first subgroup, and a second branch may be created from the new node based on the second subgroup. The steps of building the decision tree may then be repeated for each of the first branch and the second branch based on patients in the first subgroup and the second subgroup, respectively. This may continue as the tree is completed as defined by either: a maximum number of nodes or branches has been created, or a particular node contains fewer than a minimum number of patients for all nodes and branches.

The goal of constructing the decision trees is, for each patient and based on the features in the feature set, to predict the difference between the prediction and the actual outcome for the target by clustering the patients based on which features most accurately predict the difference between the prediction and the actual outcomes.

In certain embodiments, the method may include determining a similarity metric by determining how often a given patient ends up in a same leaf node of the trees with other patients across the hundreds or thousands of decision trees. Thus, for each patient of the group of patients, the method may include identifying a co-incidence of the given patient occurring within each of the plurality of leaf nodes, across the hundreds or thousands of decision trees, with each of the other of the plurality of patients. The similarity metric may be determined for the given patient based on a sum of the co-incidence divided by a total number of nodes the given patient is in across all of the hundreds or thousands of decision trees that are constructed and analyzed. In some embodiments a database of patient-patient similarity metrics may be generated based on determining the similarity metric for each of the plurality of patients. In other embodiments the similarity metric may be displayed, e.g. as a cohort radar plot. Further, data may be displayed in association with one or more of the steps outlined above to identify at least one of the plurality of features.

The method may further include determining a similarity metric for a new patient, i.e. a patient different from the initial group of patients. The new patient may be matched with a subgroup of patients corresponding to a particular leaf node of the plurality of leaf nodes based on determining the similarity metric. A treatment may then be identified for the new patient based on matching the new patient with the subgroup of patients. Further, the database of patient-patient similarity metrics may be processed using a dimensionality reducing algorithm to identify a particular cohort of patients having a shared feature such as a shared prior feature or a shared forward feature. In general, dimensionality reduction identifies a certain subgrouping (such as K subgroups) where each of the subgroups 1-k has certain characteristics in common across the grouping that is identified from the entire patient cohort (standard population grouping).

Online Smart Cohorts

In addition to the plurality of predictions, the system may receive an outcome target, a subset of the plurality of forward features corresponding to the outcome target, and a cohort of patients including a subset of the plurality of patients. The cohort may be a group that shares a condition or trait of interest, for example the cohort may be a group of 20,000 breast cancer patients. This group will then be subdivided using the decision tree to find one or more particular subgroups of interest for further investigation.

Table 2 shows an example of the type of prediction data that might be received:

TABLE 2

| Patient | Timepoint | Prediction | Target | Feature Sets |
|---|---|---|---|---|
| A | T1 | .95 | 1 | C D |
| A | T2 | .75 | 1 | B C |
| A | T3 | .66 | 0 | A B C D |
| B | T4 | .92 | 1 | A E F G |

The forward features may include various future actions or conditions that relate to the patients and in certain embodiments could be used to advise patients who have a particular condition. Some of the forward features may be "actionable," that is, they may include things that a given patient could do to possibly change their prognosis or outcome. For example, a doctor or other clinician could take certain steps or actions (e.g. prescribe a medication or combination of medications; prescribe a particular treatment such as surgery, chemotherapy, or radiation; or send a tumor sample for sequencing to receive molecular information such as a test for a DNA marker) to improve the patient's prognosis. Certain molecular features may or may not be considered actionable, based on whether the molecular information that is obtained is associated with a subsequent action or step. In various embodiments, features such as lab results, imaging results, tumor characterization (e.g. histology, grade, TNM stage, etc.) may not be included as forward features in order to avoid making a suggestion to a patient to take an action that is not within their control such as "lower N stage", "increase hemoglobin density", etc.

In various embodiments, this information could be used to counsel a particular patient group, e.g. for N Stage patients with X mutation, treatment A and B taken together improve probability for survival (PFS) within 12 months. For example, Stage 4 Breast cancer patients with the KRAS mutation are expected to progress based on their placement in a cohort (90% progression prediction) and should take anastrozal and lotinib together as an intervening therapy to improve PFS within 12 months (60% progression prediction) based on predictions after the selected anchor point of time of first metastasis. Other specific courses of action could be determined based on the data.

Examples of predictions include predictions of probability for survival within 12 months, for Patient A and B and timepoints T1 (Jan. 1, 2018) and T2 (May 1, 2018), expressed as a probability value between 0 and 1, as shown in Table 3:

TABLE 3

| Patient | Timepoint | Prediction |
|---|---|---|
| A | Jan. 1, 2018 | .95 |
| A | May 1, 2018 | .75 |
| B | Jan. 1, 2018 | .92 |

The outcome target may be a probability for survival within 12 months, given as a 0 or 1, as shown in Table 4:

TABLE 4

| Patient | Timepoint | Prediction |
|---|---|---|
| A | Jan. 1, 2018 | 1 |
| A | May 1, 2018 | 1 |
| B | Jan. 1, 2018 | 1 |

Below is an example of a subset of the plurality of forward features (FD1, FD2, FD3, each indicated below) corresponding to the outcome target including forward data corresponding to probability for survival within 12 months:

Jan. 1, 2018:
FD1 (Patient will take anastrozal and lotinib): (YES)
FD2 (Patient will have radiation therapy): . . .
FD3 (Patient will have surgery): . . . .
May 1, 2018:
FD1 (Patient will take anastrozal and lotinib): (YES)
FD2 (Patient will have radiation therapy): . . .
FD3 (Patient will have surgery): . . . .

The system may also receive an anchor point or patient timepoint, e.g. a time of first diagnosis, a time of first metastasis, a time of first treatment, etc.

A subset of the plurality of forward features may be selected. These features may include medications (future and historic) as well as sequencing (somatic sequencing (future or historic), germline sequencing, etc.). For each patient in the cohort having the anchor point, the prediction model may be provided with the selected subset of the plurality of forward features and a difference may be determined between each of the plurality of predictions and the outcome target.

For example, the model may receive data such as:

Patient A: [0.95-1], [Medications and sequencing data sets]

Patient B: [0.92-1], [Medications and sequencing data sets]

Patient C: [0.63-0], [Medications and sequencing data sets]

The data may include information such as "medications and sequencing data sets at the anchor point" which may include an N×M table of patients and respective features. The respective features may include information such as:

Patient A: Jul. 1, 2018 (date of anchor point)—

Col. 1: Will patient take medication A after timepoint and before date of endpoint (YES)

Col. 2: Did patient take medication A before timepoint (NO)

Col. 3: Highest SNP Effect As Identified by Lab A: Germline: KRAS: High (5)

Subsequently, for each feature of the selected subset of the plurality of forward features, a decision tree may be generated based on determining a greatest difference between each of the plurality of predictions and the outcome target. The decision tree may include a plurality of leaf nodes and one or more branch nodes, and each of the one or more branch nodes may include a pair of branches each of which includes a leaf node or a branch node, where the branches are formed based on a feature selected from the subset of the plurality of forward features.

Each of the plurality of leaf nodes of the decision tree may include a number of patients from the cohort of patients. In some embodiments, the decision tree may continue to split based on the difference between each of the plurality of predictions and the outcome target until the number of patients in a particular leaf node of the plurality of leaf nodes is less than a minimum number of patients. In other embodiments, the decision tree may continue to split based on the difference between each of the plurality of predictions and the outcome target until the number of levels of the decision tree has reached a particular number, that is, is equal to a maximum number of levels. In one specific example, each patient's status with regard to a feature "KRAS Somatic Historical >3" may be used to split a branch node to two branches based on whether each patient's historical importance value for this marker is greater than 3 (high importance).

The leaf nodes of the decision tree provide information that may be used to identify cohorts of interest. In some cases leaf nodes may have high values for the prediction target since prediction values are on average much higher than target values. For patient C in the examples above, the prediction indicated that it was likely that patient C's condition would progress but in fact it did not. In other cases leaf nodes may also generate low negative values for the difference of "prediction minus target"; for example, a prediction minus target may be [0.05-1]=–0.95, which would indicate that the patient's condition would be unlikely to progress but in some instances it may still progress. However in certain cases the leaf nodes may have a value of approximately zero, which indicates that the model has made an accurate prediction. The Smart Cohorts procedure focuses on the instances where patients' actual outcomes have greatly deviated from the expected result because these groups of patents can provide information as to what can be done to change the trajectory of a disease progression, whereas the cohorts where the prediction-target differences are closest to zero inform the model on what features are most important to a reliable prediction.

In some embodiments, analytics may be performed on one or more of the leaf nodes of the decision tree, where the analytics parse the branches of the leaf to render them meaningful. Only subsets of features that are sent to the model will be considered for creating splits. In one embodiment in which the subset of features includes "medication" and "molecular," a particular leaf may show "Variant effect on KRAS (somatic) protein (post-anchor): >1" (a molecular feature) and "Will not take medication: Pembrolizumab" (a medical feature). Thus, analytics may be performed on the data to improve the overall quality and to improve the accuracy of the splitting and the resulting leaf nodes. In a particular case (although not relevant to the case in which medication and molecular features are used for splitting), analytics may be used to parse branching information to make otherwise ambiguous information meaningful: information indicating "Gender not male" may be set to "gender female."

In another instance, which relates to the model in which splitting is based on medication and molecular features, the analytics may be used to map data to particular categories and/or ranges to render the data meaningful. For example, a range may be presented as:

Variant effect on KRAS (somatic) protein (post-anchor): =>1, which may map to:

Variant effect on KRAS (somatic) protein (post-anchor): =1 ('negative'), where the term 'negative' indicates 'tested and confirmed not to be mutated' (as opposed to unknown status).

In certain embodiments the analysis which leads to generating branches from a node requires that all of the patients in the resulting leaf nodes meet the particular requirements, that is, the procedure may require 100% cohort participation to form branches. In some cases, however, features derived from the tree may miss statistically relevant cohort features due to this requirement for 100% cohort participation. Therefore in certain embodiments a Subset Aware Feature Effect (SAFE) algorithm may be run to allow features which are shared by fewer than all of the patients (e.g. shared by 95%) of the leaf cohort but not all (e.g. 95%) of patients in the whole cohort to be included in a particular leaf.

In various embodiments the smart cohorts algorithm may be run in an observational mode (which does not use predictions and uses targets only, e.g. 0 or 1) or an algorithmic mode (which uses predictions, e.g. prediction—target [0.95-1]).

The SAFE algorithm has been developed to return viable feature importance ranks based on the selected sub-population of patients, without a need for re-training of the underlying models. Given the predictions from a pre-trained global multi cancer type model on the patient population, the SAFE algorithm may derive approximate high level importance ranks interactively and quickly. In addition, the feature importance ranks may be intelligently and dynamically adjusted to be relevant given a selected subset cohort of the population, without needing to re-train the global model. To optimize interpretability, in certain embodiments the SAFE feature importance algorithm may be agnostic of the underlying machine learning model that was used and may be made to cleanly handle assigning appropriate importance to correlated features. The SAFE algorithm may also provide the ability to explore feature importance on "feature+prediction" datasets for which targets may not necessarily have been defined. Finally, for more continuous features, the SAFE algorithm may enable deeper exploration of the change in feature importance with varying feature value.

In one embodiment, the SAFE algorithm may include calculating a population mean prediction. The algorithm may then include encoding categorical feature levels as the delta between the predicted value and the population mean prediction, where infrequent levels may be grouped together. The algorithm may further include clustering or bucketing of continuous features and processing these features as in the previous step. Next the algorithm may include, for each feature, aggregating an average (p–E(p)) per categorical level. Finally, the algorithm may include, for each feature, assigning an overall feature importance as the frequency-weighted sum of an absolute value of all values.

As can be seen using the above-described approach, the algorithm does not rely explicitly on the presence of a target variable for deriving an importance ranking and instead only requires features and predictions. As such, it can effectively be applied to predictions made on unlabeled datasets, as well generalizing to predictions obtained from different types of machine learning (ML) algorithms.

FIGS. 27A and 27B show an example of adaptive feature ranking in accordance with embodiments of the SAFE algorithm. FIG. 27A shows a list of top 10 features from an overall model, which is based predominantly on breast cancer patients. FIG. 27B shows a list of top 10 features from the dataset from FIG. 27A after creating a subset directed to colorectal stage 4 patients. As can be seen in FIG. 27B, certain features that are more likely to be associated with colorectal patients (e.g. "historical-took_medication: irinotecan" and "historical-took_medication: bevacizumab") have a higher ranking and higher value in the subset directed to colorectal stage 4 patients. On the other hand, features that are not related to colorectal stage 4 patients (e.g. "cancer: lung_cancer" and "cancer: pancreatic_cancer") do not show up in the list in FIG. 27B. FIG. 27C continues with the example of FIGS. 27A and 27B and shows an example of handling of correlated features. Continuing with the colorectal example from FIG. 27B, FIG. 27C shows that, upon addition of duplicated dummy columns based on the following two features: "historical-took_medication: irinotecan" and "historical-took_medication: capecitabine," these duplicated columns properly sort with the other values associated with colorectal stage 4 as would be expected.

Figure 27D:
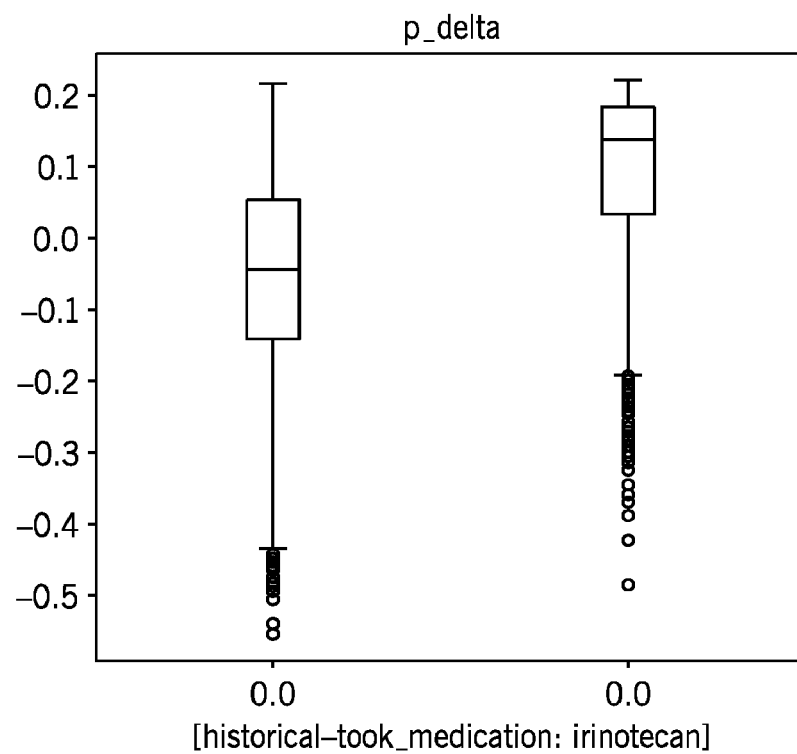
FIGS. 27D and 27E show an example of sample-level importance assignment in accordance with embodiments of the SAFE algorithm.
Figure 27E:
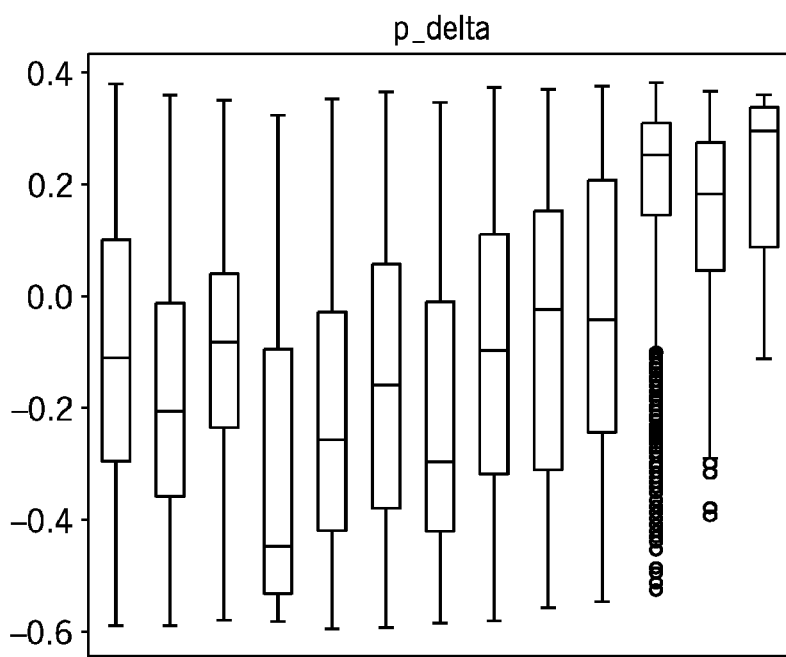

FIGS. 27D and 27E show an example of sample-level importance assignment in accordance with embodiments of the SAFE algorithm. Given the derivation of the SAFE algorithm, one benefit is that each instance of each feature value gets assigned an "impact" value representing its co-occurrence with an observed deviation from prediction mean, which in turn allows one to explore the variation in impact per change in feature value. FIG. 27D shows a boxplot grouped according to the feature of "historical-took_medication: irinotecan." FIG. 27E shows a boxplot grouped according to last stage. FIG. 27D shows that features that co-occur with a "historical-took_medication: irinotecan" value of 1 have a greater impact than those associated with a value of 0, as would be expected for the colorectal stage 4 subset. FIG. 27E shows a greater impact associated with later stages.

Although the SAFE algorithm does not directly factor in feature interactions, these values may be derived from manually constructed composite features. In addition, the SAFE algorithm is geared towards conveying how each feature impacts the predicted values from the underlying model, which is used as an indirect proxy for feature importance to predicting the target, although this will be subject to the efficacy of the model.

Notebooks

In various embodiments, one or more statistical models and analyses may be combined to accommodate a particular purpose and, through a variation of the initial analysis, may be used to solve a number of problems. Such a combination of statistical models and analyses may be stored as a notebook in the Interactive Analysis Portal 22. Notebook is a feature in the Interactive Analysis Portal 22 which provides an easily accessible framework for building statistical models and analyses. Once the statistical models and analyses have been developed, they may then be shared with different users to analyze and find answers to scientific and business questions other than those for which they were initially developed.

1) The Interactive Analysis Portal 22 allows input customization through a simple, intuitive point-and-click/drag-and-drop interface to narrow down the cohort for analysis. Cohorts which have been selected, either through the Interactive Analysis Portal 22, Outliers, Smart Cohorts, or other portals of the Interactive Analysis Portal 22, may be provided to a notebook for processing.

2) A custom application interface (API) having a library of function calls which interface with the Interactive Analysis Portal 22, underlying authorized databases, and any supported statistical models, visualizations, arithmetic models, and other provided operations may be provided to the user to integrate a notebook or workbook with the Interactive Analysis Portal 22 data, function calls, and other resources. Exemplary function calls may include listing authorized sources of data, selecting a datasource, filtering the datasource, listing clinical events of the patients in the current filtered cohort, identification of fusions from RNA or DNA, identification of genes from RNA or DNA, identifying matching clinical trials, DNA variants, identifying immunohistochemistry_(IHC), identifying RNA expressions, identifying therapies in the cohort, identifying potential therapies that are applicable to treat patients in the cohort, and other cohort or dataset processing.

3) The Interactive Analysis Portal 22 allows the Notebook generation to perform one or more statistical models, analysis, and visualization or reporting of results to the narrowed down cohort without having the user code anything in the notebook as the selected models, analysis, visualizations, or reports of the notebook itself are configured to accept the cohort from the Interactive Analysis Portal 22 and provide the analysis on the cohort as is, without user intervention at the code level. Some models may have hyperparameters or tuning parameters which may be selected, or the models themselves may identify the optimal parameters to be applied based on the cohort and/or other models, analysis, visualizations, or reports during run-time.

4) The Interactive Analysis Portal 22 displays the prepared results to the user based on the selected notebook.

5) An associated user may then select a previously generated notebook which applies selected analysis to the narrowed down cohort without having the user code or recode anything in the notebook as the notebook itself is configured to accept the cohort from the Interactive Analysis Portal 22 and provide the notebook results without user intervention.

6) Users may track the computation resources used by their notebooks for understanding the costs for cloud computing or hardware resources over the network and may track the popularity of their notebook to judge the effectiveness of the statistical analysis that they provide through the notebook.

In certain embodiments, notebooks provide a benefit to users by allowing the Interactive Analysis Portal 22 to provide custom templates to their selected data and leverage pre-built healthcare statistical models to provide results to users who are not sophisticated in programming. Internal teams may analyze curated data in order to support new healthcare insights that both help improve patient care and improve life science research. Similarly, external users have easy access to this proprietary real-world data for analysis and access to proprietary statistical models.

A billing model for a user may be provided on a subscription basis or an on-demand basis. For example, a user may subscribe to one or more data sets for a period of time, such as a monthly or yearly subscription, or the user may pay on a per-access basis for data and notebook usage, such as for loading a specific cohort with corresponding notebook and paying a fee to generate the instant results for consumption. Users may desire a benchmarking and optimization portal through which they may view and optimize their storage and computing resources uses.

Generating a notebook may be performed with a GUI for notebook editing. A user may configure a reporting page for a notebook. A reporting page may include text, images, and graphs as selected and populated by the users. Preconfigured elements may be selected from a list, such as a dropdown list or a drag-and-drop menu. Preconfigured elements include statistical analysis modules and machine learning models. For example, a user may wish to perform linear regression on the data with respect to specific features. A user may select linear regression, and a menu with checkboxes may appear with features from their data set which should be supplied to the linear regression model. Once filled out, a template for reporting the linear regression results with respect to the selected features may be added to the reporting page at a location identified by the active cursor or the drop location for a drag- and drop-element. If a user wishes to solve a problem using a machine learning model, it may be added to the sheet. A header may be populated identifying the model, the hypertuning parameters, and the reported results. In some instances, a model that was previously trained may then be applied to the current cohort. In other instances, the model may be trained on the fly, for example by selecting annotated features and associated outcomes for which the model should be trained. In an unsupervised machine learning model, the model may not require selection of annotated features as the features will be identified during training. In some embodiments, if a selected statistical model requires results from a trained model which are not computed in the template, the template may automatically add the trained model to generate the required results prior to inserting the selected statistical model to the notebook.

Statistical analysis models may be predesigned for calculating the arithmetic mean of the cohort with respect to a selected feature, the standard deviation/distribution of the cohort for a selected feature, regression relationships between variables for selected features, sample size determining models for subsetting the cohort into the optimal sub-population for analysis, or t-testing modules for identifying statistically significant features and correlations in the cohort. Other precomputed statistical analysis modules may perform cohort analysis to identify significant correlations and/or features in the cohort, data mining to identify meaningful patterns, or data dredging to match statistical models to the data and report out which models may be applicable and add those models to the notebook.

Machine learning models may apply linear regression algorithms, non-linear regression, logistic regression algorithms, classification models, bootstrap resampling models, subset selection models, dimensionality reduction models, tree-based models (such as bagging, boosting, and random forest), and other supervised or unsupervised models. As each model is selected, a target output may be requested from the user specifying which feature(s) the model should identify, classify, and/or report. For example, a user may select for the model to identify which features most closely correlate to patient survival in the cohort, or which features most closely correlate with a positive treatment outcome in the cohort. The user may also select which classification labels from the classification labels of the model that they wish the model to classify. In an example where the model may classify the cohort according to five labels, the user may specify one or more labels as a binary classification (patient has label, patient does not have label) such as whether a patient with a tumor of unknown origin originated from the breast, lung, or brain. The user may select only breast to identify for any tumors of unknown origin whether the tumor may be classified as coming from the breast or not from the breast.

Figure 29:
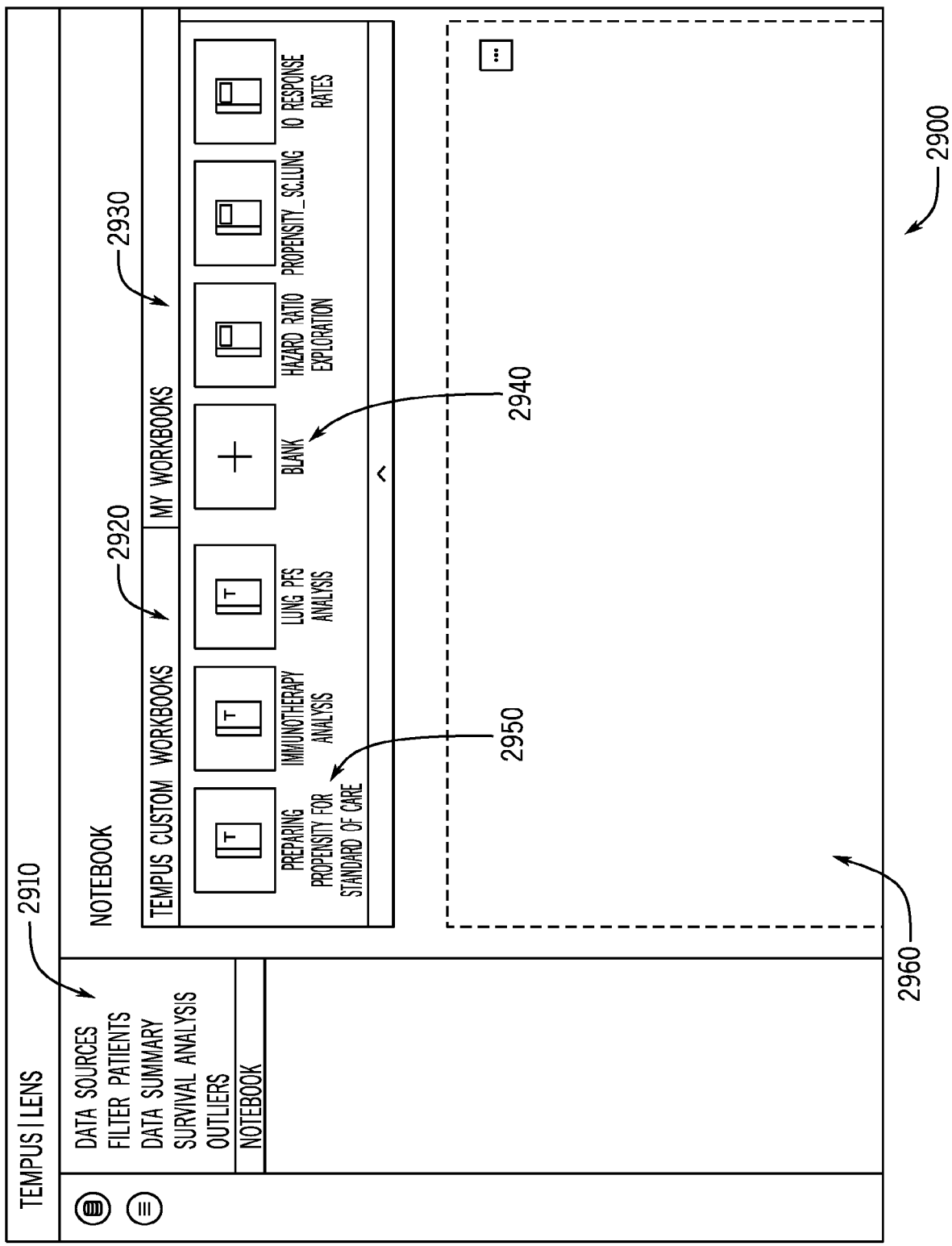
FIG. 29 illustrates an example of a user interface of the Interactive Analysis Portal for generating analytics via one or more notebooks according to certain embodiments.

FIG. 29 illustrates a user interface of the Interactive Analysis Portal 22 for generating analytics via one or more notebooks according to an embodiment.

The notebook user interface 2900 may be accessed by selecting Notebook from the Interactive Analysis Portal 22, such as via a sidebar menu 2910 either before or after filtering a database of patients to a desired cohort of patients via Interactive Cohort Selection Filtering 24.

Notebooks, or workbooks, may be internally curated at the company label by team members proficient in the fields of data science, machine learning, or other fields that routinely perform analytics on patient data and presented to the user via a custom workbooks widget 2920. The custom workbooks widget may be presented as a searchable list, searchable icons, a scrolling window which may scroll horizontally or vertically to display additional workbooks, or an expandable window which expands to provide access to all workbooks for which the user is authorized to access. A workbook may be represented by an icon and associated text, such as illustrated for workbook 2960. The user may also generate personalized workbooks which may be accessed via the my workbooks widget 2930. A workbook viewing window 2950 may be provided to view a workbook selected from widgets 2920 or 2930. New workbooks may be created by the user by selecting a blank workbook 2940. Upon selection of the blank workbook 2940, a workbook generation interface may open.

Figure 30:
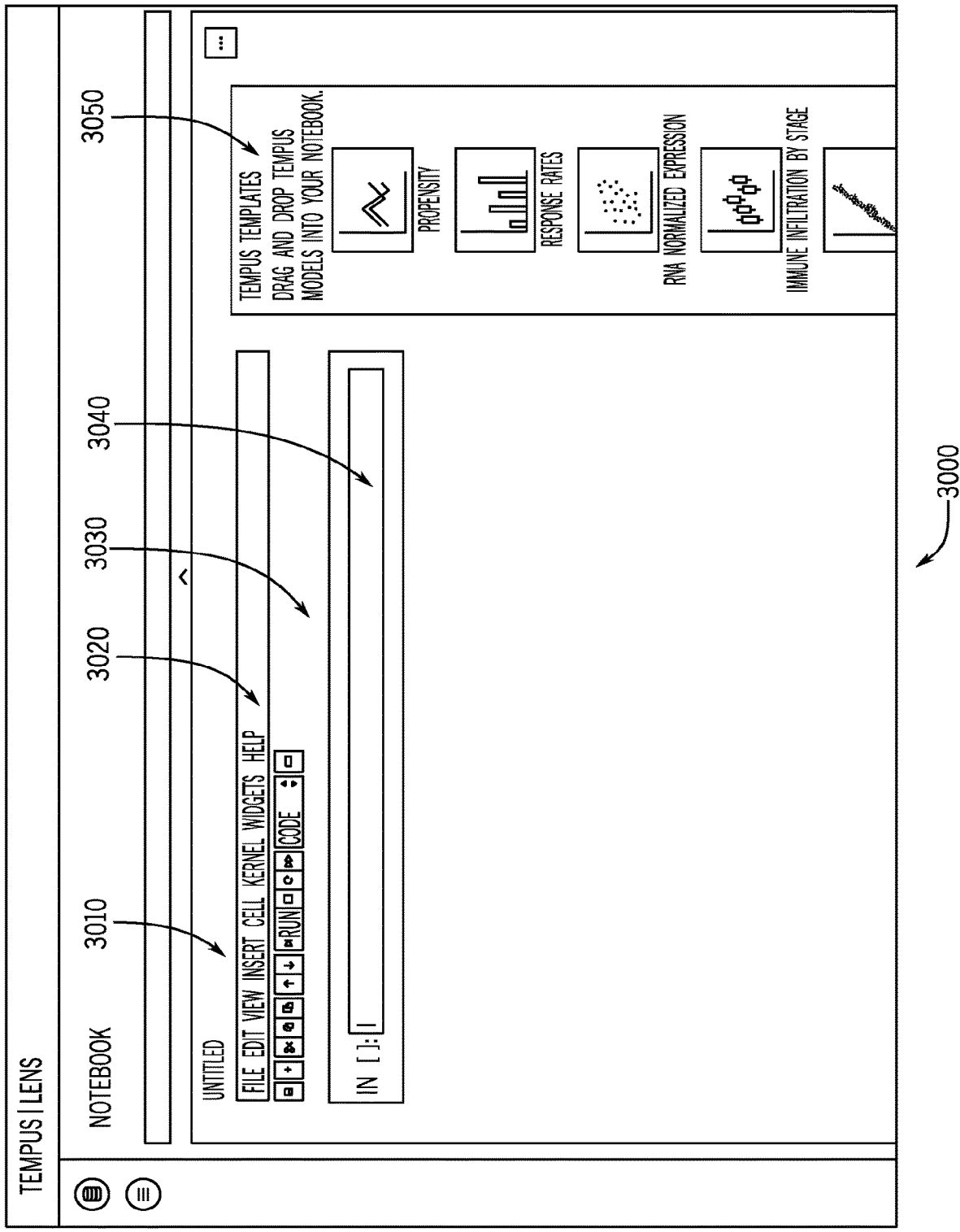
FIG. 30 illustrates a workbook generation interface of the Interactive Analysis Portal for creating a new workbook according to an embodiment.

FIG. 30 illustrates a workbook generation interface of the Interactive Analysis Portal 22 for creating a new workbook according to an embodiment.

Workbook generation interface 3000 may be provided to the user upon selection of a blank workbook from the notebook user interface. A text entry user interface element (UIE) 3010 may be provided to name the workbook for identification, searching, and indexing after generation. A series of button and drop down menu UIEs 3020 may be provided to compartmentalize grouped elements of the user interface. UIEs 3020 may assist the user in building and structuring the workbook's presentation. A cell UIE may provide selections pertaining to the currently selected cell of window 3040 having a block of code, such a commands for running the currently selected cell, terminating the currently selected cell, adding a cell, deleting a cell, running all cells, running all cells above, running all cells below, or terminating all cells. A kernel UIE may provide selections pertaining to one or more programming languages and/or available to the user such as Python, Structured Query Language (SQL), R, Spark, Haskell, Ruby, Typescript, Javascript, Perl, Lua, C, C++, Matlab, Java, Emu86, and other kernels. Selecting a kernel from the kernel UIE reloads the workbook so that the cells execute commands from the respective language. A widget UIE may provide selections pertaining to one or more supported code snippets for the active kernel. Code snippets may include code for creating visualizations such as a graph or a plot, code for simple arithmetic operations such as calculating a mean or a standard deviation, or code for more complex operations such as calculating a distribution and displaying a respective curve. A series of icon UIEs 3030 may be provided where each icon represents a popular command executed from the UIE 3020. Exemplary popular commands may include saving the document, adding a new cell, cutting or pasting code or cells, rearranging cells by moving them upwards or downwards down the page in relation to any other cells, or running/terminating the code in the active cell(s).

One or more cells may be present in window 3040 for a user to insert one or more lines of code for the active kernel. A user may enter code or commands into a cell which may operate on an active database or cohort of patients. Running the cell with execute the entered code or command. Outputs, such as stdout, error messages, or print statements may be displayed directly below the cell upon running. Additionally, a text widget may be inserted which will provide formatting and associated text based upon the code from one or more cells. Such a text widget may provide a simple, readable format for results from execute code. In one embodiment, a text widget may be presented as a markdown cell supporting HTML, indented lists, text formatting, TeX/LaTeX equations, and inline tables.

In one example, a code block may perform arithmetic on a matrix of values. An associated output, such as printing the matrix would result in a difficult to understand series of brackets, parentheticals, and commas. A visualization widget may receive a variable containing the matrix, and provide an image having the matrix values visible in a visible table format that represents a matrix instead of a potentially confusing text output. Cells accept all commands associated with each supported kernel and programming language. A cell may import a module or library from another source (such as dask, fastparaquet, pandas, or other libraries), support data structures, support conditional statements and logic loops, as well as establish and call functions. Cell output is generated asynchronously as the code runs so that the user may view the instantaneous output from the active code. If the output exceeds a preconfigured limit on the number of lines to display, the output may become scrollable text which may autoscroll with new entries or scroll upon user input.

One or more templates may be provided in template window 3050 for the user's convenience. Templates may include one or more cells preconfigured to operate on an input data such as the filtered patient cohort, run one or more cells of code to generate logical results, and run one or more cells of text or visualizations to report out the results of the performed logic on the input data in a convenient manner. Templates may exist for charts, graphs, regressions, dimension reductions, classifications, RNA or DNA normalization, and other commonly used features across templates available to the user. Templates may be provided with the dataset or custom created by a user to be shared with other users.

Figure 31:
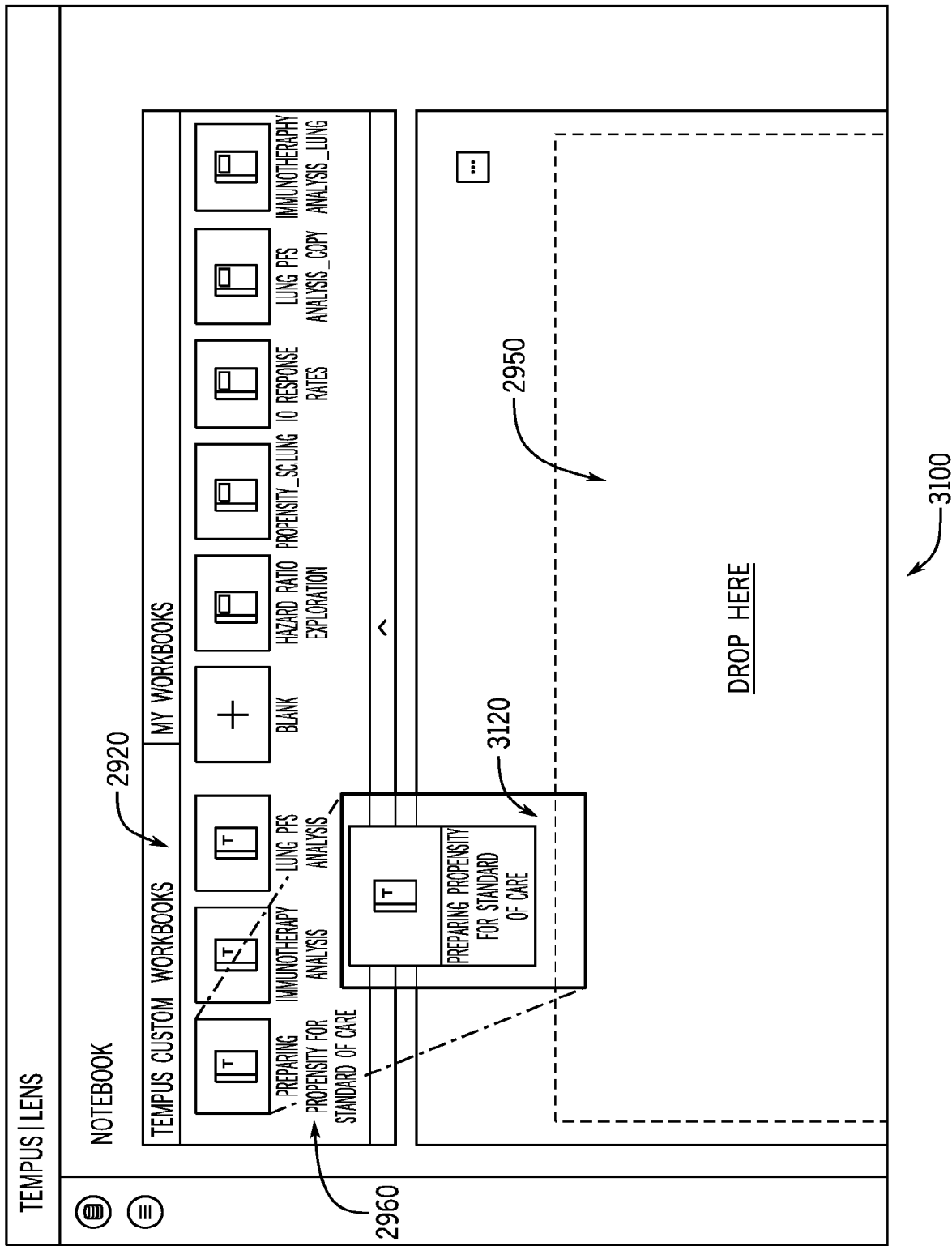
FIG. 31 illustrates opening a preconfigured template from the custom workbooks widget of the notebook user interface.

FIG. 31 illustrates opening a preconfigured template from the custom workbooks widget of the notebook user interface.

Returning to notebook user interface 2900, the user may populate workbook viewing window 2950 with a custom workbook from the custom workbook widget 2920 by clicking and dragging the desired workbook from the widget to the viewing window. In one example, the user may select workbook 2960 with the mouse cursor and drag the workbook to viewing window 2950 as illustrated at 3120. Other intuitive mouse, keyboard, or gesture commands may be implemented in place of, or in addition to, clicking and dragging.

Figure 32:
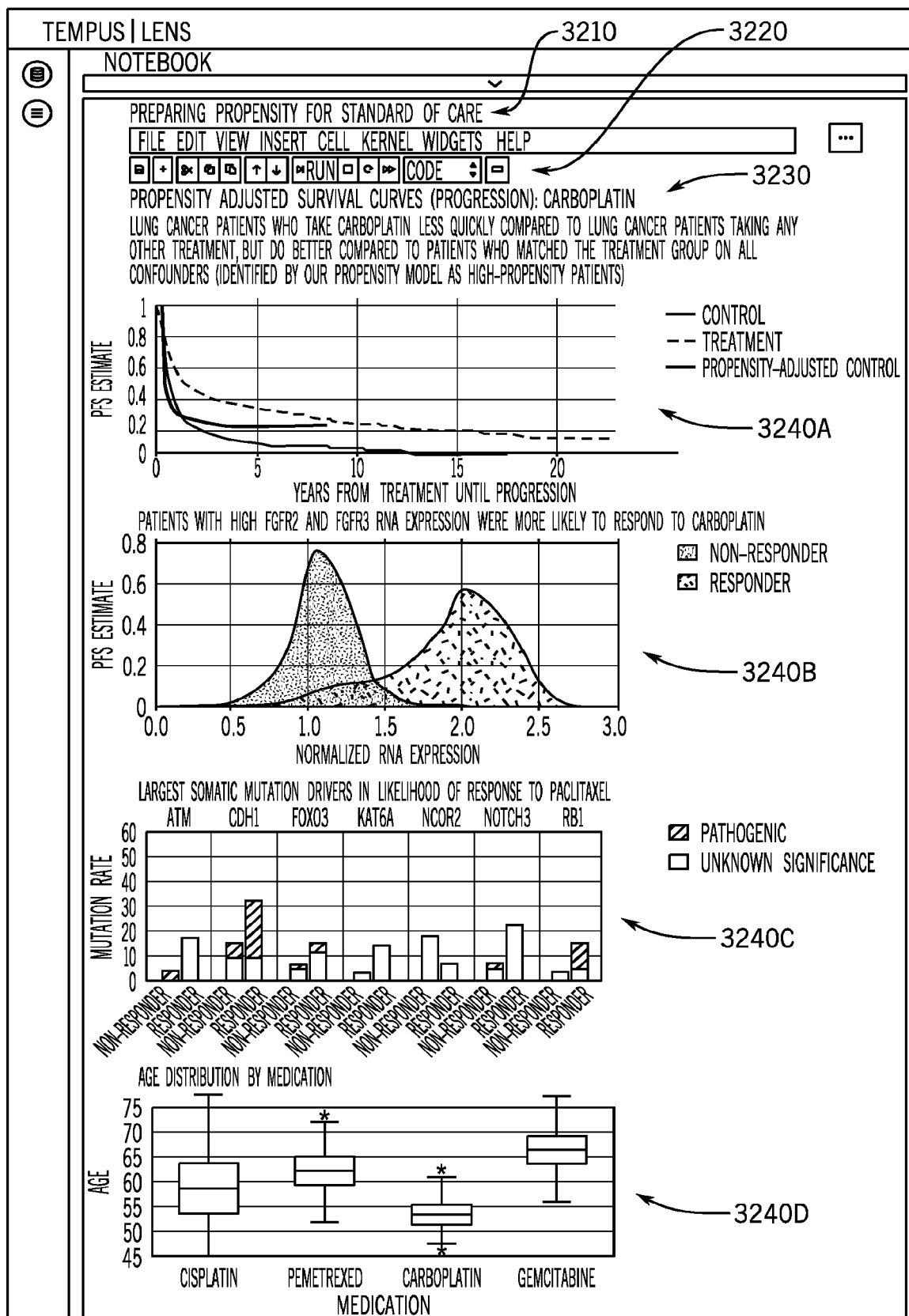
FIG. 32 illustrates a response from the notebook user interface when a user drags a workbook into the viewing window.

FIG. 32 illustrates a response from the notebook user interface when a user drags a workbook into the viewing window.

Notebook editor 3200 may auto-populate with Title 3210 and one or more cells 3240A-D based upon the user selected workbook. The user may rename the workbook using edit the workbook further using a text entry UIE 3220. The user may alter the configuration of the workbook via a series of button and drop down menu UIEs 3220 may be provided to compartmentalize grouped elements of the user interface. UIEs 3220 may assist the user in building and structuring the workbook's presentation. A cell UIE may provide selections pertaining to the currently selected cell 3240A-D having a block of code, such a commands for running the currently selected cell, terminating the currently selected cell, adding a cell, deleting a cell, running all cells, running all cells above, running all cells below, or terminating all cells. A kernel UIE may provide selections pertaining to one or more programming languages and/or available to the user such as Python, Structured Query Language (SQL), R, Spark, Haskell, Ruby, Typescript, Javascript, Perl, Lua, C, C++, Matlab, Java, Emu86, and other kernels. Selecting a kernel from the kernel UIE reloads the workbook so that the cells execute commands from the respective language. A widget UIE may provide selections pertaining to one or more supported code snippets for the active kernel. Code snippets may include code for creating visualizations such as a graph or a plot, code for simple arithmetic operations such as calculating a mean or a standard deviation, or code for more complex operations such as calculating a distribution and displaying a respective curve. The user may further alter the configuration of the workbook via a series of icon UIEs 3230 may be provided where each icon represents a popular command executed from the UIE 3220. Exemplary popular commands may include saving the document, adding a new cell, cutting or pasting code or cells, rearranging cells by moving them upwards or downwards down the page in relation to any other cells, or running/terminating the code in the active cell(s).

The user may also edit the source code for each of cells 3240A-D by selecting the cell and selecting the cell UIE option for edit or pressing an associated keyboard shortcut.

Figure 33:
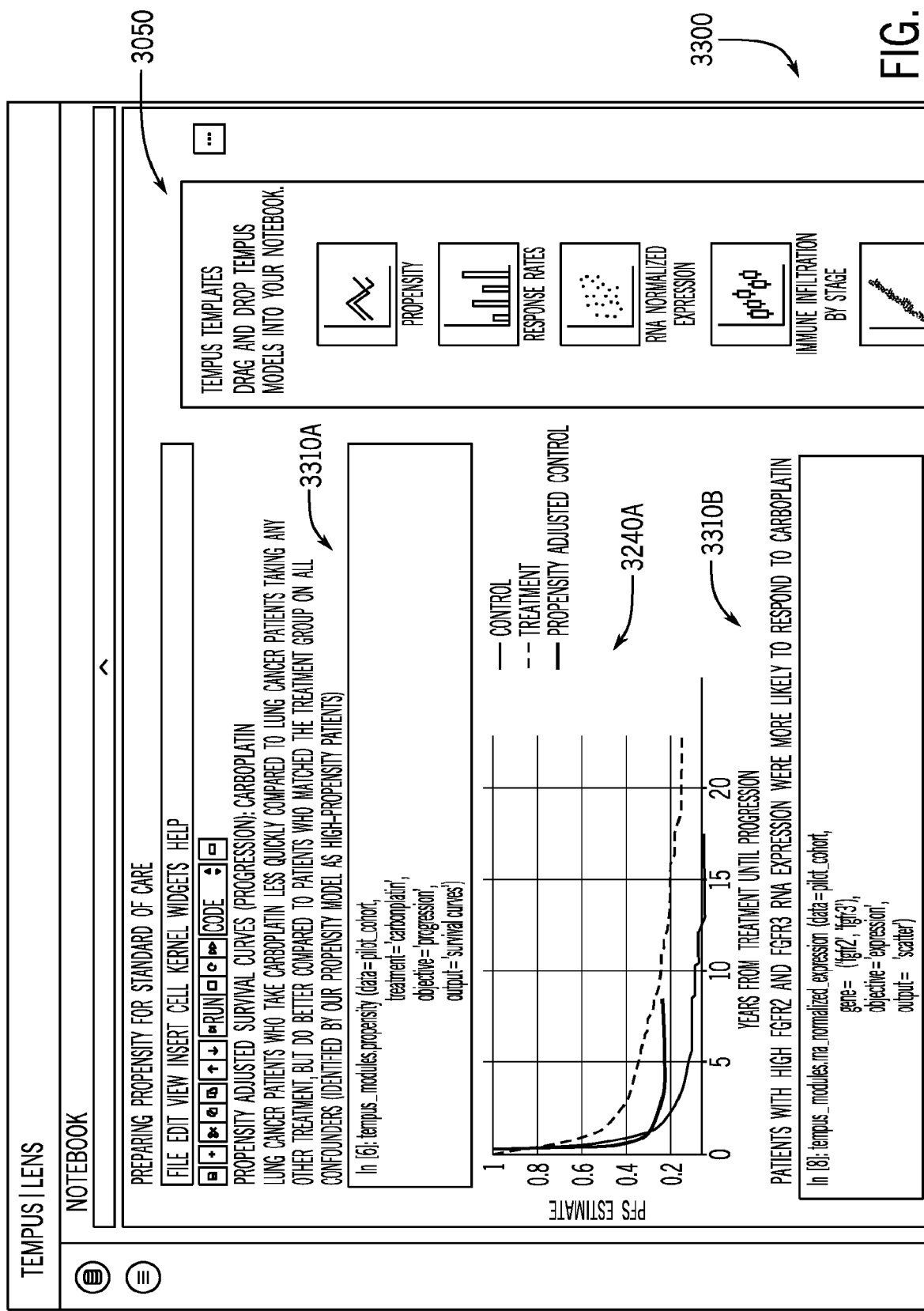
FIG. 33 illustrates an edit cell view of a custom workbook after the user loads a workbook into workbook editor and selects edit from the cell UIE.

FIG. 33 illustrates an edit cell view of a custom workbook after the user loads a workbook into workbook editor 3300 and selects edit from the cell UIE.

Cells 3310A and 3310B become visible (3310C-D not shown) upon entering an edit cell view of the workbook having cells 3240A-D. Cell 3310A displaying the code that generates a survival curve 3240A based on a propensity difference between a control cohort and a treatment cohort of patients. Cell 3310B displaying the code that generates a scatterplot 3240B (not shown) based on normalized RNA expressions for two selected RNA transcriptomes in the filtered cohort of patients. Similar cells 3310C-D (not shown) may be generated for scatter and box plots 3240C-D (not shown) respectively.

The user may edit the code to modify the workbook for their purposes as well as add or remove additional cells to create a new customized workbook.

During edit cell view, the user may also see one or more templates may be provided in template window 3050 for the user's convenience. Templates may include one or more cells preconfigured to operate on an input data such as the filtered patient cohort, run one or more cells of code to generate logical results, and run one or more cells of text or visualizations to report out the results of the performed logic on the input data in a convenient manner. Templates may exist for charts, graphs, regressions, dimension reductions, classifications, RNA or DNA normalization, and other commonly used features across templates available to the user. Templates may be provided with the dataset or custom created by a user to be shared with other users.

The user may drag any template into a cell to populate that cell with the code for generating the template's associated visualization or arithmetic.

Users may access the user interface for databases of patients which have been provisioned to the user by association with an institution or medical facility with a subscription to each patient database. Custom workbooks may also be provided on a database-by-database basis where workbooks are selected for their applicability to the patients within each database. Accessing the user interface may spawn resources in a cloud computing environment with access to any authorized databases and/or workbooks. User resource usage in the cloud computing environment may be monitored and tracked to supplement accurate billing for resources consumed by the user. User's may request and purchase other databases of patients. Databases of patients may be purchased based on characteristics of the patients within them. For example, a user may desire a database of patients who have been diagnosed with breast cancer. A look-up table (LUT) or cancer ontology may be referenced to provide alternative matchings for breast cancer, such as ductal carcinoma of the breast, cancer of the breast, mammary carcinoma, breast carcinoma, or other relevant terminology. Patients satisfying the requested diagnosis and any of the alternative terminologies from the LUT or cancer ontology may be combined into a database and delivered to the user. The user may then perform statistical analysis and research on the data in accordance with the disclosure herein.

Other web interfaces may be incorporated into the Interactive Analysis Portal 22 similar to the Outliers, Smart Cohorts, and Notebook portals above. One such other web interface may include identifying effects of a therapy, procedure, clinical trial, or other medical event on a disease state of a patient using propensity scoring. Propensity scoring and associated web interface is described in further detail in U.S. patent application Ser. No. 16/679,054, titled "Evaluating Effect of Event on Condition Using Propensity Scoring," filed Nov. 8, 2019, which is incorporated herein by reference in its entirety.

Figure 34:
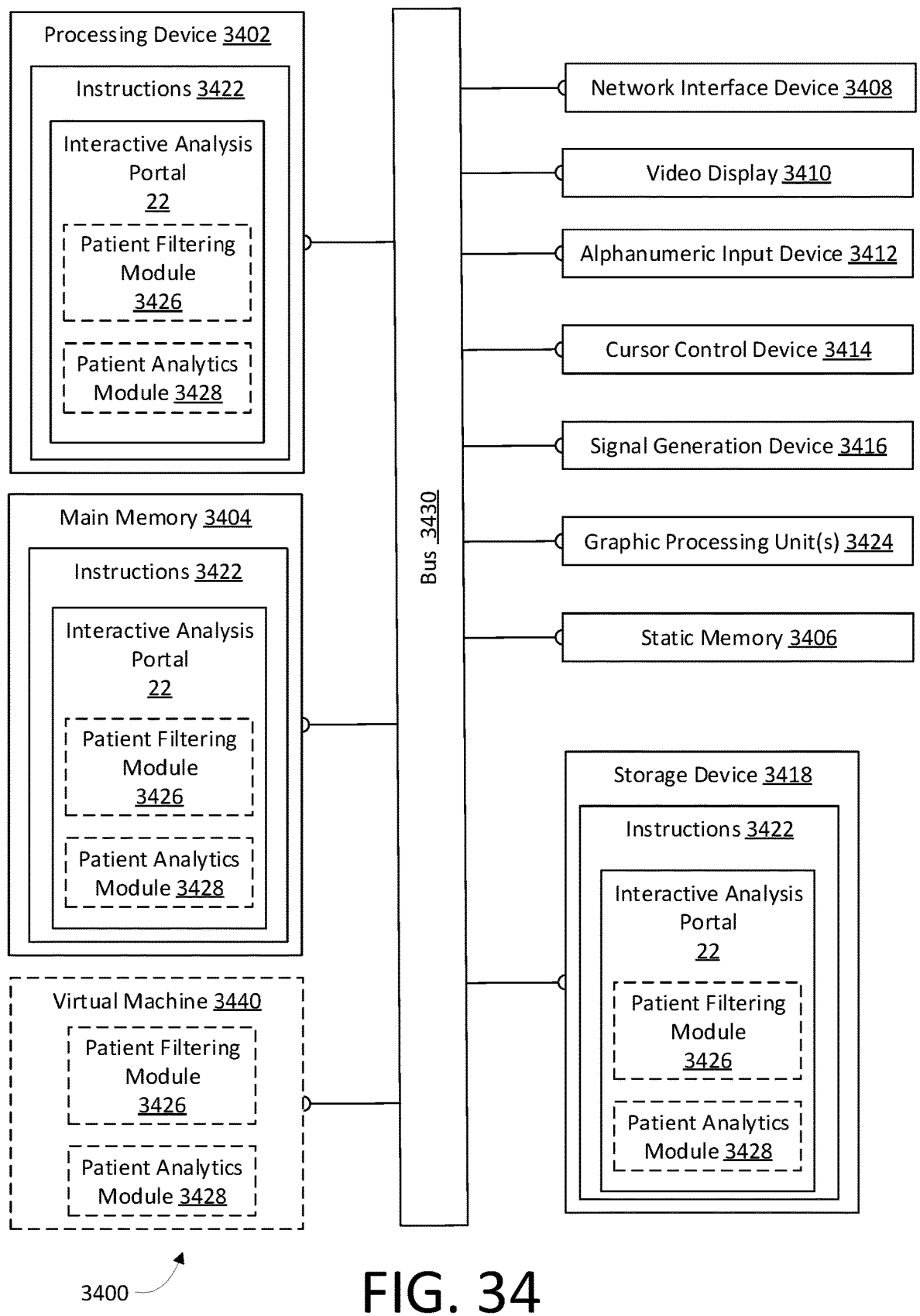
FIG. 34 is an illustration of a block diagram of an implementation of a computer system in which some implementations of the disclosure may operate.

FIG. 34 is an illustration of an example machine of a computer system 3400 within which a set of instructions, for causing the machine to perform any one or more of the methodologies discussed herein, may be executed. In alternative implementations, the machine may be connected (such as networked) to other machines in a LAN, an intranet, an extranet, and/or the Internet.

The machine may operate in the capacity of a server or a client machine in a client-server network environment, as a peer machine in a peer-to-peer (or distributed) network environment, or as a server or a client machine in a cloud computing infrastructure or environment. The machine may be a personal computer (PC), a tablet PC, a set-top box (STB), Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 3400 includes a processing device 3402, a main memory 3404 (such as read-only memory (ROM), flash memory, dynamic random access memory (DRAM) such as synchronous DRAM (SDRAM) or DRAM, etc.), a static memory 3406 (such as flash memory, static random access memory (SRAM), etc.), and a data storage device 3418, which communicate with each other via a bus 3430.

Processing device 3402 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 3402 may also be one or more special-purpose processing devices such as an application specific integrated circuit (ASIC), a field programmable gate array (FPGA), a digital signal processor (DSP), network processor, or the like. The processing device 3402 is configured to execute instructions 3422 for performing the operations and steps discussed herein.

The computer system 3400 may further include a network interface device 3408 for connecting to the LAN, intranet, internet, and/or the extranet. The computer system 3400 also may include a video display unit 3410 (such as a liquid crystal display (LCD) or a cathode ray tube (CRT)), an alphanumeric input device 3412 (such as a keyboard), a cursor control device 3414 (such as a mouse), a signal generation device 3416 (such as a speaker), and a graphic processing unit 3424 (such as a graphics card).

The data storage device 3418 may be a machine-readable storage medium (also known as a computer-readable medium) on which is stored one or more sets of instructions or software 3422 embodying any one or more of the methodologies or functions described herein. The instructions 3422 may also reside, completely or at least partially, within the main memory 3404 and/or within the processing device 3402 during execution thereof by the computer system 3400, the main memory 3404 and the processing device 3402 also constituting machine-readable storage media.

In one implementation, the instructions 3422 include instructions for an interactive analysis portal (such as interactive analysis portal 22 of FIG. 1) and/or a software library containing methods that function as an interactive analysis portal. The instructions 3422 may further include instructions for a patient filtering module 3426 (such as the interactive cohort selection filtering interface 24 of FIG. 1) and a patient analytics module 3428 (such as the cohort funnel and population analysis interface 26, the patient timeline analysis user interface 28, the patient survival analysis user interface 30, and/or the patient event likelihood analysis user interface 32 of FIG. 1). While the data storage device 3418/machine-readable storage medium is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine readable storage medium as a transitory storage medium or transitory machine-readable storage medium.

In another implementation, a virtual machine 3440 may include a module for executing instructions for a patient filtering module 3426 (such as the interactive cohort selection filtering interface 24 of FIG. 1) and a patient analytics module 3428 (such as the cohort funnel and population analysis interface 26, the patient timeline analysis user interface 28, the patient survival analysis user interface 30, and/or the patient event likelihood analysis user interface 32 of FIG. 1). In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

What is claimed is:

1. A method for identifying and separating groups of patients from a cohort of patients based on one or more targets, comprising:
   receiving patient information for the cohort of patients;
   identifying one or more interactions for each of one or more patients based at least in part on the received patient information;
   generating, for the one or more targets at each of the one or more interactions, one or more timeline metrics identifying whether each of the one or more targets occurs within a time period of an occurrence of the interaction;
   identifying, for each timeline metric of the one or more timeline metrics, whether a patient may incur one or more status characteristics within the time period;

training a machine learning algorithm or a neural network implemented by a computer system to produce a target prediction model for each of the one or more targets based at least in part on the one or more status characteristics;

generating, by the target prediction model, predictions for each of the one or more status characteristics for the one or more of patients;

associating the predictions with a respective one or more timeline metrics of the one or more timeline metrics;

generating, by the prediction model, a decision tree based on determining a greatest difference between each of the predictions and the timeline metrics, wherein the decision tree comprises a plurality of leaf nodes, each leaf node associated with a respective group of patients of the cohort of patients, each of the groups comprising similarities based at least in part on at least one status characteristic identified from respective branches leading to the leaf node, and wherein fewer than all of the patients in a leaf node satisfy the at least one status characteristic;

providing importance ranks for the at least one status characteristic based on the fewer than all of the patients, wherein the importance ranks are provided without needing to retrain the target prediction model; and identifying at least one status characteristic for a patient not included in the cohort of patients based on matching the patient with one of the groups of patients associated with one of the plurality of leaf nodes.

2. The method of claim 1, wherein training a prediction model for each of the one or more targets based at least in part on the one or more status characteristics further comprises:

training the prediction model using gradient boosting based at least in part on the one or more status characteristics.

3. The method of claim 1, wherein the patient information includes data relating to each patient's medical history, treatments, and survival.

4. The method of claim 1, wherein an interaction of the one or more interactions comprises at least one of:
a record from a medical history of a patient of the one or more patients,
a record of a diagnosis,
a record of a medication,
a record of a treatment, surgery, therapy, or procedure,
a record of a cancer progression, or
a record of a genetic sequencing.

5. The method of claim 1, wherein the one or more targets include at least one of progression free survival of a patient of the one or more patients or survival of a patient of the one or more patients.

6. The method of claim 1, wherein the time period is measured in at least one of days, months, or years.

7. The method of claim 1, wherein a status characteristic of the one or more status characteristics comprises at least one of:
a prior occurrence of an interaction,
a prior result of a laboratory test,
a future occurrence of an interaction,
a future result of a laboratory test, or
a characteristic that is measured as a unit of 'time since occurrence' for prior interactions.

8. The method of claim 1, wherein the one or more status characteristics include forward status characteristics that relate to the patients.

9. The method of claim 8, wherein the forward status characteristics are actionable.

10. The method of claim 9, wherein the actionable forward status characteristics include at least one of: prescribing one or more medications, prescribing a treatment, or sequencing a sample.

11. The method of claim 1, further comprising:
receiving the associated predictions for each patient from the target prediction model;
receiving an anchor point;
identifying one or more subsets of the one or more patients for which predicted targets, at the anchor point, deviate from an observed target occurrence for the cohort of patients; and
transmitting information to a clinician indicating that a particular patient may experience similar results to the one or more of the subsets of patients based at least in part on patient information for the particular patient.

12. The method of claim 11, wherein the anchor point is determined based on an interaction of the one or more interactions, comprising at least one of:
a record from a medical history of a patient of the one or more patients,
a record of a diagnosis,
a record of a medication,
a record of a treatment, surgery, therapy, or procedure,
a record of a cancer progression, or
a record of a genetic sequencing.

13. The method of claim 11, wherein the anchor point is determined based on a status characteristic of the one or more status characteristics, comprising at least one of:
a prior occurrence of an interaction,
a prior result of a laboratory test,
a future occurrence of an interaction,
a future result of a laboratory test, or
a characteristic that is measured as a unit of 'time since occurrence' for prior interactions.

14. The method of claim 11, further comprising:
receiving a selection of one or more forward status characteristics.

15. The method of claim 14, wherein the forward status characteristics include one or more of medications, sequencing, or germline sequencing.

16. The method of claim 14, further comprising:
providing the selected one or more forward status characteristics at the anchor point to the target prediction model.

17. The method of claim 14, wherein, for each branch node of the decision tree, a pair of branches extending therefrom are formed based on at least one status characteristic selected from the one or more forward status characteristics.

18. The method of claim 1, wherein all of the patients in a leaf node of the plurality of leaf nodes satisfy at least one status characteristic.

19. The method of claim 1, wherein providing importance ranks further comprises calculating a population mean prediction.

20. The method of claim 19, wherein providing importance ranks further comprises encoding categorical status characteristic levels as a difference between the predicted value and the population mean prediction.

21. The method of claim 20, wherein providing importance ranks further comprises clustering continuous status characteristics.

22. The method of claim 21, wherein providing importance ranks further comprises aggregating an average difference between the predicted value and the population mean prediction per categorical status characteristic level.

23. The method of claim 22, wherein providing importance ranks further comprises, for each status characteristic, assigning an overall status characteristic importance as a frequency-weighted sum of an absolute value of all differences between the predicted value and the population mean prediction.

24. The method of claim 1, wherein generating the decision tree based on determining the greatest difference between each of the predictions and the timeline metrics further comprises:
generating the decision tree until a number of patients in a leaf node of the plurality of leaf nodes is less than a minimum number of patients.

25. The method of claim 1, wherein generating the decision tree based on determining the greatest difference between each of the predictions and the timeline metrics further comprises:
generating the decision tree until a number of levels of the decision tree is equal to a maximum number of levels.

26. A system for identifying and separating groups of patients from a cohort of patients based on one or more targets, comprising:
at least one computer system configured to:
receive patient information for the cohort of patients;
identify one or more interactions for each of one or more patients based at least in part on the received patient information;
generate, for the one or more targets at each of the one or more interactions, one or more timeline metrics identifying whether each of the one or more targets occurs within a time period of an occurrence of the interaction;
identify, for each timeline metric of the one or more timeline metrics, whether a patient may incur one or more status characteristics within the time period;
train a machine learning algorithm or a neural network to produce a target prediction model for each of the one or more targets based at least in part on the one or more status characteristics;
generate, by the target prediction model, predictions for each of the one or more status characteristics for the one or more of patients;
associate the predictions with a respective one or more timeline metrics of the one or more timeline metrics;
generate, by the prediction model, a decision tree based on determining a greatest difference between each of the predictions and the timeline metrics, wherein the decision tree comprises a plurality of leaf nodes, each leaf node associated with a respective group of patients of the cohort of patients, each of the groups comprising similarities based at least in part on at least one status characteristic identified from respective branches leading to the leaf node, and wherein fewer than all of the patients in a leaf node satisfy the at least one status characteristic;
provide importance ranks for the at least one status characteristic based on the fewer than all of the patients, wherein the importance ranks are provided without needing to retrain the target prediction model; and
identify at least one status characteristic for a patient not included in the cohort of patients based on matching the patient with one of the groups of patients associated with one of the plurality of leaf nodes.

27. A computer program product for identifying and separating groups of patients from a cohort of patients based on one or more targets, comprising instructions stored on a non-transitory computer readable medium to cause at least one computer system to:
receive patient information for the cohort of patients;
identify one or more interactions for each of one or more patients based at least in part on the received patient information;
generate, for the one or more targets at each of the one or more interactions, one or more timeline metrics identifying whether each of the one or more targets occurs within a time period of an occurrence of the interaction;
identify, for each timeline metric of the one or more timeline metrics, whether a patient may incur one or more status characteristics within the time period;
train a machine learning algorithm or a neural network to produce a target prediction model for each of the one or more targets based at least in part on the one or more status characteristics;
generate, by the target prediction model, predictions for each of the one or more status characteristics for the one or more of patients;
associate the predictions with a respective one or more timeline metrics of the one or more timeline metrics;
generate, by the prediction model, a decision tree based on determining a greatest difference between each of the predictions and the timeline metrics, wherein the decision tree comprises a plurality of leaf nodes, each leaf node associated with a respective group of patients of the cohort of patients, each of the groups comprising similarities based at least in part on at least one status characteristic identified from respective branches leading to the leaf node, and wherein fewer than all of the patients in a leaf node satisfy the at least one status characteristic;
provide importance ranks for the at least one status characteristic based on the fewer than all of the patients, wherein the importance ranks are provided without needing to retrain the target prediction model; and
identify at least one status characteristic for a patient not included in the cohort of patients based on matching the patient with one of the groups of patients associated with one of the plurality of leaf nodes.

* * * * *